United States Patent
Burns et al.

(10) Patent No.: US 10,335,539 B2
(45) Date of Patent: Jul. 2, 2019

(54) DEVICES AND METHODS FOR MODULATING MEDIUM DELIVERY

(71) Applicant: Osprey Medical, Inc., Minnetonka, MN (US)

(72) Inventors: Matthew M. Burns, Deephaven, MN (US); Tuan M. Doan, Burnsville, MN (US); Rodney L. Houfburg, Prior Lake, MN (US); David M. Kaye, Beaumaris (AU); Daniel R. Mans, Victoria, MN (US); Todd J. Mortier, Mound, MN (US)

(73) Assignee: Osprey Medical, Inc., Minnetonka, MN (US)

( * ) Notice: Subject to any disclaimer, the term of this patent is extended or adjusted under 35 U.S.C. 154(b) by 229 days.

(21) Appl. No.: 15/081,041

(22) Filed: Mar. 25, 2016

(65) Prior Publication Data

US 2016/0310660 A1    Oct. 27, 2016

Related U.S. Application Data

(60) Continuation of application No. 14/660,410, filed on Mar. 17, 2015, which is a division of application No.
(Continued)

(51) Int. Cl.
*A61M 5/14*      (2006.01)
*A61M 5/00*      (2006.01)
(Continued)

(52) U.S. Cl.
CPC .......... *A61M 5/1413* (2013.01); *A61M 5/007* (2013.01); *A61M 5/145* (2013.01);
(Continued)

(58) Field of Classification Search
CPC ........ A61M 5/48; A61M 5/486; A61M 5/482; A61M 2039/2413; A61M 2205/3331;
(Continued)

(56) References Cited

U.S. PATENT DOCUMENTS 3,987,941 A    10/1976    Blessing
4,525,165 A     6/1985    Fischell
(Continued)

FOREIGN PATENT DOCUMENTS

JP    H0551307 B2    8/1993
JP    H0566823 B2    9/1993
(Continued)

OTHER PUBLICATIONS

Cilurzo F, Selmin F, Minghetti P, et al. Injectability Evaluation: An Open Issue. AAPS PharmSciTech. 2011;12(2):604-609. doi:10.1208/s12249-011-9625-y.*
(Continued)

*Primary Examiner* — Bradley J Osinski
*Assistant Examiner* — Nilay J Shah
(74) *Attorney, Agent, or Firm* — Mai-Tram D. Lauer; Westman, Champlin & Koehler, P.A.

(57) ABSTRACT

Devices, systems and methods for controlling, regulating, altering, transforming or otherwise modulating the delivery of a substance to a delivery site. The devices, systems and methods optimize the delivery of the substance to an intended site, such as a vessel, vascular bed, organ and/or other corporeal structures, while reducing inadvertent introduction or reflux substance to other vessels, vascular beds, organs, and/or other structures, including systemic introduction.

7 Claims, 41 Drawing Sheets

Exemplary Constant Force Modulator – Filling Injector

Related U.S. Application Data

13/839,771, filed on Mar. 15, 2013, now Pat. No. 9,320,846.

(60) Provisional application No. 61/694,137, filed on Aug. 28, 2012.

(51) Int. Cl.
*A61M 5/142* (2006.01)
*F04B 11/00* (2006.01)
*A61M 5/48* (2006.01)
*A61M 5/168* (2006.01)
*A61M 25/00* (2006.01)
*A61M 5/145* (2006.01)
*A61M 39/24* (2006.01)
*G06F 19/00* (2018.01)

(52) U.S. Cl.
CPC .... *A61M 5/14212* (2013.01); *A61M 5/16881* (2013.01); *A61M 5/48* (2013.01); *A61M 5/482* (2013.01); *A61M 5/484* (2013.01); *A61M 5/488* (2013.01); *A61M 25/0075* (2013.01); *A61M 39/24* (2013.01); *F04B 11/0033* (2013.01); *G06F 19/3468* (2013.01); *A61M 5/14216* (2013.01); *A61M 2025/0076* (2013.01); *A61M 2039/2413* (2013.01); *A61M 2205/3331* (2013.01); *A61M 2205/3334* (2013.01); *A61M 2205/3337* (2013.01); *A61M 2205/3341* (2013.01); *A61M 2205/3344* (2013.01); *A61M 2205/3355* (2013.01); *A61M 2206/22* (2013.01); *A61M 2210/125* (2013.01); *A61M 2210/127* (2013.01); *G06F 19/3456* (2013.01)

(58) Field of Classification Search
CPC .. A61M 2205/3334; A61M 2205/3337; A61M 2205/3341; A61M 2205/3344; A61M 2205/3351; A61M 2205/3355; A61M 2210/125; A61M 2210/127; A61M 5/1408; A61M 5/1407; A61M 39/24; A61M 5/16809; A61M 5/204

See application file for complete search history.

(56) References Cited

U.S. PATENT DOCUMENTS

| | | | |
|---|---|---|---|
| 4,666,429 A | | 5/1987 | Stone |
| 4,935,009 A | * | 6/1990 | Caldwell ............. A61M 5/1424 604/218 |
| 4,997,420 A | * | 3/1991 | LeFevre ................ A61M 5/145 128/DIG. 12 |
| 5,575,767 A | * | 11/1996 | Stevens ................. A61M 5/007 137/539 |
| 5,957,911 A | | 9/1999 | Nesto |
| 6,854,461 B2 | | 2/2005 | Nichols |
| 7,955,301 B1 | | 6/2011 | McKay |
| 7,998,114 B2 | | 8/2011 | Lombardi |
| 2003/0040722 A1 | | 2/2003 | Massengale |
| 2004/0082920 A1 | | 4/2004 | Mori |
| 2004/0138615 A1 | * | 7/2004 | Lombardi ............. A61B 90/00 604/118 |
| 2010/0305507 A1 | | 12/2010 | Duncan |

FOREIGN PATENT DOCUMENTS

| | | |
|---|---|---|
| JP | H0630905 A | 2/1994 |
| JP | 2004528137 A | 9/2004 |
| JP | 2011112513 A | 6/2011 |

OTHER PUBLICATIONS

Japanese Office Action and translation dated Jun. 6, 2017 for Japanese Patent Application No. 2015529834.
Japanese Office Action and English Translation dated Nov. 21, 2017 for Japanese Patent Application No. 2015-529834.
Office Action dated May 24, 2017 for U.S. Appl. No. 14/660,410.
Patent Examination Report dated Nov. 15, 2016 for corresponding Australian Patent Application No. 2013309319.
Office Action dated Mar. 9, 2018 for U.S. Appl. No. 14/660,410.

* cited by examiner

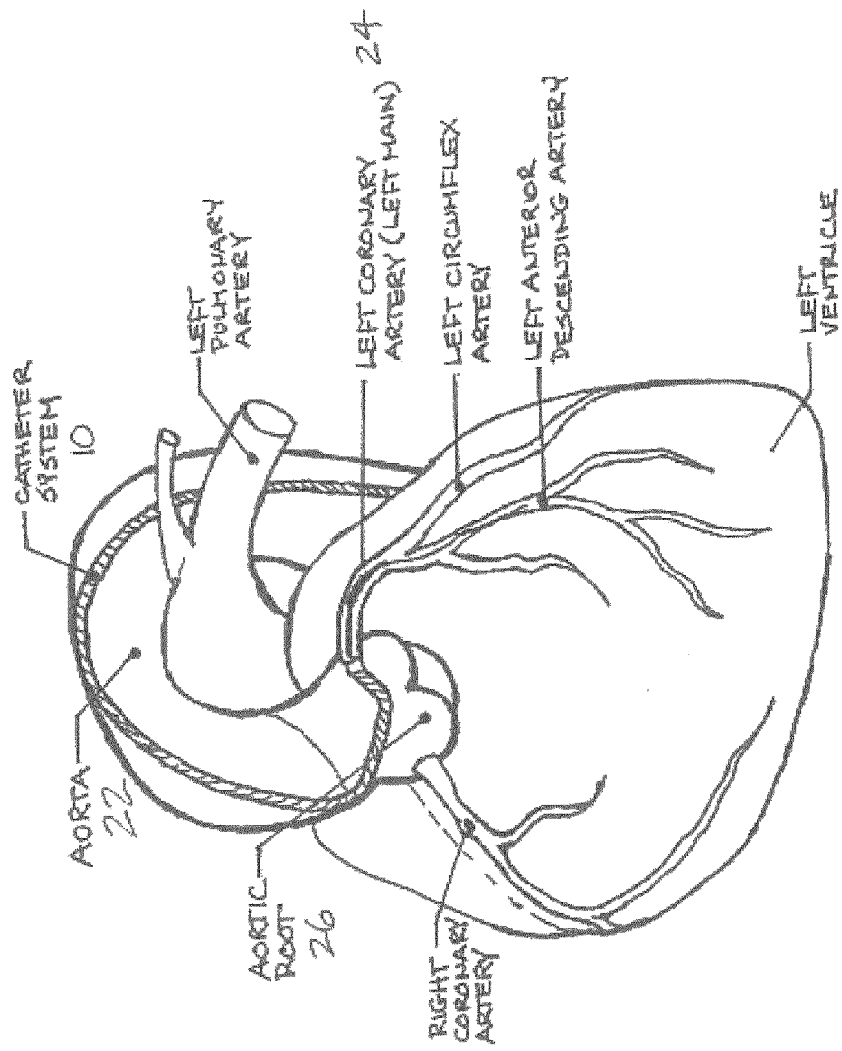

Distal Portion of Exemplary Tx System of Figure 3A

Proximal Portion of Exemplary Tx System of Figure 3A

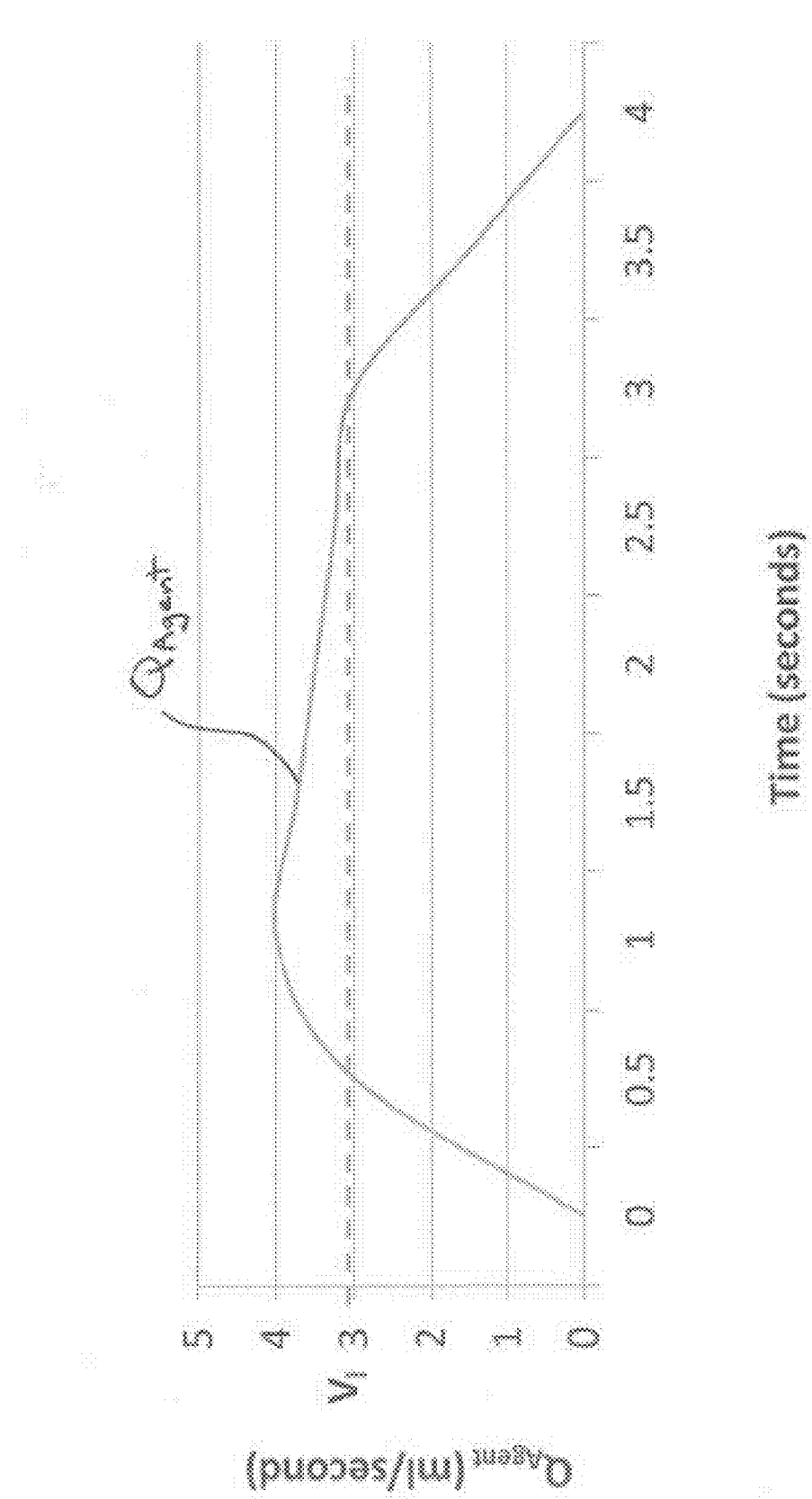

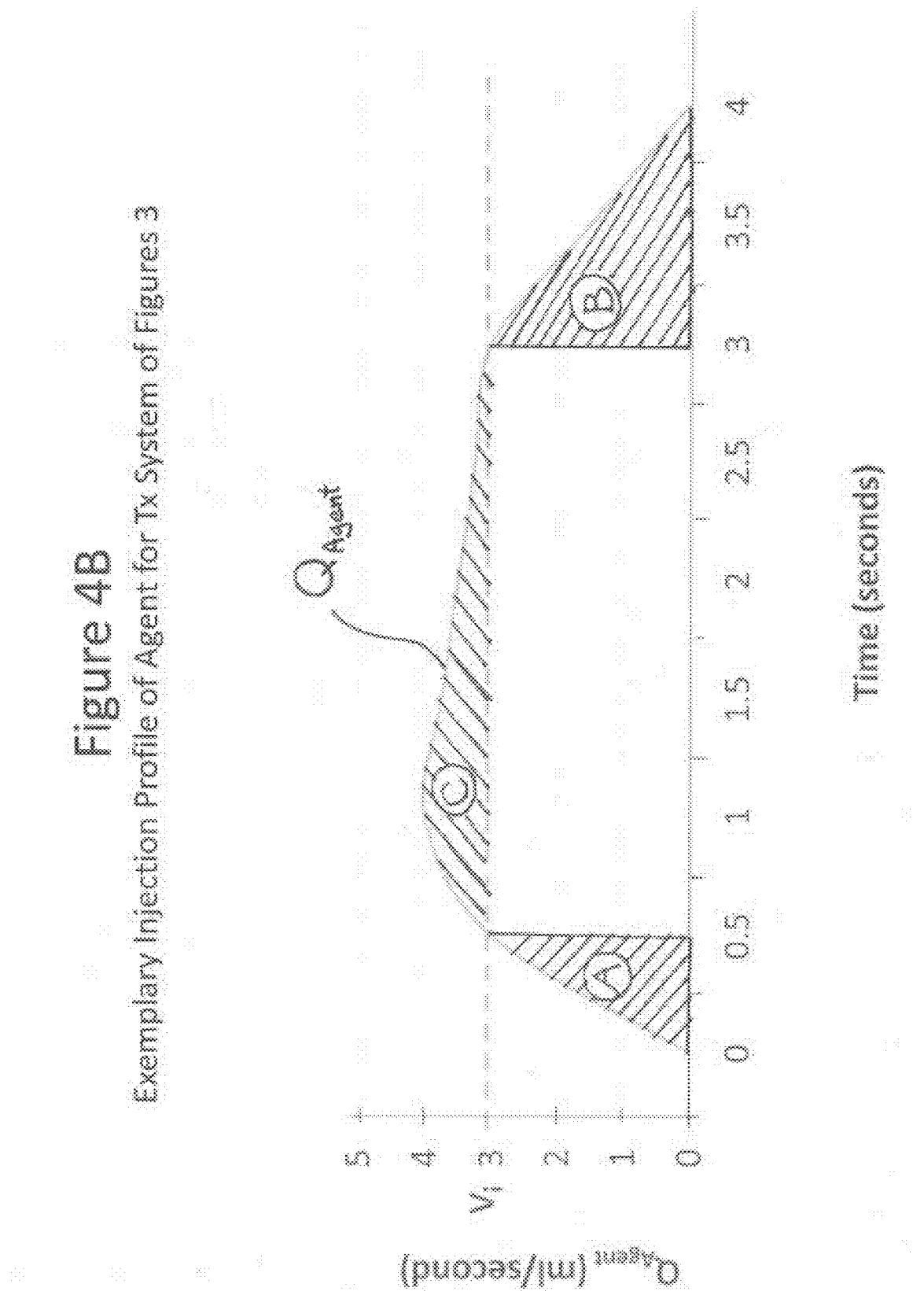

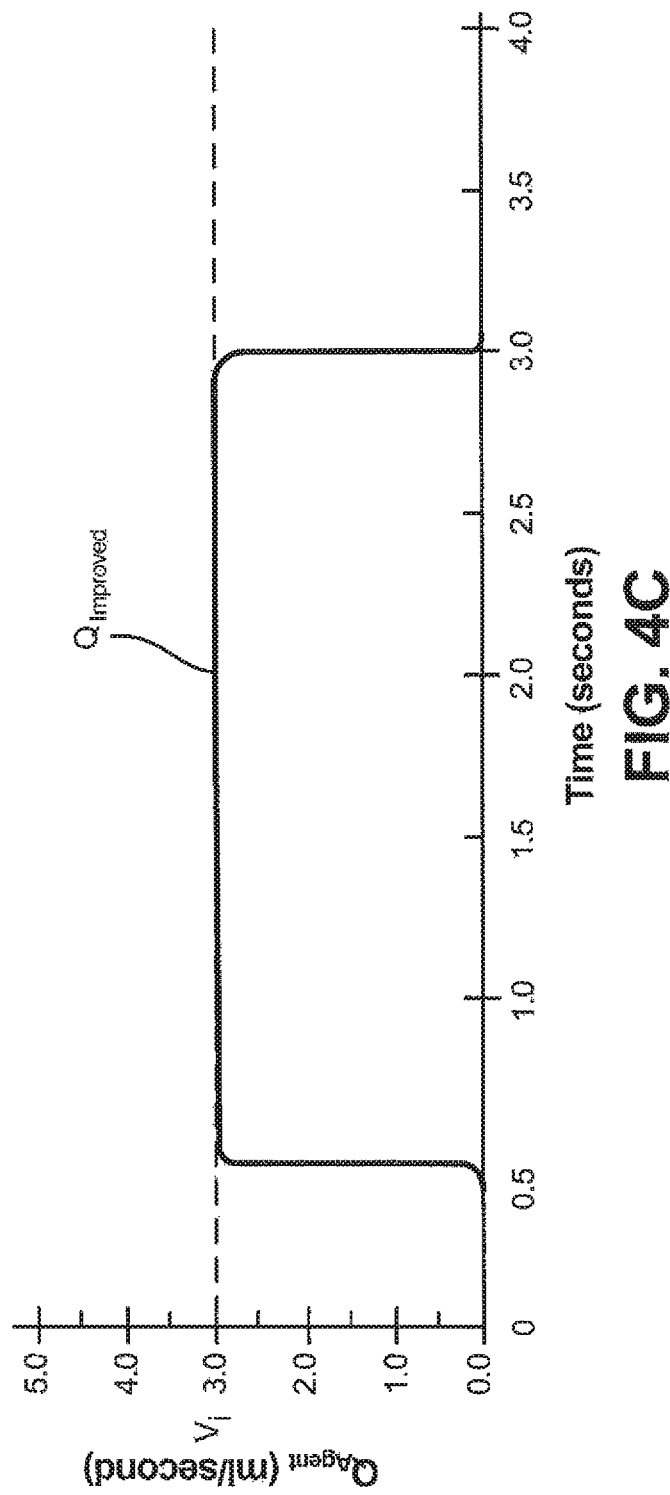

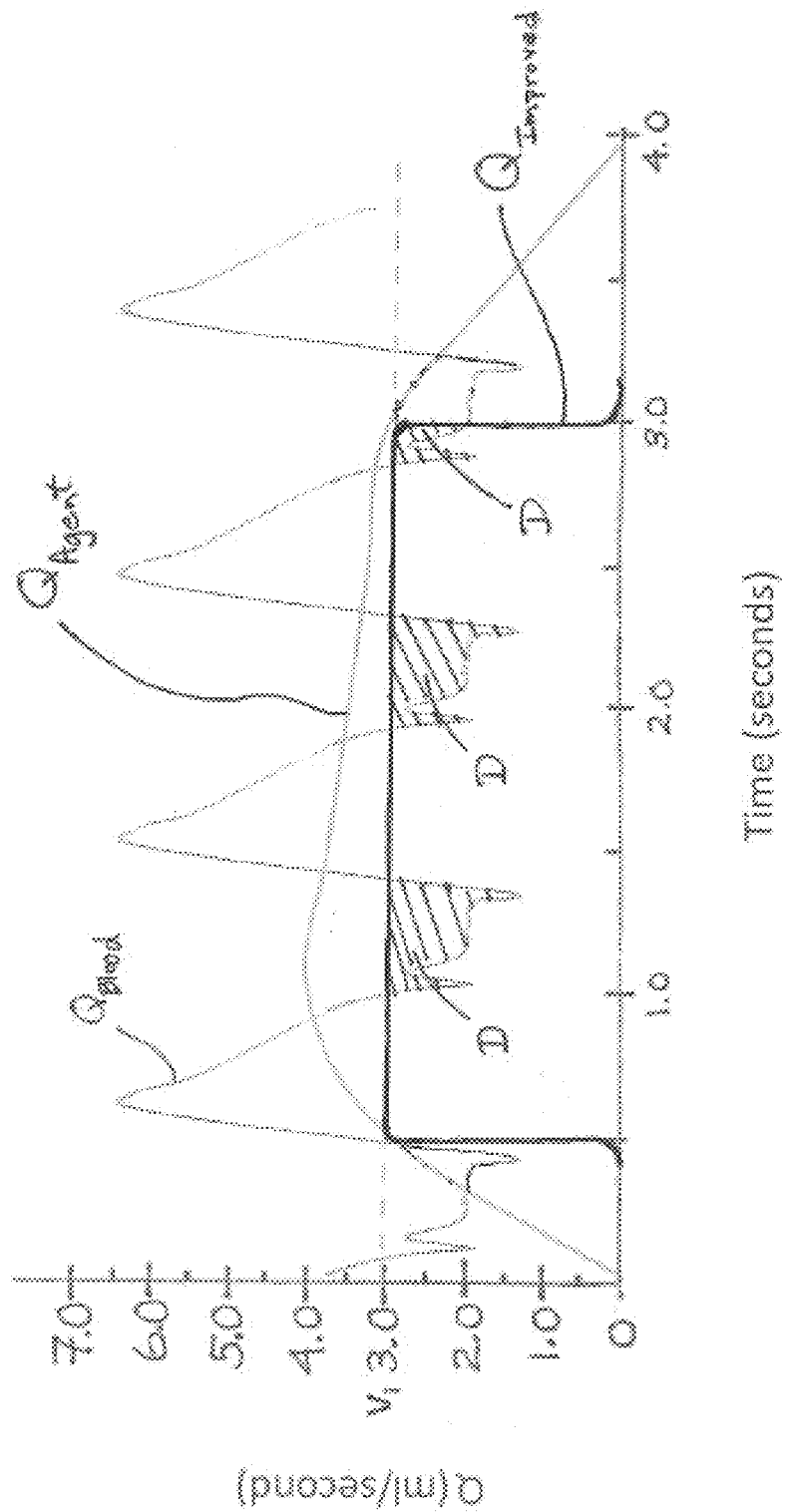

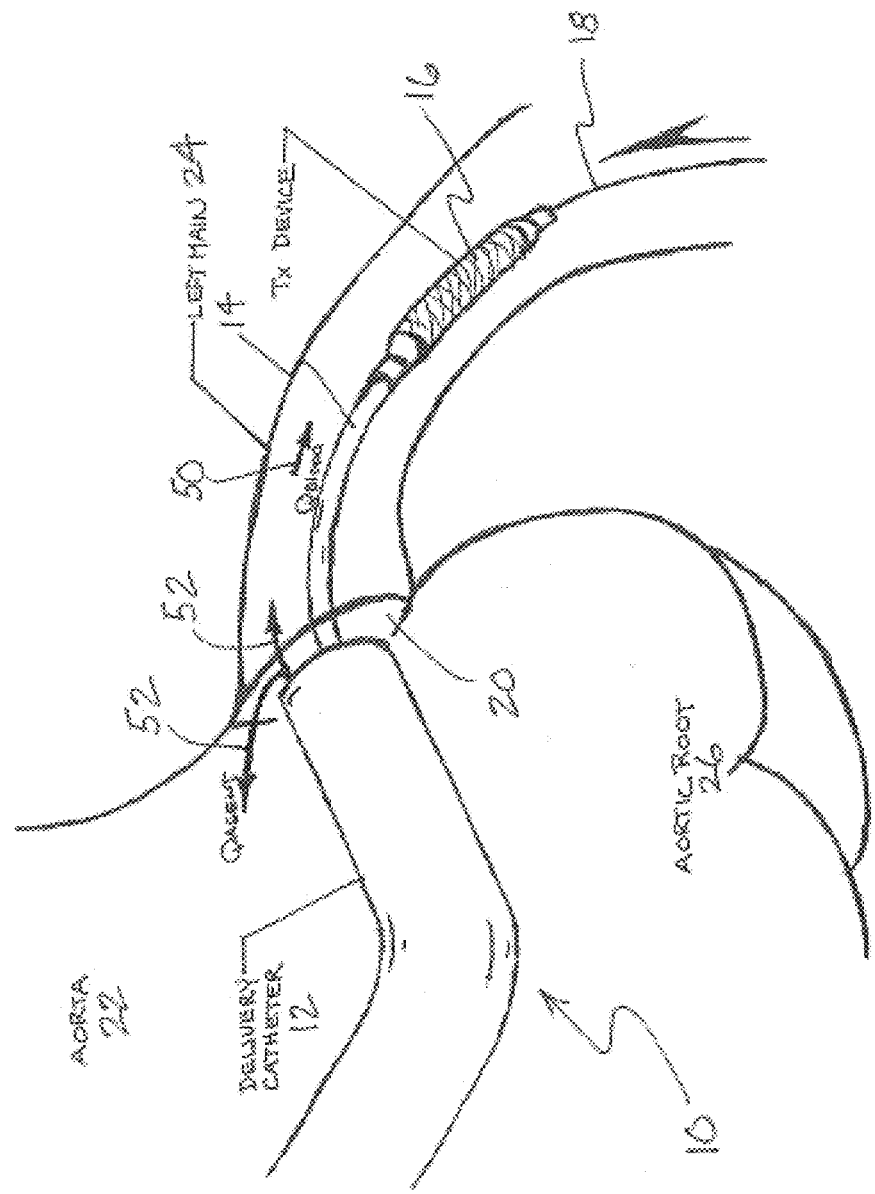

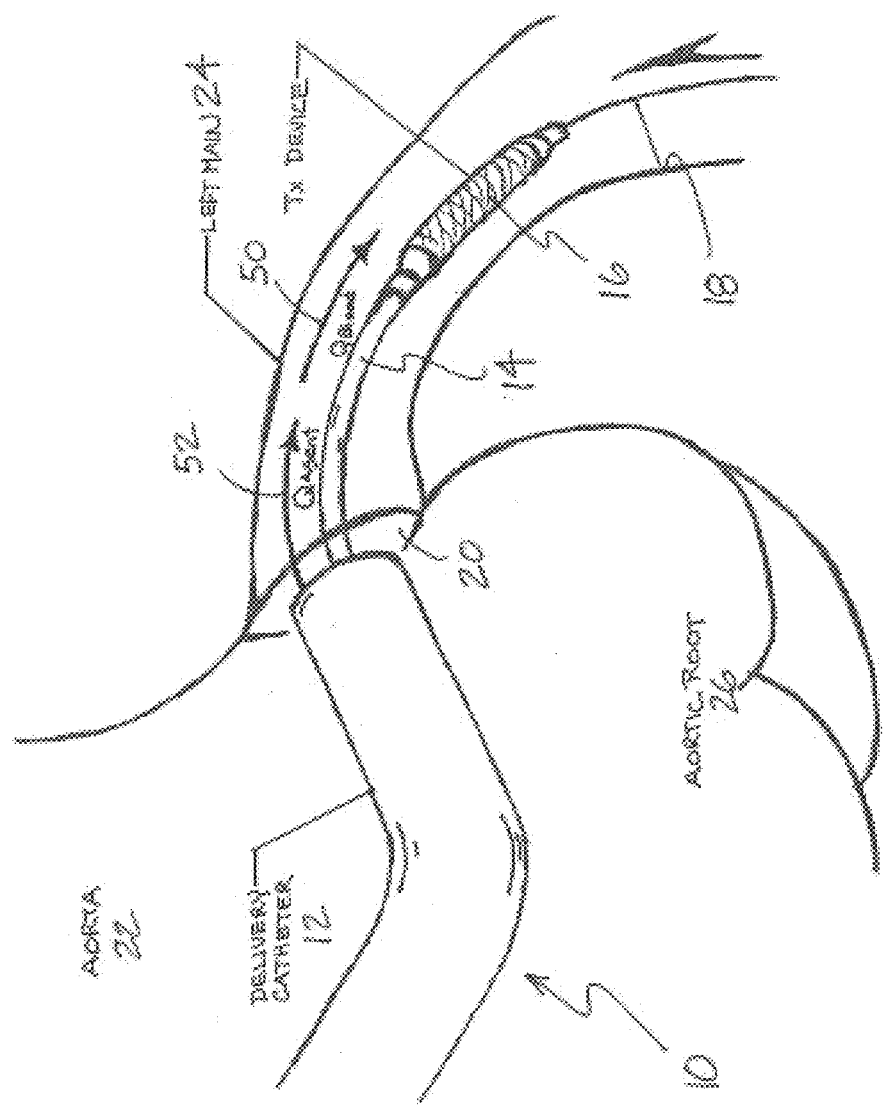

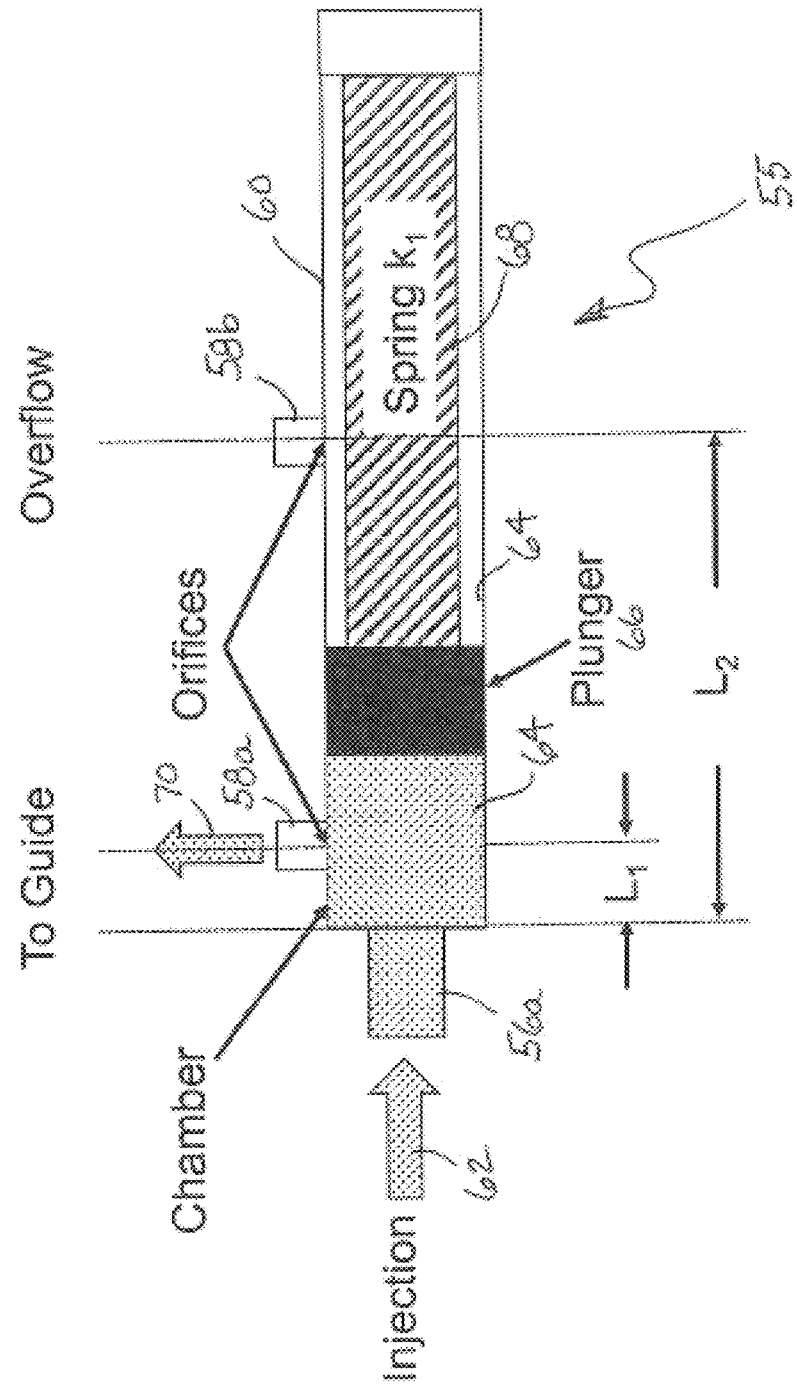

Exemplary Single Chamber Flow Modulator

Exemplary Single Chamber Flow Modulator in System of Figure 3C

Figure 7

Fluid Flow Equations (Laminar) in a Conduit $$Q \text{ (fluid flow)} = \frac{\Delta P}{\Sigma W_n}$$

Wherein: Q = flow of fluid through a conduit
$\Delta P$ = pressure differential of the conduit from entrance to outlet
$\Sigma W_n$ = summation of resistances along n sections of a conduit And, for a tubular conduit, each $W_n = \dfrac{8 * \mu * L_n}{\pi * R_n^{\,4} * z_n * c}$
(e.g., tubes are coaxial and flow is between), with:
$z = ((1-K_n^{\,4}) - (1-K_n^{\,2})^2/\text{Natural Log}(1/K_n))$
$K_n = r_n/R_n$
$r_n$ = outer diameter of inner tube of section n
$R_n$ = inner diameter of outer tube of section n Wherein: $\pi = \text{pi}$
$\mu$ = viscosity of the fluid
$R_n$ = the inner diameter of the conduit of section n
$L_n$ = the length of the conduit of section n
$z_n$ = flow correction factor for flow between two tubes of section n
c = empirically derived coefficient to correct for non-laminar flow (i.e., flow head development, transitions between sections n, pressure changes, etc.), dimensional variations (i.e., non-concentric, deformation), temperature variations (i.e., fluid viscosity), etc.

Exemplary Two-Chamber Flow Modulator

Exemplary Two-Chamber Flow Modulator

Exemplary Two-Chamber Flow Modulator

Exemplary Two-Chamber Flow Modulator with Holding Chamber

Exemplary Two-Chamber Flow Modulator with Holding Chamber

Exemplary Two-Chamber Flow Modulator with Holding Chamber

Capacitance Chamber Flow Modulator (Bladder)

Capacitance Chamber Flow Modulator (Bladder)

Exemplary Flow Modulator with Constant Force Chamber

Exemplary Flow Modulator with Constant Force Chamber

Exemplary Constant Flow Modulator

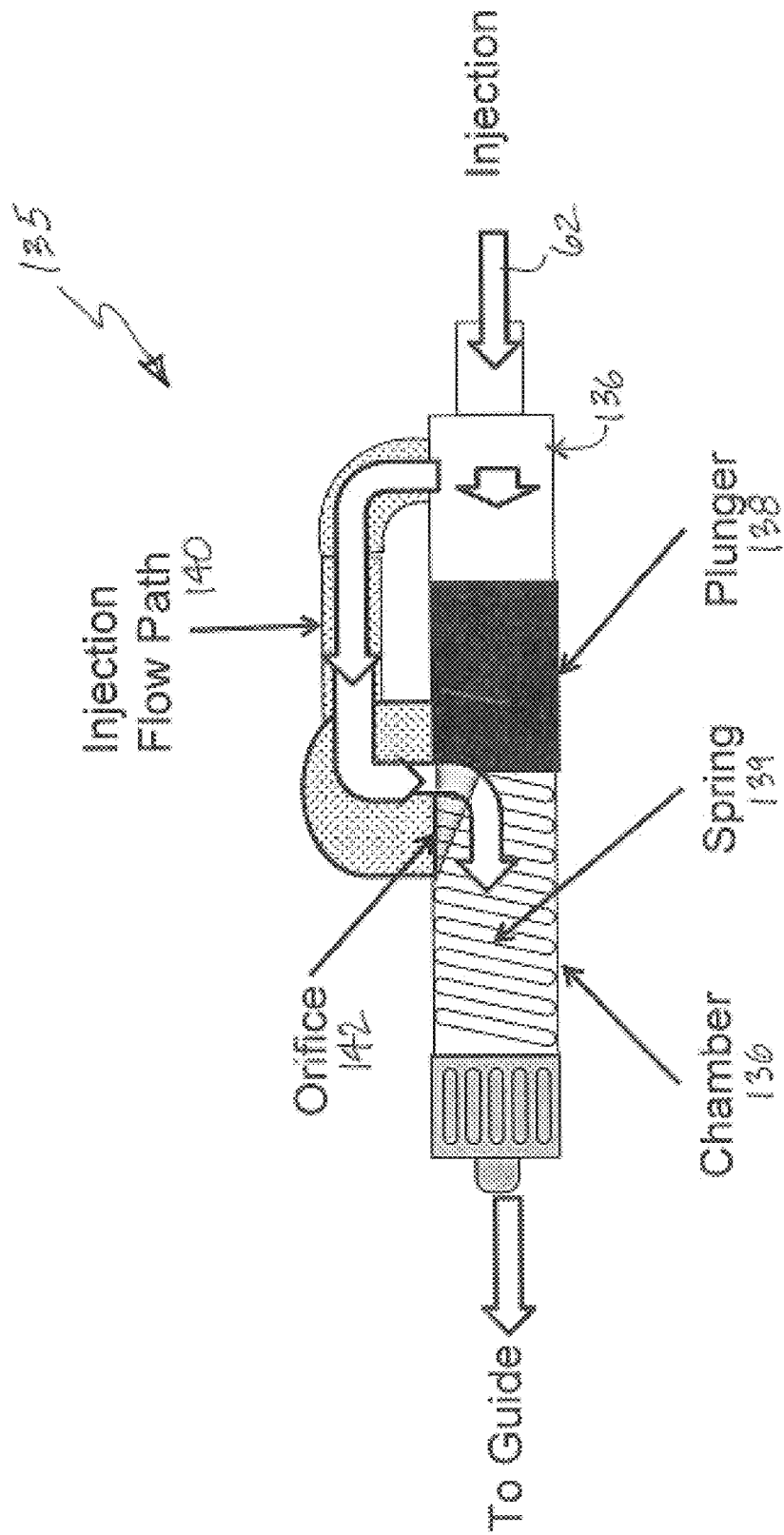

Exemplary Schemas of Synchronized Agent Delivery Modulation System

Exemplary Synchronized Agent Delivery with Direct Modulation

Exemplary Synchronized Agent Delivery with Indirect Modulation

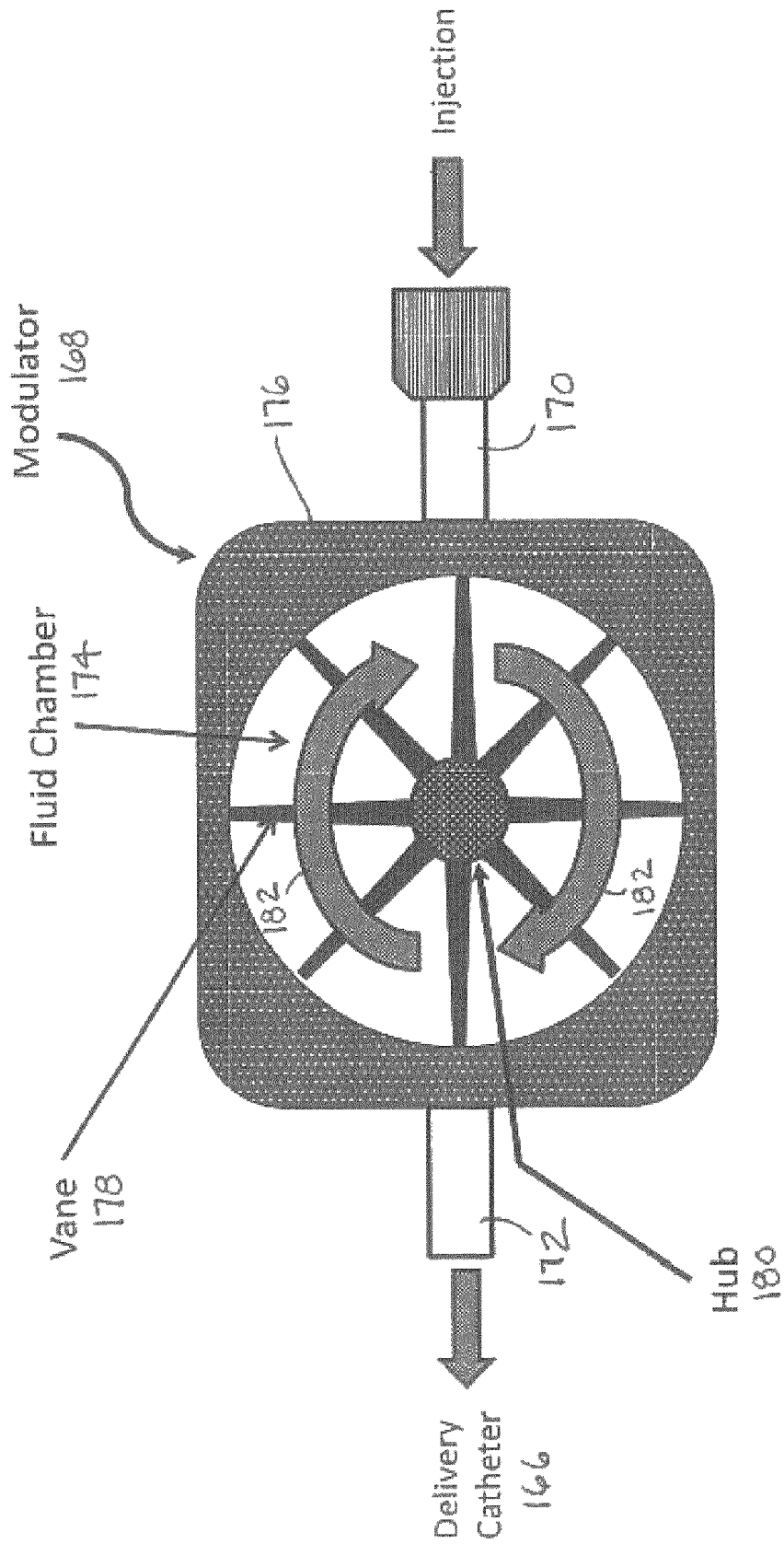

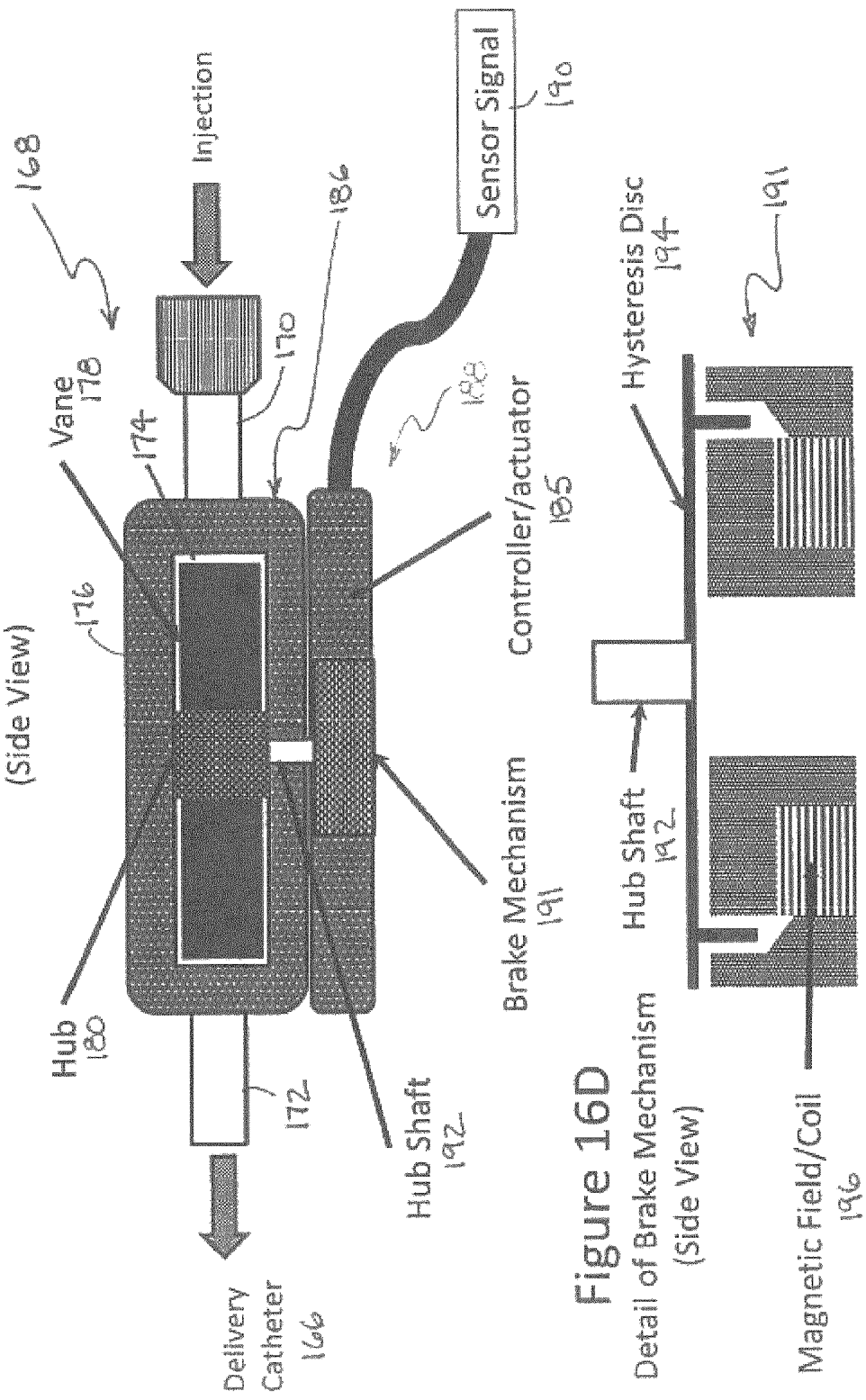

Figure 17
Exemplary Delivery Catheter Distal Constructions
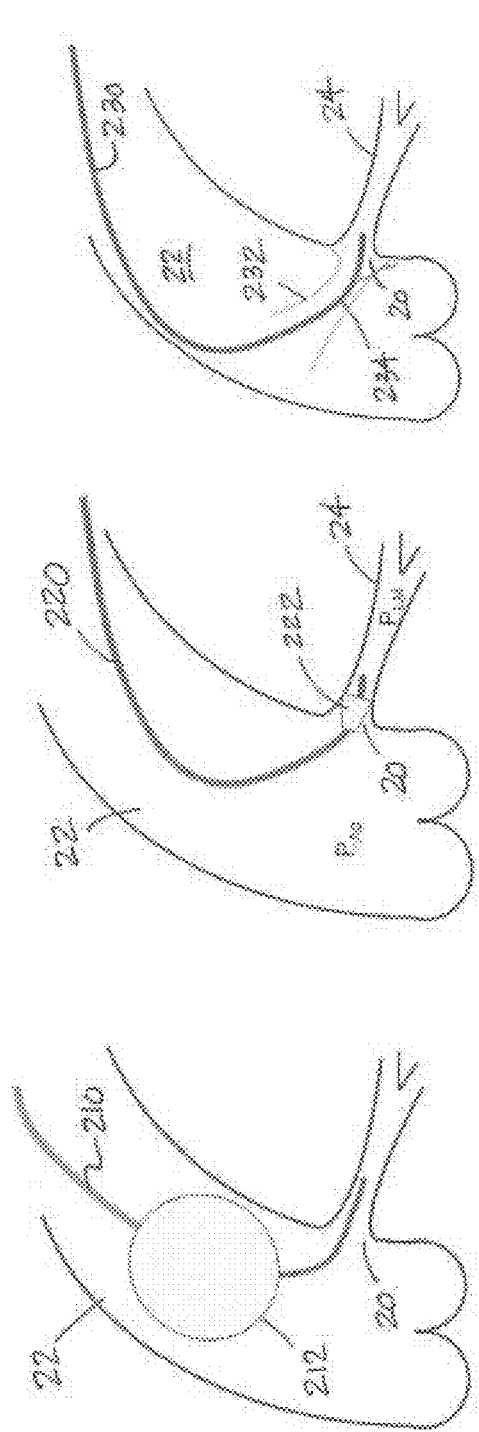
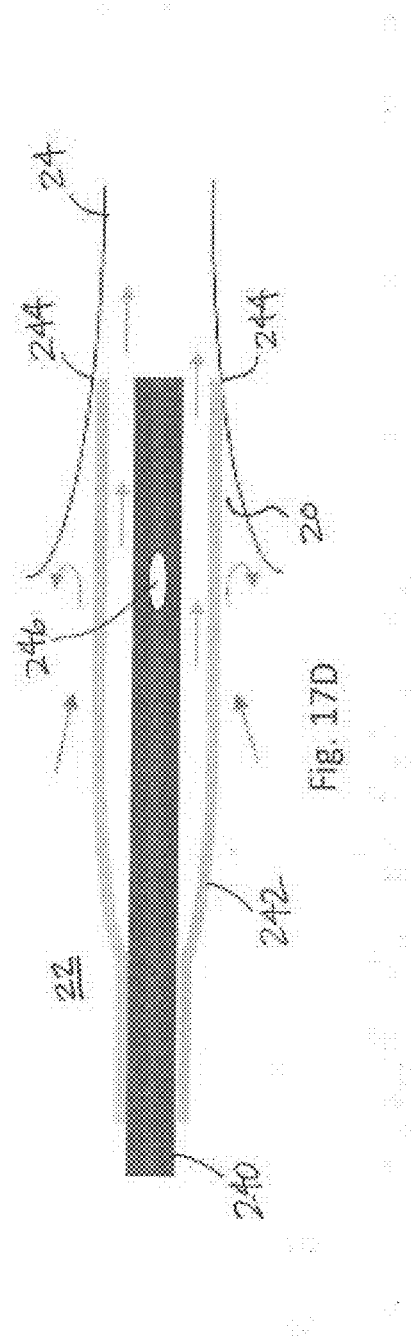
Fig. 17A
Fig. 17B
Fig. 17C
Fig. 17D

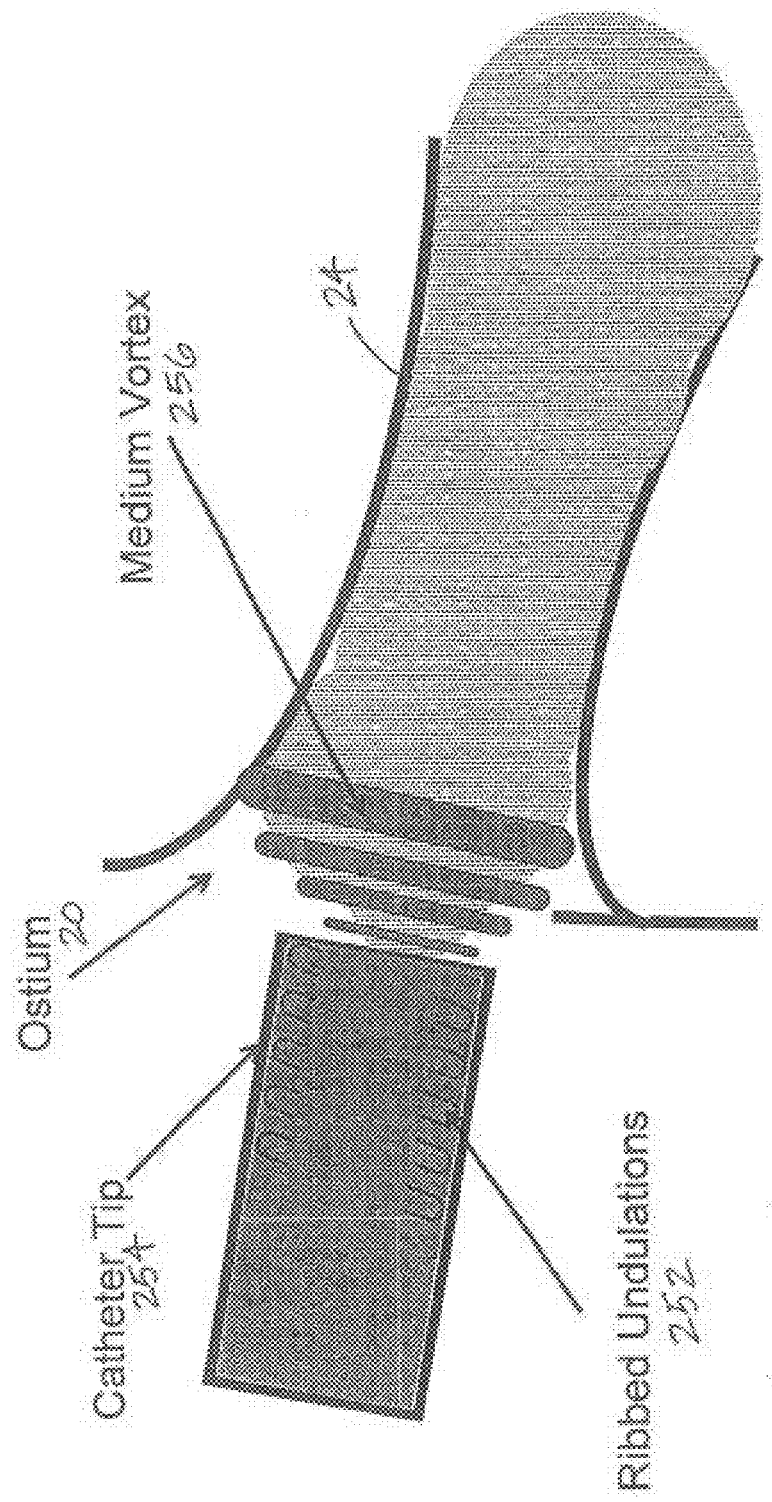

FIG. 19

Illustrative Media Delivery Modulation Elements/Functions with Exemplary References

| Elements/Functions | Illustrative Description | | |
|---|---|---|---|
| Injection Device Type | Automated/Power Injector FIG. 3C | Manual FIG. 3C | Gravity Fed In Description |
| Regulation Type | Constant Flow FIG. 12A - 12B | Pressure FIG. 6A - 6B | Flow Resistance Alteration FIG. 17B |
| Sequential Delivery or Direct Delivery | Sequential (Delayed) FIG. 10A - 10B | Direct (Non-sequential) Delivery FIG. 6A - 6B | |
| Synchronization with Corporeal Flow | Synchronized FIG. 13 | Non-synchronized FIG. 4C | |
| Flow Activation/Deactivation | Direct to Pump FIG. 14 | Indirect: Post-pump FIG. 14 | |
| Flow Distal Environ Alternation | Capture/Isolate/Modify FIG. 17A - 17B | Disruption FIG. 18 | |

Exemplary Constant Force Modulator – System Set-up

Exemplary Constant Force Modulator – Filling Injector

Exemplary Constant Force Modulator – Constant Force Chamber Open

Example: Medium Delivery with Left Main Pressure < Aortic Pressure

Example: Cessation of Medium Delivery with Left Main Pressure > Aortic Pressure

Valving at Catheter Distal Portion

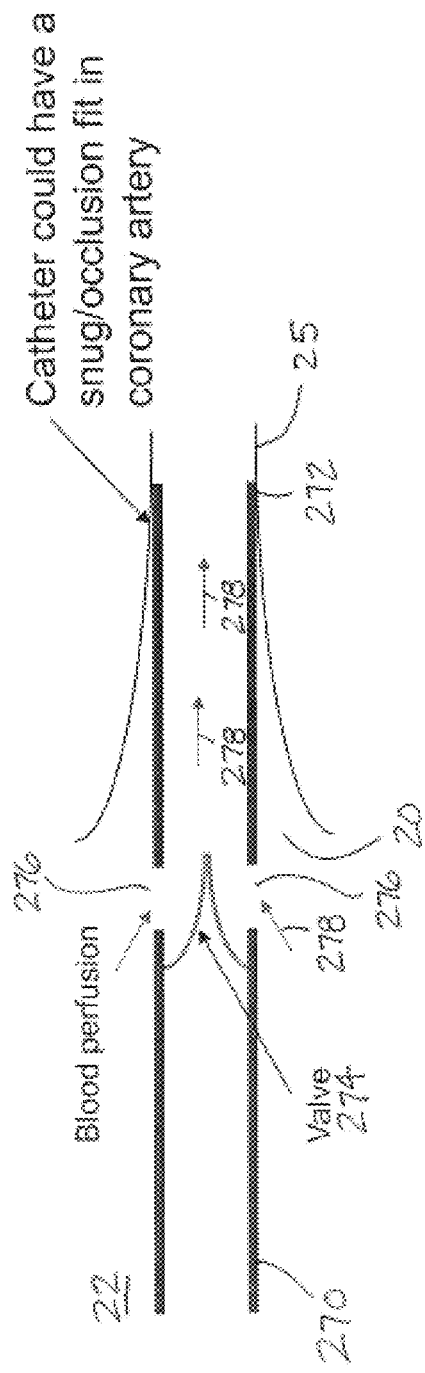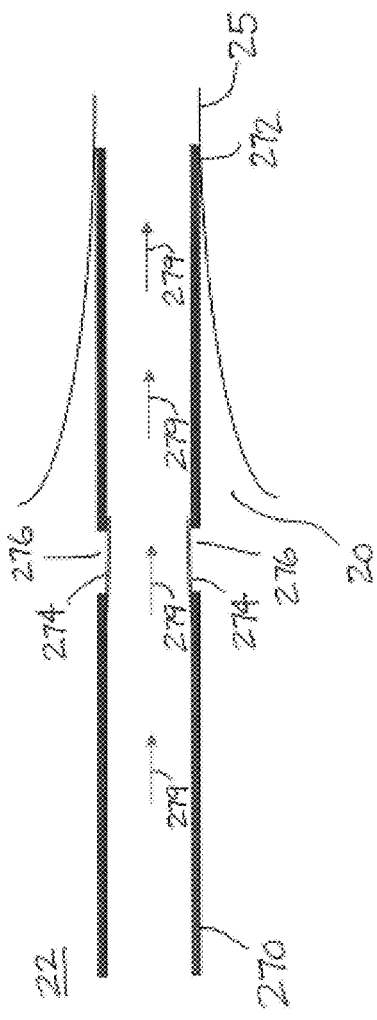

DEVICES AND METHODS FOR MODULATING MEDIUM DELIVERY

CROSS-REFERENCE TO RELATED APPLICATION(S)

This application relies, under 35 U.S.C. § 120, on the earlier filing date of prior U.S. patent application Ser. No. 14/660,410, filed on Mar. 17, 2015, which is a divisional of U.S. patent application Ser. No. 13/839,771, filed on Mar. 15, 2013, which is based on and claims the benefit of U.S. Provisional Patent Application No. 61/694,137, filed on Aug. 28, 2012.

This disclosure pertains to devices and methods used to control, transform or otherwise modulate the delivery of a substance, such as radiopaque contrast, to a delivery site. More specifically, it is the intention of the following devices and methods to modulate the delivery of media to a vessel, vascular bed, organ, or/and other corporeal structures so as optimize the delivery of media to the intended site, while reducing inadvertent introduction (or reflux) of the media to other vessels, vascular beds, organs, and/or other structures, including systemic introduction.

The terms medium (media), agent, substance, material, medicament, and the like, are used generically herein to describe a variety of fluidal materials that may comprise, at least in part, a substance used in the performance of a diagnostic, therapeutic or/and prophylactic medical procedure and such use is not intended to be limiting.

SUMMARY

This summary is provided to introduce a selection of concepts in a simplified form that are further described below in the Detailed Description. This summary is not intended to identify key features or essential features of the claimed subject matter, is not intended to describe each disclosed embodiment or every implementation of the claimed subject matter, and is not intended to be used as an aid in determining the scope of the claimed subject matter. Many other novel advantages, features, and relationships will become apparent as this description proceeds. The figures and the description that follow more particularly exemplify illustrative embodiments.

In one aspect, a system to control, regulate, alter, transform or otherwise modulate the fluid delivery of medium injected to a body site comprises an injector for injecting the medium, a delivery catheter comprising a conduit for delivering the medium from outside of the body to a delivery site within the body, and a modulator disposed between the injector and the delivery catheter. The modulator comprises a medium reservoir, the reservoir including a chamber for receiving medium therein and at least one surface within the chamber capable of imparting a constant force on medium within the chamber, and a manifold having a manifold lumen therethrough. The manifold lumen includes a first medium port fluidly coupled to the injector, a second medium port fluidly coupled to the chamber of the medium reservoir, and a third medium port fluidly coupled to the delivery catheter.

In another aspect, a system for the modulation of the fluid characteristics of a fluid medium to a delivery site within a body comprises a delivery catheter having a lumen and capable of delivering a medium from outside the body to the delivery site within the body, an injector capable of being activated to provide fluid medium to the delivery catheter, and a modulator disposed between the injector and the delivery catheter, wherein the modulator establishes, during the provision of the fluid medium to the delivery catheter, a pre-determined maximum pressure value for the fluid medium being provided to the delivery catheter.

In another aspect, a system for the modulation of pressure of a fluid medium comprises an injector for injecting the medium, a delivery catheter for delivering the medium from outside a body to a delivery site within the body, and a modulator disposed between the injector and the delivery catheter. The modulator comprises a medium chamber in fluid communication with the injector and the delivery catheter, wherein the chamber is capable of acting as a pressure capacitor for the medium, being charged in the first instance by medium flowing from the injector into the chamber, and discharged in the second instance by fluid flowing from the chamber into the delivery catheter or the injector, and wherein the chamber includes a surface therein that imparts a constant pressure force on medium within the chamber.

In another aspect, a method for controlling, regulating, altering, transforming or otherwise modulating the fluid delivery of medium to a selected site in a patient comprises establishing a desired flow rate through a delivery catheter for the fluid medium to be delivered at the selected site, and employing a modulating mechanism disposed between a medium injector and the delivery catheter. The modulating mechanism is capable of minimizing the time necessary to achieve the desired flow rate at the selected site, maintaining the desired flow rate at the selected site for a selected time interval, and minimizing the time necessary to stop the desired flow rate after the selected time interval.

In another aspect, a method for modulation of a fluid medium to a delivery catheter, wherein the delivery catheter is capable of delivering the medium from outside a patient to a site within the patient, comprises establishing a desired flow rate for the fluid medium within the catheter at the selected site, delivering fluid medium to the delivery catheter from a manual injector, and simultaneously delivering fluid medium to the delivery catheter from a constant force chamber. A first pressure force exerted on the fluid medium by the manual injector varies, and a second pressure force exerted on the fluid medium by the constant force chamber is constant at the predetermined value, where that value is a function of the desired flow rate.

In another aspect, a method for modulation of a fluid medium to a delivery catheter at a selected site in a patient comprises establishing a desired flow rate for the fluid medium within the catheter at the selected site, delivering fluid medium to the catheter from a manual injector, delivering fluid medium to the catheter from a constant force chamber, and preventing a pressure of fluid medium in the delivery catheter delivered from either the manual injector or the constant force chamber from exceeding a maximum pre-determined pressure.

BRIEF DESCRIPTION OF THE DRAWINGS

The disclosed subject matter will be further explained with reference to the attached figures, wherein like structure is referred to by like reference numerals throughout the several views.

FIG. 3A illustrates an exemplary coronary artery treatment system.

FIG. 4A illustrates graphically an exemplary injection profile (flow rate) of agent for the treatment system of FIG. 3.

FIG. 4B illustrates graphically an injection profile (flow rate) of agent for the treatment system of FIG. 3, identifying under-injection and over-injection volume areas of media for opacification purposes.

FIG. 4C illustrates graphically an exemplary improved constant injection profile (flow rate) of agent for achieving opacification.

FIG. 4D illustrates graphically the exemplary agent injection profile of FIG. 4A relative to the exemplary blood rate flow profile of FIG. 2.

FIG. 5A illustrates an exemplary flow of injection in the distal portion of the exemplary treatment system of FIG. 3B.

FIG. 5B illustrates an alternative exemplary flow of injection in the distal portion of the exemplary treatment system of FIG. 3B.

FIGS. 6A and 6B illustrate an exemplary single chamber flow modulator, in different stages of flow control.

FIG. 7 sets forth exemplary fluid flow equations (laminar) that may be used in modeling a conduit fluid flow.

FIGS. 12A and 12B illustrate an exemplary constant flow modulator, in different stages of flow control.

FIG. 16B illustrates an exemplary synchronized agent delivery with indirect modulation (top view), adjacent a proximal portion of such a treatment system.

FIG. 16C illustrates an exemplary synchronized agent delivery with indirect modulation (side view), adjacent a proximal portion of such a treatment system.

FIG. 16D illustrates, in side sectional view, the brake mechanism of the exemplary synchronized agent delivery arrangement of FIG. 16C.

FIGS. 17A, 17B, 17C and 17D illustrate exemplary delivery catheter distal constructions.

FIG. 18 illustrates an exemplary delivery catheter with distal disrupting structure.

FIG. 19 illustrates, in chart form, exemplary medium delivery modulation control factors and/or elements.

FIGS. 25A and 25B illustrate another exemplary arrangement for passive valve control of blood flow and medium flow adjacent a medium delivery site.

Figure 1:
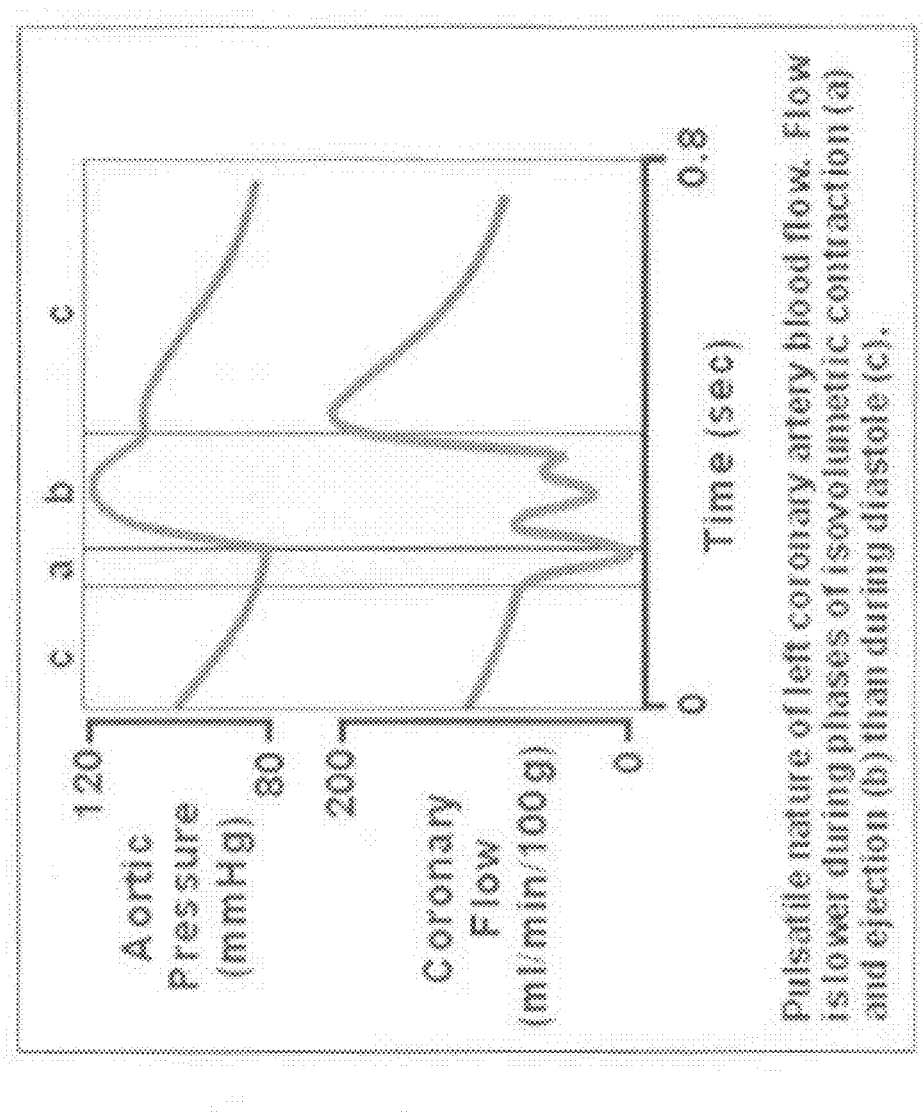
FIG. 1 illustrates in graphic form, the exemplary pulsatile nature of left coronary artery blood flow and blood pressure.

While the above-identified figures set forth one or more embodiments of the disclosed subject matter, other embodiments are also contemplated, as may be noted in the disclosure at times. In all cases, this disclosure presents the disclosed subject matter by way of representation and not limitation. It should be understood that numerous other modifications and embodiments can be devised by those skilled in the art which fall within the scope and spirit of the principles of this disclosure.

DETAILED DESCRIPTION

There are numerous occasions in the diagnostic, prophylactic and treatment practice of medicine wherein an agent, medicant, or medium is preferably delivered to a specific site within the body, as opposed to a more general, systemic introduction. One such exemplary occasion is the delivery of contrast media to coronary vasculature in the diagnosis (i.e., angiography) and treatment (i.e., balloon angioplasty and stenting) of coronary vascular disease. The description, as well as the inventive devices and methods described herein, may be used in modulating contrast media delivery to the coronary vasculature in prevention of toxic systemic effects of such an agent; although, one skilled in the art would recognize that there are many other applications wherein the controlled delivery of a media to a specific vessel/structure/organ/site of the body may also benefit from the devices and methods disclosed herein. For simplicity, these devices and methods may be described as they relate to contrast media delivery modulation. As such, they may be used in the prevention of Contrast Induced Nephropathy; however, it is not intended, nor should it be construed, so as to limit the use to this sole purpose. Exemplary other uses may include the delivery/injection/modulation of: cancer treatment agent to a tumor; thrombolytic to an occluded artery; occluding or sclerosing agent to a vascular malformation or diseased tissue; genetic agent to a muscular bed, neural cavity or organ; emulsion to the eye; bulking agent to musculature and/or sphincter; imaging agent to the lymphatic system; anti-biotics to an infected tissue; supplements in the dialysis of the kidney; to name but a few.

Exemplary Use—Prevention of Contrast Induced Nephropathy

Contrast Induced Nephropathy (CIN) is a form of kidney damage caused by the toxic effects of dyes (radiopaque contrast media) used, for example, by cardiologists to image the heart and its blood vessels during commonly performed heart procedures, such as angiography, angioplasty, and stenting. In general, the dye is toxic and is known to damage kidneys. Although most healthy patients tolerate some amount of the "toxicity," patients with poor or non-functioning kidneys may suffer from rapidly declining health, poor quality of life, and significantly shortened life expectancy. Potential consequences of CIN include: irreversible damage to the kidneys; longer hospital stays; increased risk of heart disease; increased risk of long-term dialysis; and, ultimately a higher mortality risk. For patients who acquire CIN, their risk of dying remains higher than others without CIN, and this risk continues even after five years of their procedure. CIN has a significant economic burden on the healthcare system and currently there is no treatment available to reverse or improve damage to the kidneys, once a patient develops CIN.

To date, there have been attempts in reducing the toxic effects of contrast media on patients who undergo procedures involving dyes, especially those patients who are at high risk for developing CIN. Some of these efforts have been to: change the inherent toxicity (chemical/molecular nature) of the dyes; reduce the total amount of contrast agent injected (through injection management and/or dye concentration); remove media through coronary vasculature isolation and blood/contrast agent collection systems, to name a few. These methods and/or devices used in the control of the toxic effects of contrast agents have had their inherent compromises in effectively delivering a contrast media specifically to a target site while minimizing the systemic effects. As an example, changing the composition of a dye and/or injection concentration may help reduce a contrast agent's inherent toxicity at the expense of the contrast agent's ability to perform its intended function (e.g., visualization of vasculature). Conversely, the ability to "collect" contrast agent laden blood "downstream" from the visualization site may ensure visualization, but requires the complexity of placement and operation of a collection system.

Other attempts to manage the amount of contrast agent delivered to a patient have employed automated (versus manual, syringe injected) contrast media injection systems. Close monitoring and control of the total quantity of contrast agent injected may have a positive impact in the incidence of CIN. However, these injection systems are expensive (including capital equipment and disposables), cumbersome to use within a cath lab, and take additional time and expertise to set-up and operate properly. Improper use could negate any benefits seen by better management of the quantity of the contrast agent delivered to a patient, and the additional time required to set-up such a system may also add significant complexity to a procedure.

Exemplary Use—Coronary Blood Flow and Management of Agent Delivery

Many of the vascular structures and capillary beds of the human body perfuse with enriched, oxygenated blood as a result of the blood being pressurized by the cyclical driving force of the heart during contraction (systole) and decompression (diastole). Most vascular blood flows peak in the body in response to the heart's contractile phase. Because of the cyclical flow of blood in the vasculature, optimization of delivery of any contrast agent to a vascular delivery site may be enhanced through the coordination of an injection's pressure and flow to coincide more closely with that of the vascular site receiving the contrast agent.

Although similar flow principals may apply, the flow of coronary blood is unique in that the perfusion of the heart coronary arteries principally peak during the diastolic (relaxation) phase of the ventricular cycle. As seen in FIG. 1, the pressure of blood in the aorta (from the heart) peaks during ejection (b). However, the flow of blood into the coronary arteries (left coronary artery/left main, as an example) actually peaks after this, during the relaxation/decompression of the heart (i.e., during diastole (c)). Thus, blood flow through the coronary vasculature, in a normal functioning heart, peaks when aortic blood pressure has diminished. This phenomenon appears contra to what one would expect for arterial heart vessel filling. The flow of blood through the coronary vasculature is not necessarily, or completely, "driven" by a high pressure gradient in the aorta into the coronary arteries. In fact, normally the filling of the coronary arteries peaks when the pressure in the aorta is substantially lower than the peak systolic pressure.

It is believed that this phenomenon is derived from a backward travelling, "driving force" or "suction" force of blood that is generated by the relaxing of the myocardium (as well as myocardial microvasculature) during diastole—in essence, during the decompression of the heart. The decompression of the heart in diastole results in a driving wave caused by the relief of the myocardial compression. This force is actually created through a pressure gradient wherein the low pressure of the aorta is actually higher than the vacuum created in the coronary capillary beds—thus, a gradient created from the aorta to the microvasculature. Further description of this phenomenon may be found, for example, in "Evidence of a Dominant Backward-Propagating 'Suction' Wave Responsible for Diastolic Coronary Filling in Humans, Attenuated in Left Ventricular Hypertrophy" (Circulation. 2006; 113:1768-1778), which is incorporated by reference in its entirety herein.

A challenge in the delivery of contrast agent to the coronary arteries is the cyclical nature of the flow in the arteries (quantity and rate). As further seen in FIG. 1, the pulsatile blood in the arteries may change significantly in flow rate over a single cycle of the heart. In addition, the variation in flow rate transpires over a very short period of time—in many cases, this takes place in less than a second.

Figure 2:
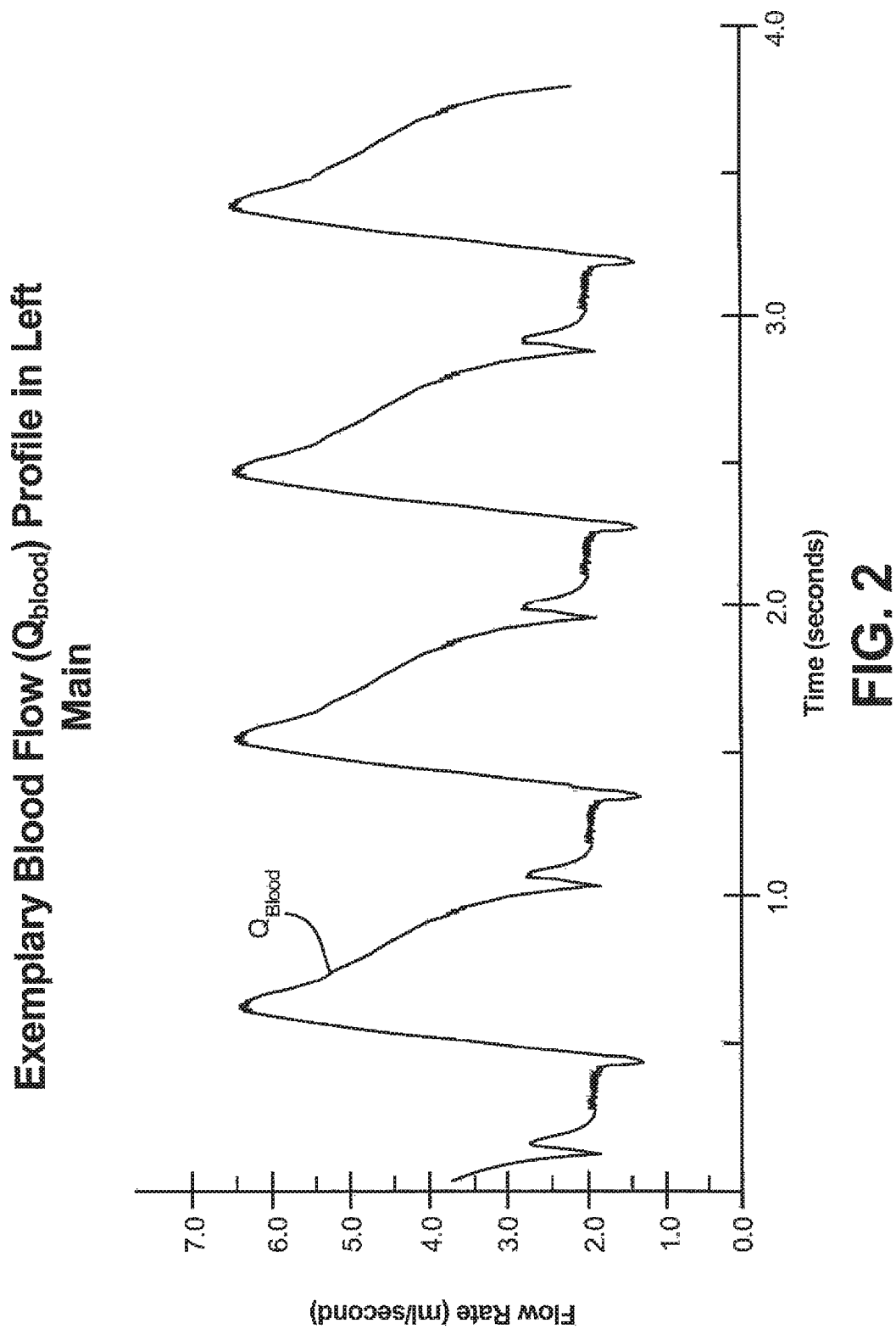
FIG. 2 is a graphic representation of an exemplary blood flow rate profile for a left main coronary artery.

FIG. 2 illustrates an example of a blood flow pattern that may be found within a left main coronary artery of a human heart. The illustrated profile of blood flow rate ($Q_{Blood}$, or blood volume flow rate) represents about four cycles of the heart over a period of time that is less than four seconds. The average flow rate of blood (e.g., mean $Q_{Blood}$) in this example averages about 3.7 ml/sec over a single cycle of the heart, and may vary significantly during each cycle from about 1.3 ml/sec to about 6.5 ml/sec. In this example, the left main is approximately 4.4 mm diametrically and has a length about 5 mm before it bifurcates into the left anterior descending artery and the left circumflex artery. It should be noted that this is only an example and any physiological, anatomical, or fluid flow characteristics described may vary significantly between patients, as well as within the same patient. These variations may occur as a function of age, vascular and/or coronary disease, vascularity and collateralization of the heart, metabolism, blood pressure, patient activity, stress level, functional status of various patients' organs, patient weight, vasodilatory and/or constrictive medicants, and chemical or biochemical mediators, to name but a few of the involved variables. Therefore, the example is intended to help elucidate the disclosure of the devices and methods herein, and is not intended to limit their use.

In further illustrating the inventive devices and methods herein, an example of a use of the system will involve the delivery of contrast agent to the left arterial system of the heart during the performance of a treatment procedure (e.g., stent delivery). However, this exemplary use should not, in any way, limit the use of the devices and methods described.

Figure 3B:
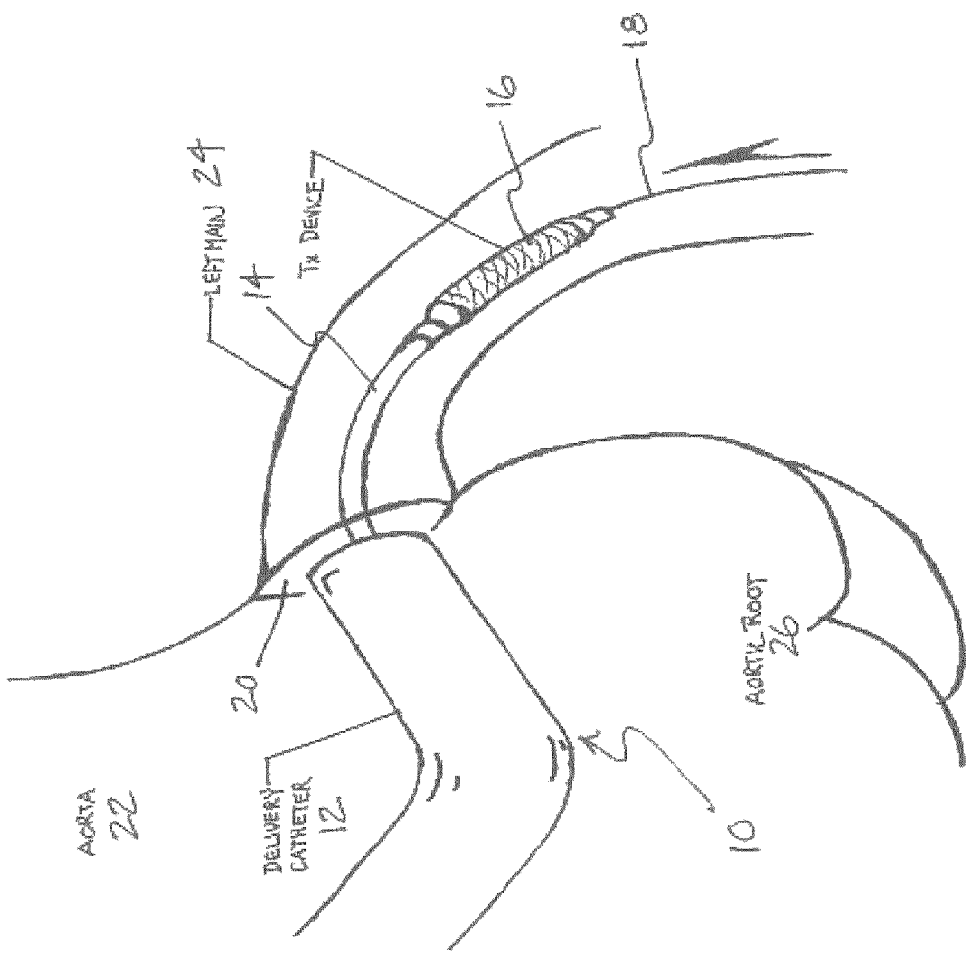
FIG. 3B illustrates a distal portion of the exemplary treatment of FIG. 3A.
Figure 3C:
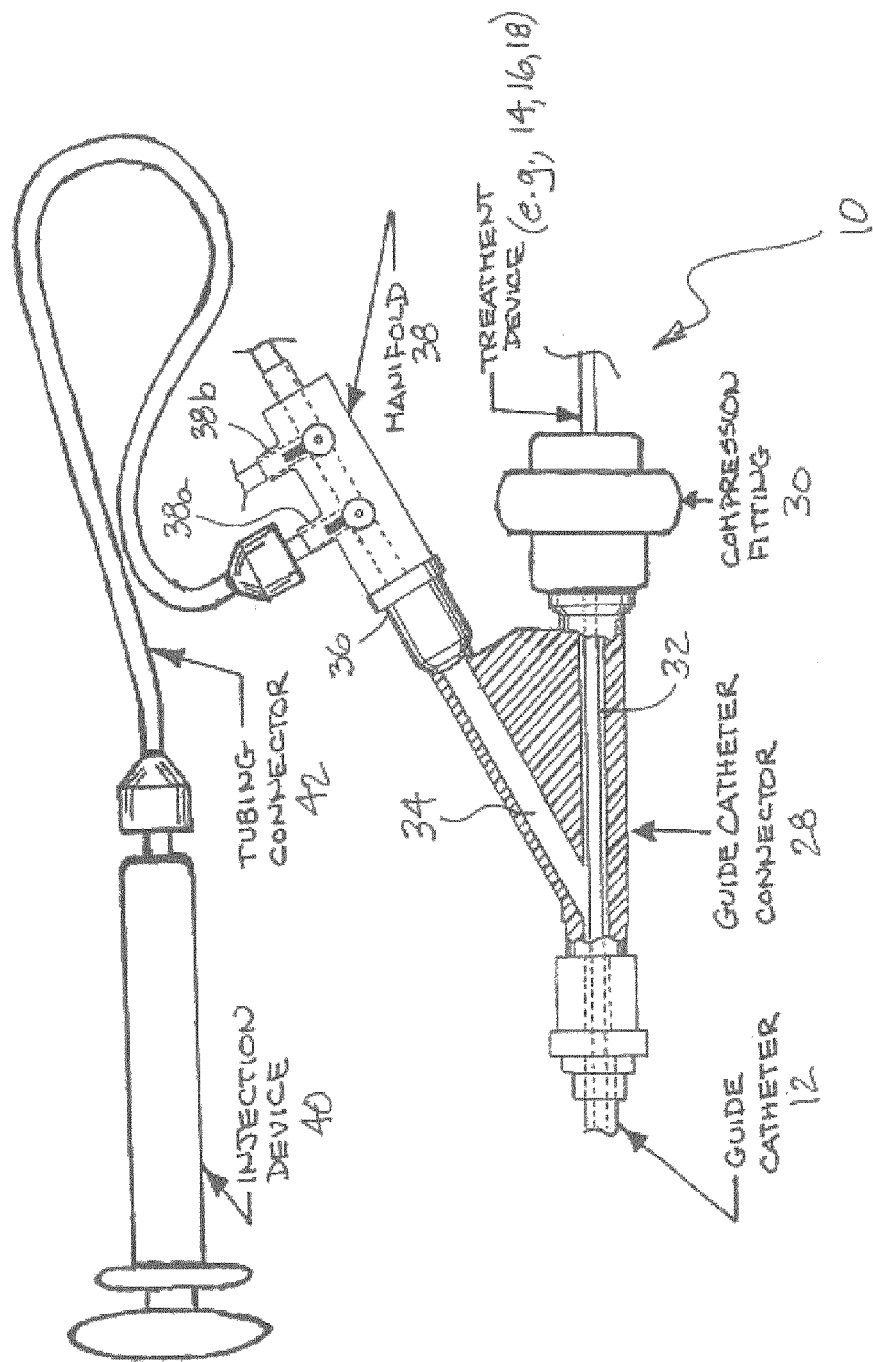
FIG. 3C illustrates a proximal portion of the exemplary treatment system of FIG. 3A.

Referring to FIG. 3A, a catheter, therapy, or treatment system 10 is shown that may be used in the treatment of an occlusion in a coronary vessel. FIG. 3B further highlights the distal portion of the catheter system, proximate a left coronary artery ostium. As seen in FIG. 3B, the system 10 includes a system delivery catheter 12 (e.g., guide catheter) and occlusion treatment devices (e.g., balloon catheter 14 with stent 16 and guide wire 18). The distal end of the guide catheter 12 is placed proximate an opening 20 (ostium) of the aorta 22 to the left coronary artery 24 (left main), off of the aortic root 26. The system 10 may be placed by percutaneous advancement of the system 10 from the femoral artery (not shown) to the aortic root 26. FIG. 3C further illustrates a proximal portion of such an arterial occlusion treatment system 10 (including a balloon catheter with stent, guide wire, connectors, etc.) shown in FIGS. 3A and 3B. Typically, there is a guide catheter connector 28 that may have a Tuoy-Borst compression fitting 30 attached to a proximal portion of the connector 28. The treatment devices may be passed axially through an outlet of the connector 30 and into a primary lumen 32 of the connector 28, and then into the guide catheter 12. The fitting 30 of the connector 28 may be adjusted so as to allow passage of the treatment devices through connector 28, but resist back flow of fluid out of the guide catheter 12 and connector 28. In addition, the connector 28 may have a secondary lumen 34 displaced laterally of, and in communication with, primary lumen 32. Secondary lumen 34 may terminate in luer-fitting 36. A manifold assembly 38 with multiple ports (e.g., ports 38a, 38b) may be attached to luer fitting 36. These additional ports of the manifold 38 may be used to infuse various media through the guide catheter 12 (e.g., within a flow conduit defined by an inner lumen of the guide catheter, and the outer proximities of any treatment system components 14, 16, 18 therein). Such infusions may include, for example, radiopaque contrast, medicaments, or saline for flushing the guide catheter 12.

The treatment system 10 described in FIGS. 3A-3C may be comprised of components that may be used in such a procedure, such as a 6 F guide catheter having an approximate length of 100 cm and an inner diameter of approximately 0.070 inch. Further, the treatment devices (e.g., balloon catheter, stent, guide wire, etc.) might have an outer diameter of 3.2 F proximally and 2.7 F distally. The delivery of the treatment devices may be accomplished by passing the balloon catheter through the guide catheter and over a guide wire of 0.014 inch in diameter. The injection of contrast agent for the visual assessment of the vasculature may be performed by activating an injection device 40 (such as an injector or syringe), as seen in FIG. 3C. In this case, the contrast agent may pass from the injection device 40, through a tubing connector 42 (i.e., between injection device 40 and manifold 38), the manifold 38, the guide catheter connector 28, and ultimately through the co-axial conduit defined between the guide catheter inner diameter and the treatment catheter system (e.g., balloon catheter) outer diameter.

This example is illustrative of a treatment procedure and should not be limited to the various assemblies that may be deployed for any given procedure, or by any specific physician. The various infusions of the given example may be introduced through the manifold connections by numerous means, to include manual injection (i.e., syringe), automatic injection with an injection machine, or a "gravity fed" injection arrangement. How perfusions/infusions of various substances may be administered may depend on the medium and the intended therapy. In FIG. 3C, a syringe is shown connected to the manifold with a tubing connector, providing means to hand-inject contrast medium through the manifold and to the distal outlet of the guide catheter. Conversely, a power injector may be attached to the manifold to perform the injection, as an alternative configuration.

Moreover, the example described is illustrative of a treatment procedure comprising a "guide catheter" in conjunction with a treatment system. However, there are a multitude of constructions of conduits that may be capable of delivering, or otherwise mediating the delivery, of substance from a proximal portion of a system (outside of a body) to an intended corporeal site. And thus, reference to a "guide catheter" or "catheter" in the example could be described as a tube, delivery catheter, or any other conduit used in mediating the delivery of a substance; and as such, should not be limited to the various assemblies for the exemplary procedure.

FIG. 4A illustrates an exemplary hand-injection flow rate profile ($Q_{Agent}$) of contrast media that may be delivered through a catheter treatment system such as described above. In the example of FIG. 4A, flow rate ($Q_{Agent}$) is described. However, it should be apparent to those skilled in the art that a pressure profile could have been used to describe the concepts herein since there is a direct relationship between the flow rate (Q) and the pressure drop (dP or $\Delta P$) over a conduit.

In the example of FIG. 4A, an injection profile of $Q_{Agent}$, as delivered to the distal tip of the guide catheter, represents approximately 10-12 ml of contrast media injected over approximately 3-4 seconds. This may be a fairly typical hand-injection for illuminating the left coronary vasculature over 2 to 5 cycles of the heart (while performing a stenting procedure); although, such injections may vary significantly (e.g., from 3 ml to 30 ml over periods of 1 to 8 seconds). It should be noted that some clinical investigators (and injector manufacturers) have suggested using around 5 ml/second flow rate of agent ($Q_{Agent}$) for a left heart injection. However, these recommendations may have been derived solely on the optimization of vessel opacification, with little regard for over-use of contrast media. Over-injection may result in unnecessary delivery of contrast media systemically. It is the objective of at least some of the embodiments herein to modulate systemic contrast induction, and therefore minimize "over-injection" (injection that is greater than necessary for the contrast agent to effectively perform its opacification function).

In a coronary angiography procedure, a hand-injection is normally administered with increasing pressure, and thus volume, until contrast media is "seen" filling the coronary vasculature radiographically. At this point, the administration continues for about 3 seconds until the quantity of contrast media (e.g., approximately 10 ml) within the injector is used. For an automatic injector, typically the pressure or volume may be set (e.g., 5 ml/sec) and then the operator may activate the automatic injector with a hand-held actuator for several cycles of the heart.

The exemplary injection profile $Q_{Agent}$ shown in FIG. 4A reveals an increasing injection (flow rate, which is directly related to pressure). $V_i$ on the graph of FIG. 4A represents a minimum level of injection flow rate that may be necessary for the operator to "see" vascularity as a result of visualizing the contrast medium. In essence, $V_i$ is an injection rate of media that may be delivered to a vessel, or organ, wherein $V_i$ is a level known, or believed to be, an acceptable concentration of the substance to provide its intended function. In this case, $V_i$ is the level of delivery wherein the concentration of contrast media injected to the left main is of sufficient quantity to opacify the vasculature, on the average, over several cycles of the heart. $V_i$, as shown in this example, is approximately 3.0 ml/second. That is to say, with an injection of a constant 3.0 ml/second of contrast media the operator may effectively visualize the vasculature, while not over-injecting contrast media. In this exemplary context, an injection meaningfully less than $V_i$ will not provide adequate opacification. The exemplary injection of profile $Q_{Agent}$ in FIG. 4A results in a total volume of approximately 11 ml of contrast media delivered.

Referring to FIG. 4B, various areas are shown which may have (by definition of $V_i$) injection flows that are either insufficient to opacify the vessel appropriately (areas A and B), or are of a magnitude greater than is necessary for opacification, and may thus result in the over-delivering of contrast agent (area C). That is to say, if the injection had been controlled in the delivery of the contrast agent to obtain $V_i$ (identified as a rectangle within the injection rate profile $Q_{Agent}$ of FIG. 4B), approximately 3 ml less of contrast (25% to 30%) might have been used to achieve the same result (e.g., to sufficiently visualize the artery over the same period of time). Therefore, an injection flow rate profile $Q_{Improved}$ shown in FIG. 4C may outline an "improved" constant flow rate of injection for $V_i$ (i.e., wherein the injection flow rate may be held at a constant rate sufficient for visualization).

As a practical matter, and in further illustration of the complexity in efficiently delivering contrast agent into the dynamic environment of a coronary artery, some operators of the injector (a syringe, for example) may try to mimic a rapid injection so as to minimize the area of A in FIG. 4B through a rapid increase of pressure (and commensurate volume flow rate) with an injection. When sufficient opacification is "seen" radiographically, the operator may then decrease the pressure (and volume flow rate) of the injection. This technique may be helpful in reducing the area of A (quickly reaching $V_i$); however, the operator may "overshoot" the delivery rate required to the vessel for opacification (i.e., $V_i$) and thus increase the amount of over-injection which may be seen by area C in FIG. 4B. It should be noted that a 10 cc (ml) syringe may be capable of injecting at 100 psi or more. This pressure of injection from the syringe could generate flows as high as 4.0 ml/second in the exemplary system described above; whereas, only 75 to 85 psi may be needed to inject 3.0 ml/second, as an example.

FIG. 4D illustrates the exemplary flow of blood in the left main (e.g., left main 24 of FIG. 2), noted as blood flow rate profile $Q_{Blood}$ super-imposed with an exemplary profile of an injection flow rate of contrast (e.g., profile $Q_{Agent}$ of FIGS. 4A and 4B) over-laying the blood flow pattern. In this example, we have additionally assumed that the start of the injection begins at about the same time as systole (compression of the heart with lower blood flow rates). However, from a practical point of view, timing of the beginning of an injection may happen at any time during the heart cycle since it may be difficult to synchronize injections with the vessel blood flow. As can be seen in FIG. 4D, an injection at a constant $V_i$ flow rate (or, as described by $Q_{Improved}$ in FIG. 4C), although notably better than no modulation (e.g., $Q_{Agent}$) may still result in over-injecting contrast media (at times) since the blood flow rate (e.g., $Q_{Blood}$) is less than the rate of injection (e.g., $V_i$ or $Q_{Improved}$). In this case, the areas D in FIG. 4D may indicate such over-injection, where contrast may be injected into the aorta (as an example) rather than into the left main artery.

In describing this example further, the arrows in FIGS. 5A and 5B illustrate flows $Q_{Blood}$ (arrow 50) and $Q_{Agent}$ (arrows 52) during injection of contrast agent during different phases of the heart cycle. When the injection of contrast medium is greater than the blood flow in the vessel 24 (FIG. 5A) there will be a tendency for the contrast media to flow to the least path of resistance. In this case, some of the contrast media may flow to the aorta 22 and, consequently, systemically. Conversely, when the blood flow ($Q_{blood}$) in the vessel is greater than the injection flow ($Q_{Agent}$), the flow of contrast media may preferentially pass into the vessel 24 (FIG. 5B). In other words, the injection flow rate ($Q_{Agent}$) illustrated by arrow 52 in FIG. 5B will follow the blood flow rate ($Q_{blood}$) illustrated by arrow 50.

Various embodiments of the inventive devices and methods will now be described in further detail. Many of these embodiments may control, transform or otherwise modulate a pattern of medium, agent, substance, medicament, or fluidal material delivery to a vessel, vascular bed, organ, or/and other corporeal structures so as optimize the delivery of media to the intended site, while reducing inadvertent introduction (or reflux) of the media to other vessels, vascular beds, organs, and/or other structures, including systemic introduction. Some of these embodiments may modulate an injection, such as the example shown in FIG. 4A, by controlling the flow rate profile of an injection to attain a profile designed to reduce inefficient agent use (e.g., areas A, B and/or C in exemplary injection profile $Q_{Agent}$ of FIG. 4B), and to obtain an "improved" injection profile $Q_{Improved}$ in FIG. 4C.

Exemplary Modulation Devices and Methods

Some of the "modulators" in the following examples may be located at various locations proximate the proximal portion of the therapy system 10, as described in FIGS. 3A-3C. For example, a modulation controlling mechanism may be positioned on the injection device outlet, between the injector 40 and the manifold 38, between the manifold 38 and the guide connector 28, as well as between the guide connector 28 and the guide catheter 12. Some other embodiments may also include directly controlling the performance of the injection device 40. The placement of the modulator may also be highly dependent on the diagnostic, prophylactic or therapeutic procedure to be performed and, as such, the positioning should not be limited by the examples used herein.

In addition to locations described above, some inventive embodiments of fluid modulators may alternatively be positioned in, and/or around, and/or proximate the distal portion of the guide catheter/delivery catheter 12.

Furthermore, some embodiments of control devices disclosed herein may advantageously receive a sensor signal so as to coordinate a valving, controlling, or otherwise modulating function on an injection agent before the agent enters an intended target injection site.

One exemplary embodiment of a modulation device 55 is shown in FIG. 6A. Device 55 may be positioned within the exemplary system 10 of FIG. 3C, as shown in FIG. 6C. As such, an "injection" port 56a of modulator 55 has a connector 56 coupled by tubing 42a to injection device 40, and an outlet port 58a of the modulator 55 has a connector 58 coupled by tubing 42b to manifold 38. FIG. 6A shows the exemplary modulator 55 comprising a body 60 having three ports thereon. One of these ports (the "Injection" port 56a) receives an injection of agent from injection device 40. A "To Guide" port (outlet port 58a) delivers agent from device 55 to the manifold 38, and subsequently through the guide 12. An "Overflow" port (outlet port 58b) is activated upon over pressurization by the injector 40 to the modulator 55, so as to release excessive agent out of the system 10 (i.e., out of device 55).

An example of how such a modulator may function may be determined by the injection parameters (i.e., pressure, volume, flow rate, etc.) intended to improve the delivery of the agent. For example, $V_i$ of FIG. 4 (with the exemplary treatment system use as described for and by FIG. 3) may be approximately 3.0 ml/second. Using various flow equations for flow within a conduit (assuming some amount of laminar flow), such as those shown in FIG. 7, an injection pressure level (from the injector, for example) may be derived to provide an agent flow rate delivered from the distal end of the guide catheter. With a set-up and dimensions as described, a pressure of 75 psi (at or around the proximal portion of the guide catheter) may sufficiently produce about 3.0 ml/second of $Q_{Agent}$ delivered to the distal tip of the guide catheter positioned at the ostium to the left main. This example is intended to be illustrative for the purpose of description and, as such, should not be restrictive or limiting in the scope of the devices and methods described and disclosed herein. For example, if the treatment device (e.g., balloon catheter 14, stent 16, and wire 18) described above were to have a different construction (than previously described), such as a proximal and a distal outer dimension of 2.7 F, only 43 psi may be necessary to produce approximately 3.0 ml/second of $Q_{Agent}$. Alternatively, utilizing a guide catheter (e.g., delivery catheter 12) with different inner diameter dimensions might be used in producing a medium flow rate of about 3.0 ml/second, at a lower pressure differential. For example, the guide catheter could be larger (0.076 inch inner diameter/6.5 F outer diameter) in corporeal areas less critical in the performance of the treatment (e.g., descending aorta), while providing advantages of a smaller treatment system (e.g., guide catheter having 0.70 inch inner diameter/6 F outer diameter) in proximity of the treatment region (for example, 30 centimeters of the guide catheter 12 distal portion). Advantageously, agent flow rate of approximately 3.0 ml/second may be accomplished at about 50 psi, while not sacrificing the benefit of a smaller treatment system within the coronary vasculature. In summary, therefore, it is not the intention per se to describe all possibilities of various constructions of treatment systems and improvements thereto, but rather it is to provide examples of how one might construct exemplary devices for use in such exemplary treatment systems as described herein.

Referring to FIG. 6A, injection of agent from an injection device (as indicated by flow arrow 62) may enter a chamber 64 of modulator body 60 having a spring-loaded plunger 66 therein. The plunger 66 in this example (and in others to follow) may be in sealing, but sliding, relationship with the chamber 64—such as one might find in a syringe. Compression spring 68 (providing, e.g., spring constant $k_1$) may be positioned within the side of the chamber 64 opposing the force of injection and configured so as to resist movement of the plunger 66 against the force applied by filling the chamber with agent from the injector. As the agent injection pressure increases in chamber 64, the plunger 66 may move against the compression spring 68. The force generated by the spring 68 against the pressure of injection will be defined by the spring's spring constant (k) and the distance (L) the spring has been compressed, or otherwise displaced from its equilibrium (Hooke's Law, $F=-k*L$). FIG. 6A shows a displacement of the spring 68 (at plunger 66) within the chamber 64 of a distance greater than $L_1$. In this example, displacement of the spring/plunger equal to, or greater than, $L_1$ may allow passage of the pressurized agent to flow through an orifice in the chamber 64 and then through the "To Guide" port 58a at a minimum, threshold pressure (such as indicated by flow arrow 70). In the example described above, we have hypothetically selected a pressure of about 75 psi to produce the intended flow of agent. That is to say, when the force within the chamber 64 is equal to 75 psi/(cross-sectional area of the plunger/chamber), the force derived from the compression of the spring 68 over a distance $L_1$ should be about equivalent. The spring 68 used in producing such a force would have a spring constant (k) to optimally produce an equivalent force over the displaced length. This modulator construction may advantageously produce an injection flow profile of agent that allows flow to the guide at some intended flow rate that may be radiologically visible (i.e., $V_i$). In our example, $V_i$ may be 3.0 ml/second.

Figure 6B:
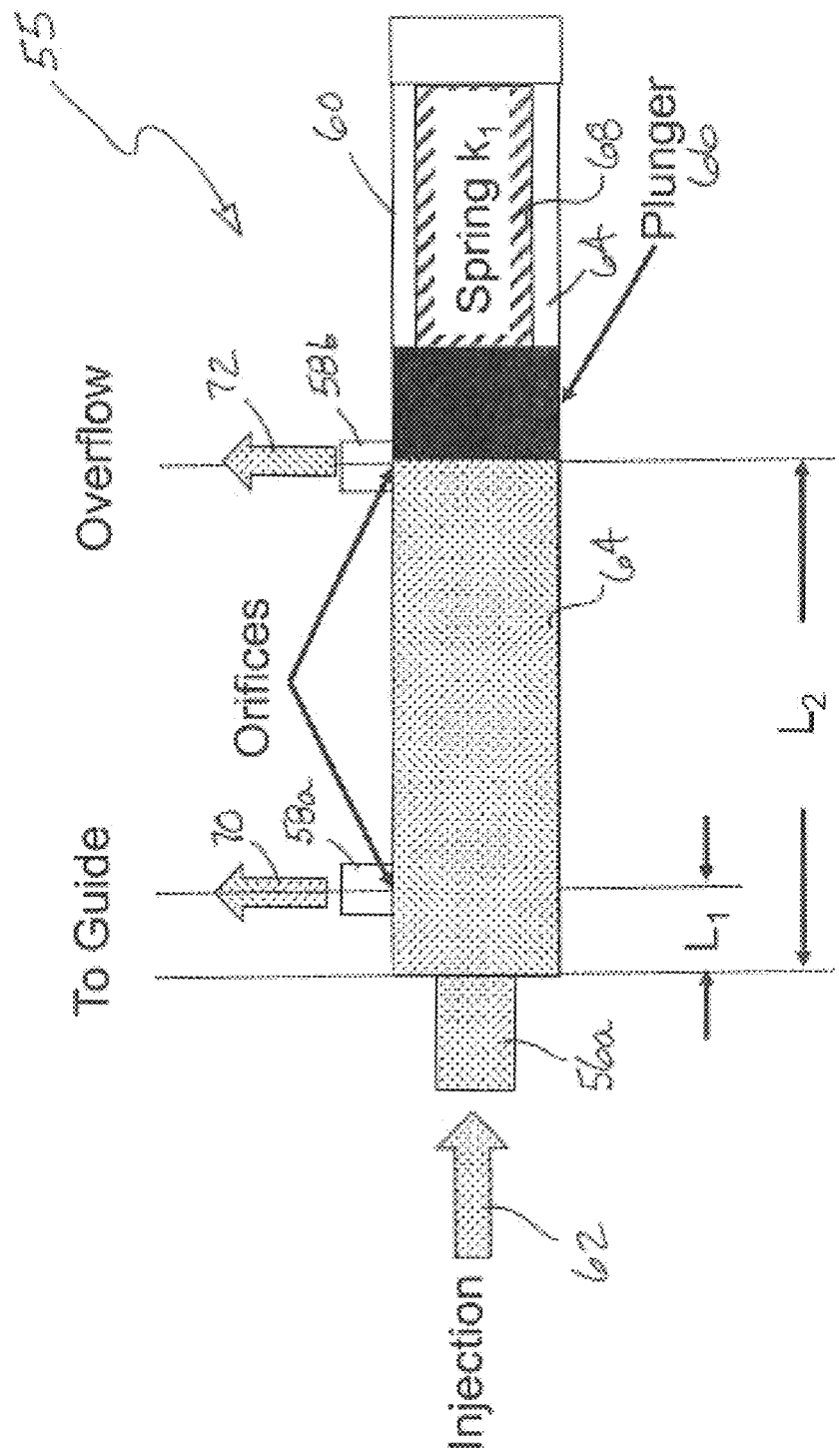
Figure 6C:
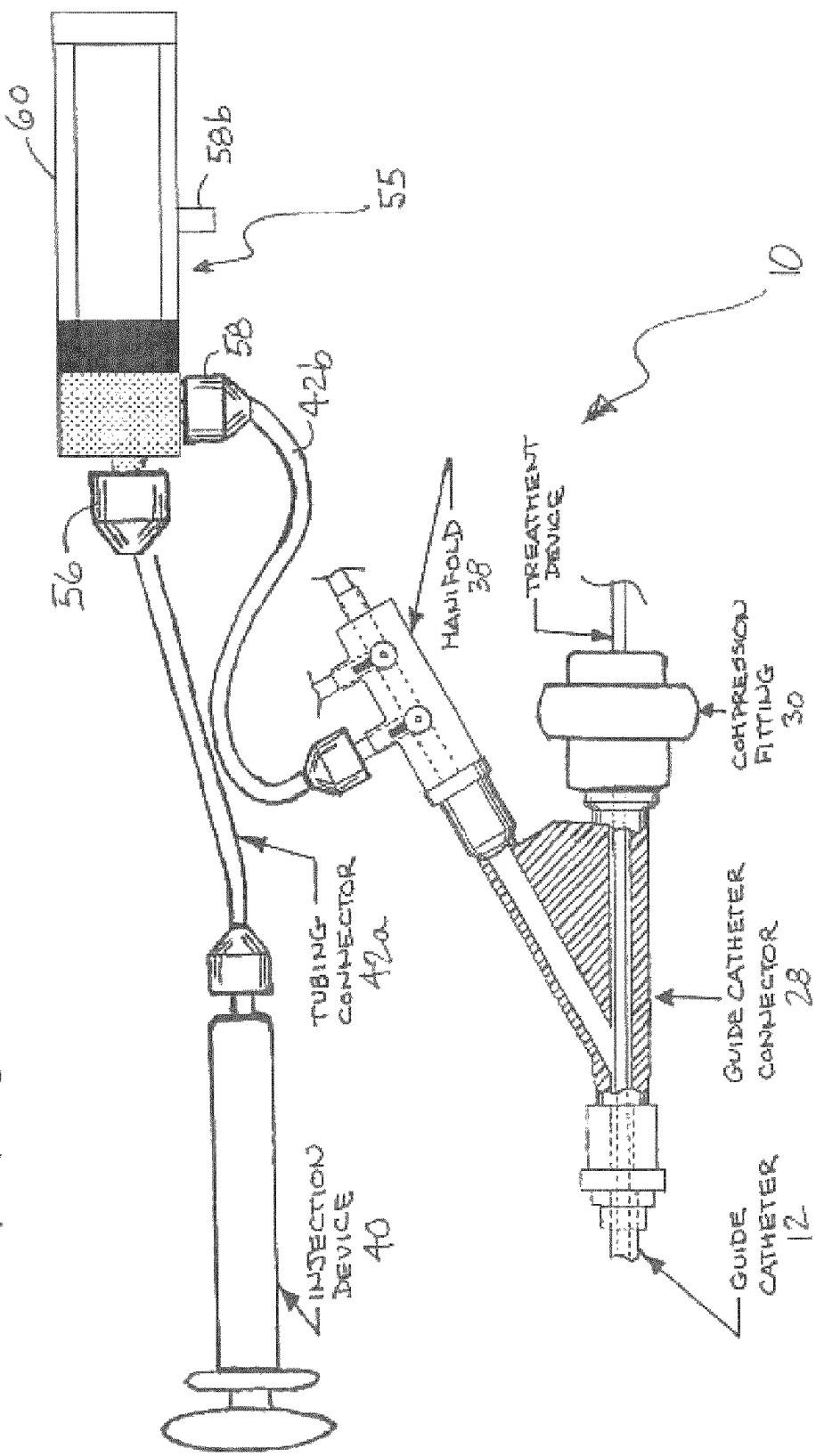
FIG. 6C illustrates the single chamber flow modulator of FIGS. 6A and 6B disposed in the proximal portion of the treatment system of FIG. 3.

Furthermore, as an injection of agent into the modulator 55 is increased in pressure, the plunger 66 of FIG. 6B may continue compression of the spring 68 along the longitudinal axis of the chamber 64 so as to expose a second orifice in the chamber 64 (e.g., to the "Overflow" port 58b) at $L_2$ wherein the highly pressured agent may be diverted away from introduction into the guide 12 (such as indicated by flow arrow 72 in FIG. 6B). For example, it may be determined that an acceptable working range of a modulator may be 75 psi to 80 psi, to produce controlled injections with flows in the above example of about 3.0 ml/second to about 3.1 ml/second. The displacements of the spring 68 with spring constant $k_1$ at $L_1$ and $L_2$ could define these operating pressures/flow rates. An injection greater than 80 psi will result in the excessive injection being bled-off into the "Overflow" port 58b, and not introduced systemically. Moreover, if the injection should fall below 75 psi, no agent will pass into the system (the plunger would be moved within the chamber by the spring such that both orifices of the chamber would close due to insufficient pressure). The exemplary modulator described may advantageously produce an improved injection flow profile, reducing inefficient agent use as illustrated as areas A, B and/or C in exemplary injection $Q_{Agent}$ profile of FIG. 4B, and resembling (within a working range), an "improved" injection profile $Q_{Improved}$ of FIG. 4C.

Figure 8A:
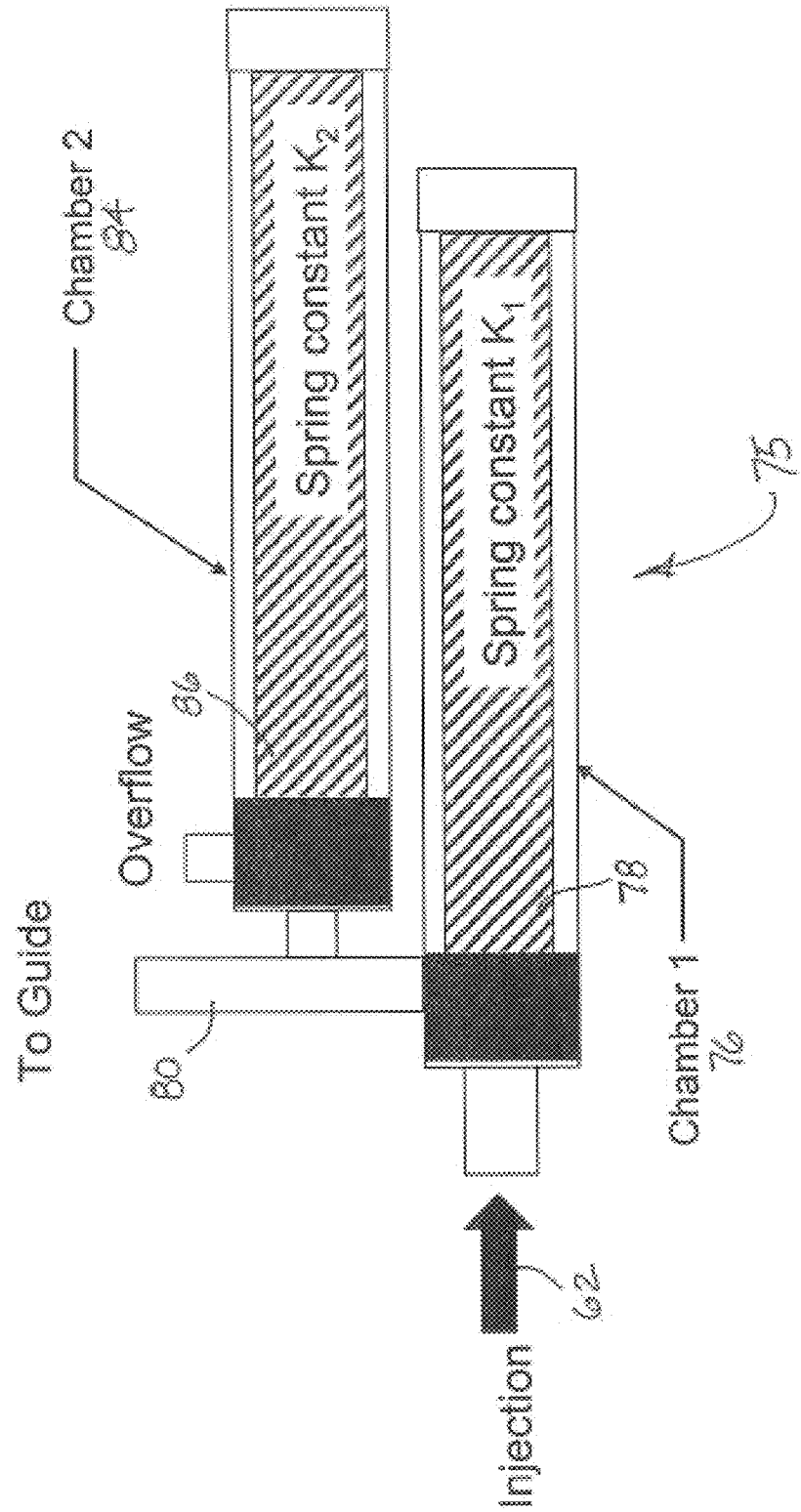
FIGS. 8A, 8B and 8C illustrate an exemplary two-chamber flow modulator, in different stages of flow control.
Figure 8B:
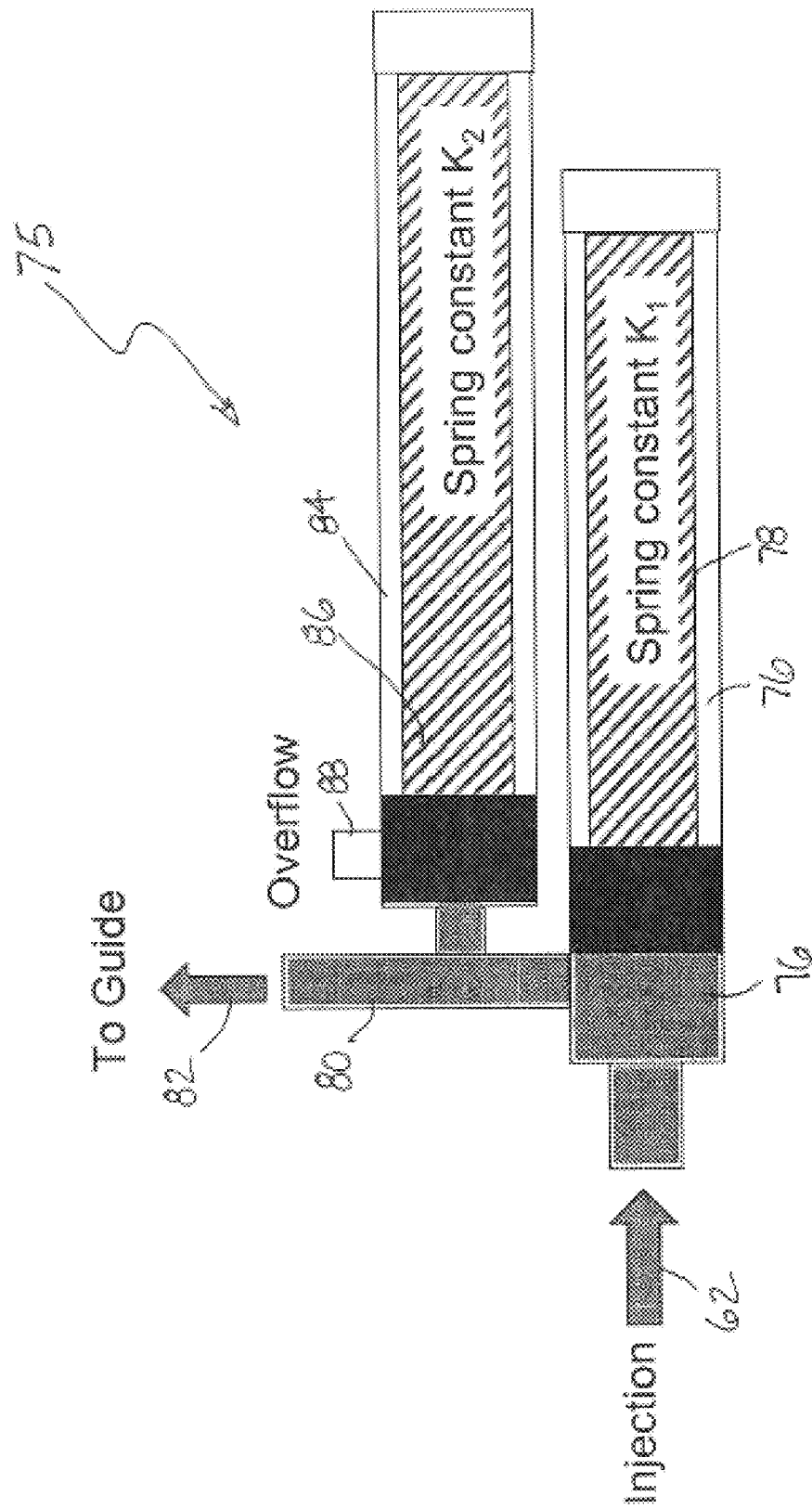
Figure 8C:
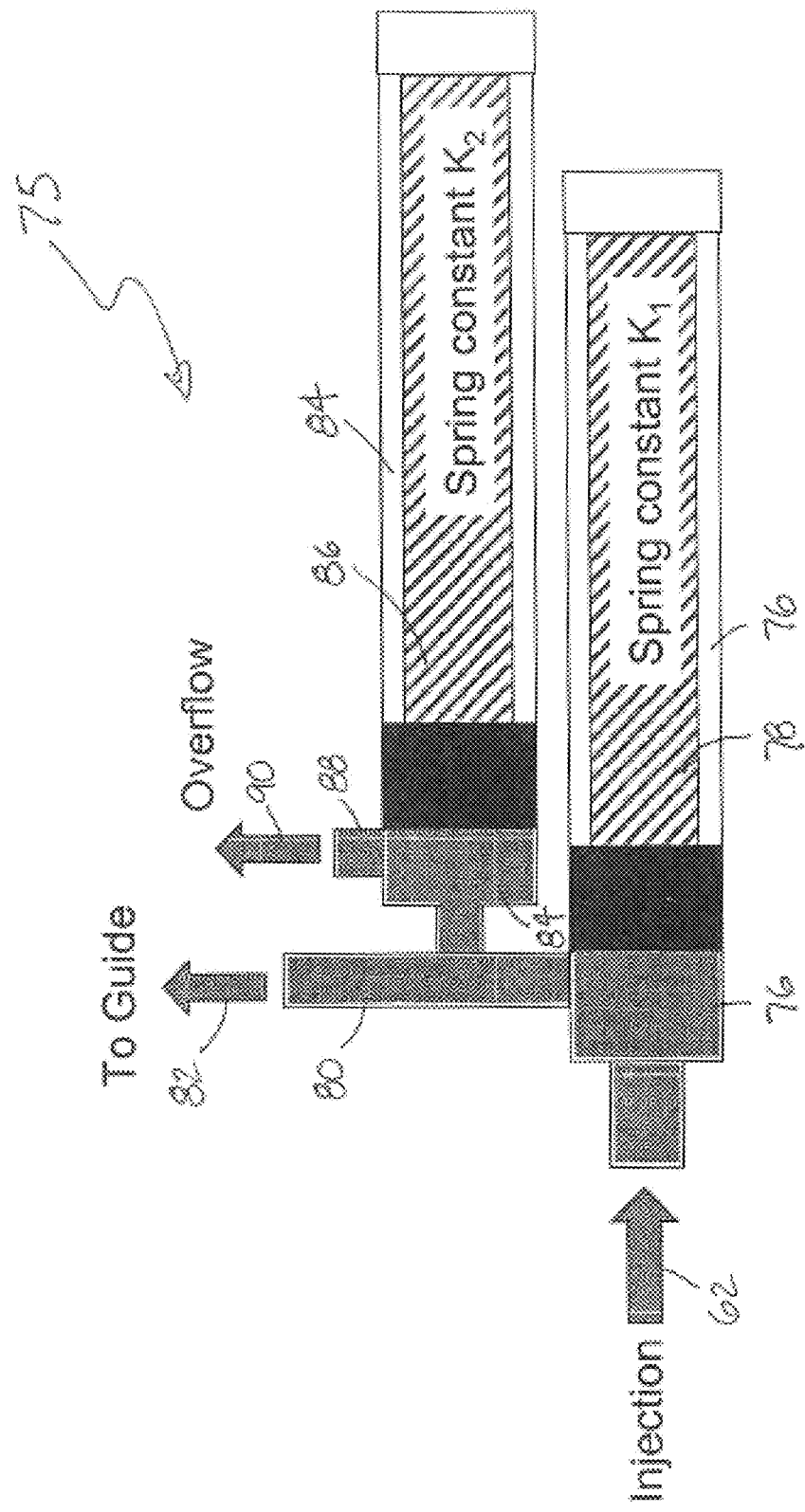

An alternative embodiment of a controlling device 75 may be of the construction as shown in FIGS. 8A-8C. In essence, a single chamber device such as illustrated in FIG. 6 may be replaced by a double chamber configuration so as to provide greater fidelity in the selection of modulator working pressures/flow rates.

As shown in FIG. 8A, there may be two separate tanks or chambers with two compression springs (having spring constants of $K_1$ and $K_2$). Medium from the injection device may be delivered to the device 75 as in device 55 of FIG. 6C (as illustrated by flow arrow 62), or any of the alternative locations described herein. Fluid flow from the injector enters chamber 1 (tank 76) and compresses plunger/spring 78 of chamber 1 until an intended pressure (and commensurate flow rate) is obtained. When the intended pressure/flow is obtained (i.e., $V_i$ at 75 psi of the previous example), the flow of medium passes via an orifice in chamber 1 and out the "To Guide" port 80, as shown in FIG. 8B (such as indicated by flow arrow 82). Chamber 2 (tank 84) is in fluid communication with port 80 and may also be pressurized by the injection. Fluid flow from the injector (via port 80) enters chamber 2 and compresses plunger/spring 86 until another compression level is reached within chamber 2, at which point plunger/spring 86 in chamber 2 will compress to a point that the passage of fluid is allowed, via an orifice in chamber 2, into port 88 (the "Overflow" port). As shown in FIG. 8C, the "decompression" of chamber 2 acts as a "relief valve" and reduces the pressure of the fluid going to the "To Guide" port 82 if the pressure in chamber 2 exceeds an upper-end threshold (i.e., 80 psi in the example of FIG. 6). Any additional pressure/volume will be bled-out of the system via port 88 (such as indicated by flow arrow 90 in FIG. 8C) and not introduced through the guide. In operation, the use of a device such as device 75 with an agent injection system may likewise produce an "improved" injection agent flow profile, reducing inefficient agent use as illustrated as areas A, B and/or C in exemplary injection profile $Q_{Agent}$ of FIG. 4B, and resembling (within a working range) the "improved" injection profile $Q_{Improved}$ of FIG. 4C.

Figure 9A:
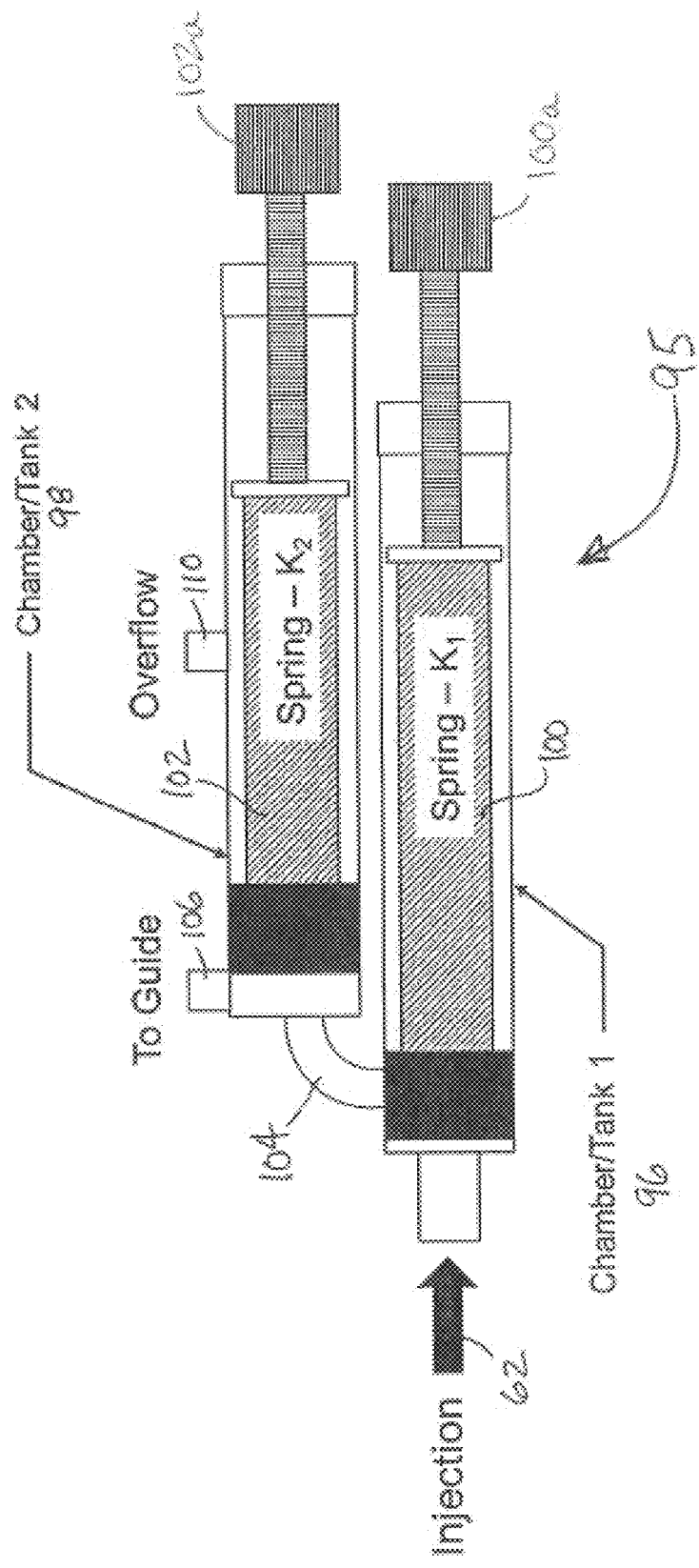
FIGS. 9A, 9B and 9C illustrate an exemplary two-chamber flow modulator with holding chamber, in different stages of flow control.
Figure 9B:
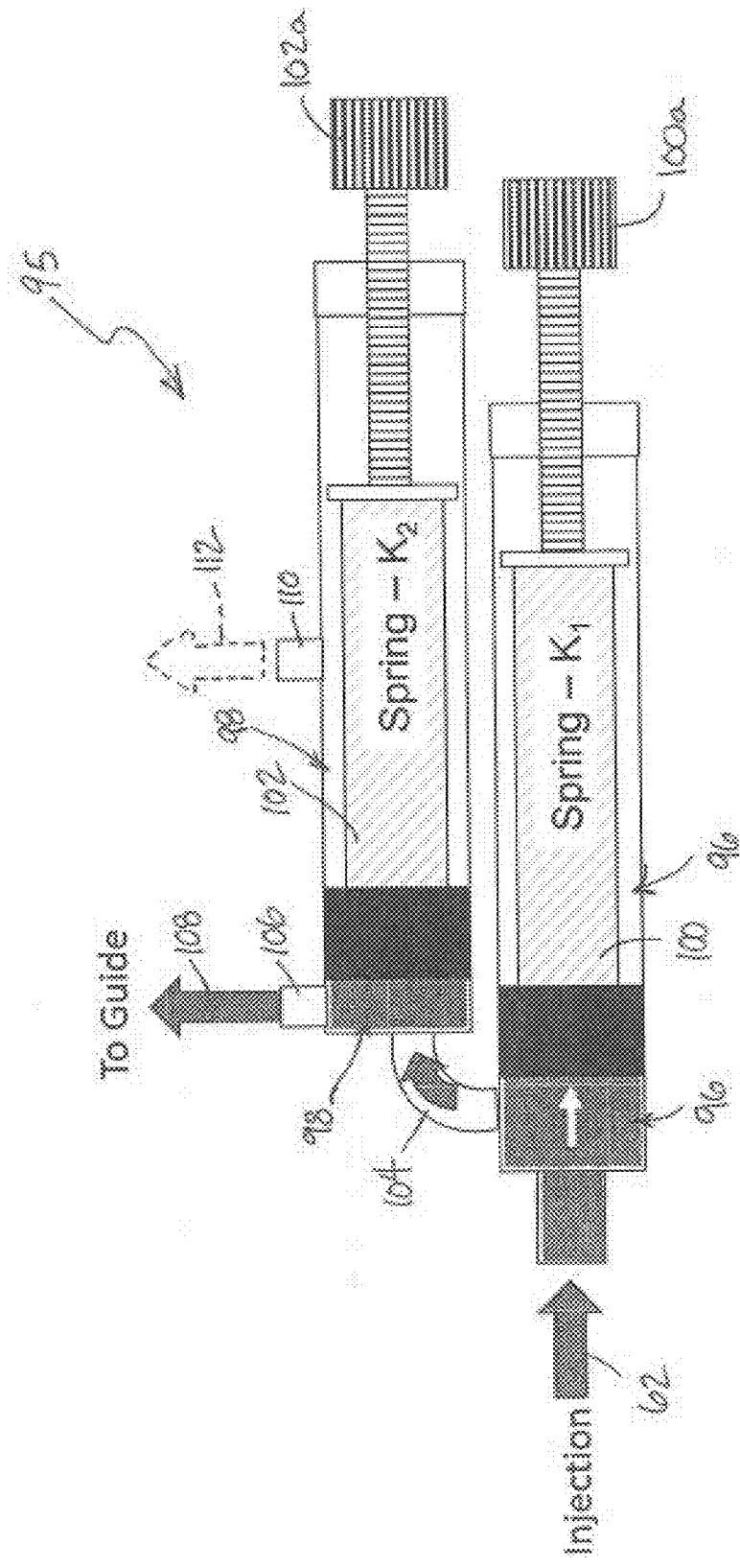
Figure 9C:
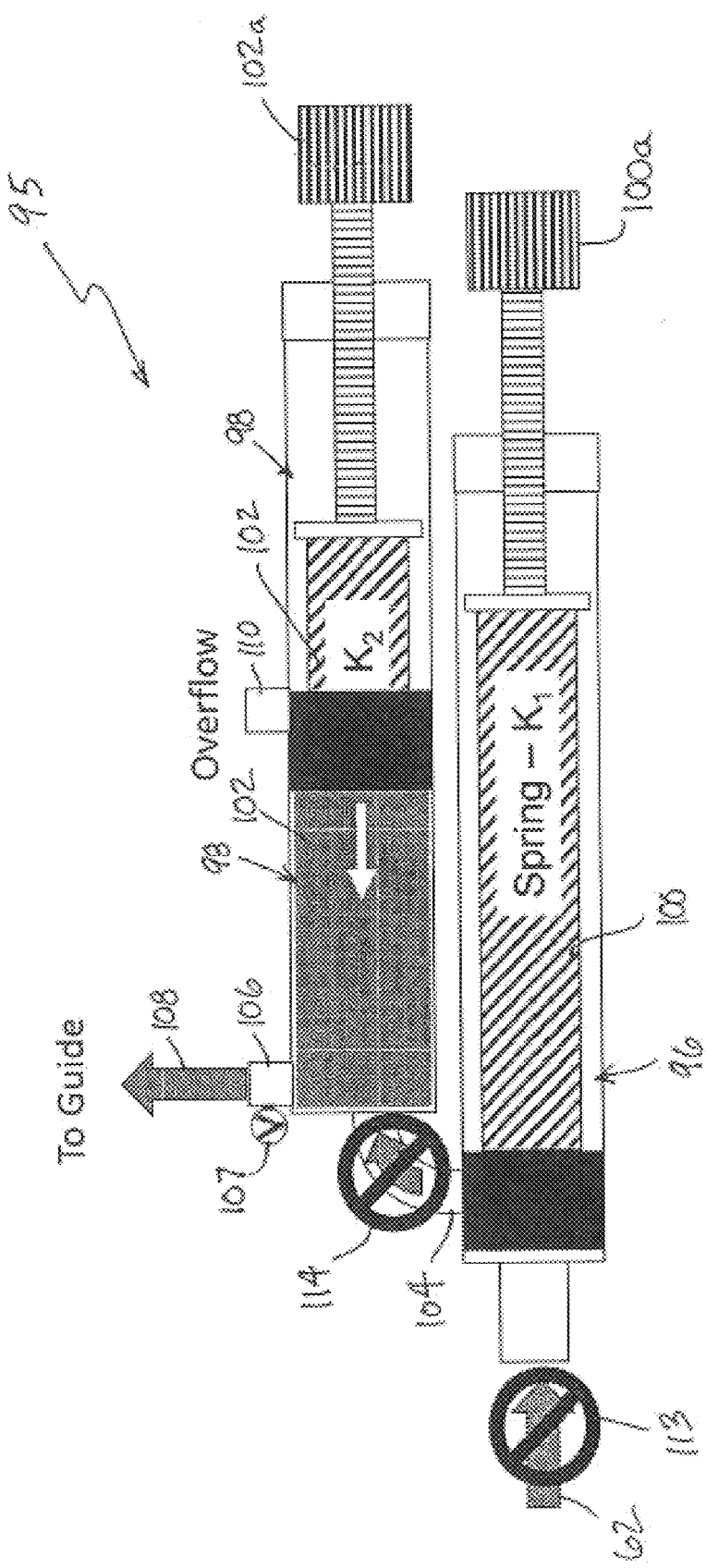

Advantageously, an alternative modulator design, as shown in FIGS. 9A-9C, might also accommodate cessation of injection from the injection device without fully ceasing the injection of medium to the guide. For example in a modulator 95 having two chambers or tanks 96 and 98 such as shown in FIG. 9A, tank 2 might include a compression spring with a lower spring constant than the compression spring in tank 1, but allow more filling of the tank 2 (i.e., greater compression length of its spring), while providing flow to the guide at an intended rate. In essence, tank 2 might act as a "holding tank" of the injection.

In further viewing FIG. 9A, the modulator 95 may comprise two tanks 96 and 98 with two compression springs 100 and 102 (with spring constants of $K_1$ and $K_2$ respectively). Medium from the injection device may be delivered to the device as in the device of FIG. 6B (as again illustrated by flow arrow 62), or any of the alternative locations described. Fluid flow from the injector enters chamber 1 and compresses plunger and spring 100 of chamber 1 until an intended pressure (and commensurate flow) is obtained. When the intended pressure/flow rate is obtained, the flow of medium passes out of chamber 1 via an orifice and into chamber 2 via channel 104, and then out the "To Guide" port 106, as shown in FIG. 9B (as illustrated by flow arrow 108 in FIG. 9B). In essence, chamber 1 provides chamber 2 with a pressurized flow of a value equal to, or greater than, some intended limit (i.e., a minimum threshold, such as 75 psi). If chamber 2 should pressurize with fluid greater than an upper threshold of some working pressure (for example, 80 psi) spring 102 of chamber 2 may compress to a point to allow passage of fluid out of chamber 2 via another orifice and into port 110 (the "Overflow" port) with any additional pressure/volume bled-out of the system, and not introduced through the guide (as illustrated by flow arrow 112 in FIG. 9B). Again, an injection system equipped with a device such as device 95 may aid in producing an "improved" agent injection profile similar to profile $Q_{Improved}$ in FIG. 4C.

Although the previous example describes using device 95 as simultaneously injecting a medium while delivering the medium to/through the guide catheter, the device 95 may also be employed to deliver the medium in a "sequential" fashion. For example, to "sequentially" inject a medium (i.e., fill a chamber with a medium to be delivered, but allow time before release of the injection), or avoid an interruption in the delivery of a medium, the device 95 of FIG. 9C may advantageously continue to deliver medium to the "To Guide" port 106 as spring 102 decompresses. As shown, the cessation of the injection 62 at a minimum level (as illustrated at 113 in FIG. 9C) may result in the cessation of medium delivered via channel 104 from chamber 1 (as illustrated at 114 in FIG. 9C) to chamber 2 since spring 100 has sufficiently decompressed so as to occlude the orifice in chamber 1 into channel 104, thus stopping the flow of medium from chamber 1 to chamber 2.

In this example, tank 2 may "bleed-out" the medium contained within tank 2 while no additional medium is injected into the device 95. The device 95 of FIGS. 9A-9C might also have a "relief" mechanism or one-way valving type system (such as valve 107 in FIG. 9C) attached to the "To Guide" port to assure that a minimum pressure is maintained as chamber 2 decompresses (i.e., a relief valve that only operates above the intended pressure of, say 75 psi and only allows flow to the guide if minimum pressure is maintained). Conversely, the spring of chamber 2 may also be designed to "close" the orifice to the "To Guide" port if a minimum level of pressure is not maintained. FIGS. 9A-9C also illustrate knurled-knob bolts 100a and 102a threadably extending from tanks 1 and 2, and attached to springs 100 and 102, so as to provide a mechanism for independently adjusting the forces delivered by their respective plungers.

Figure 10A:
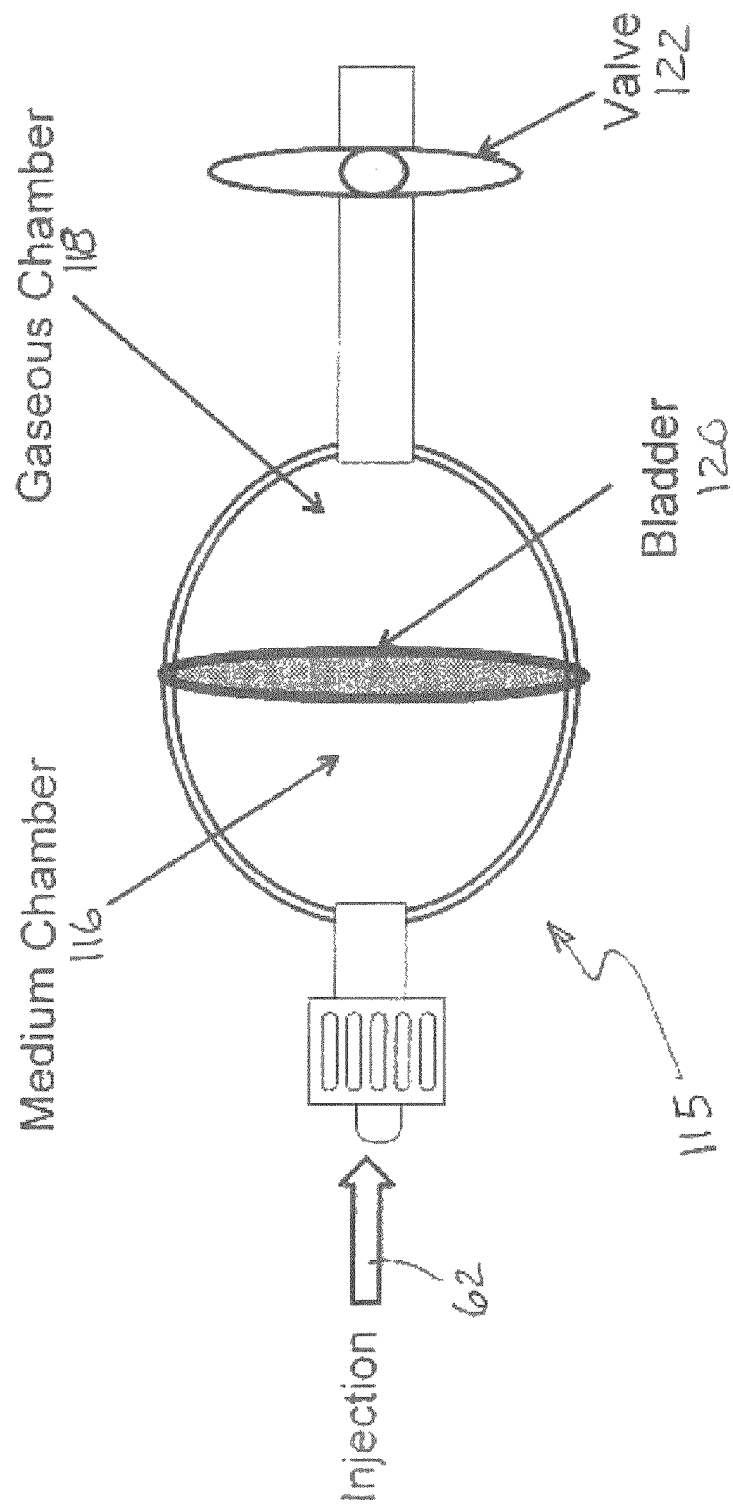
FIGS. 10A and 10B illustrate a capacitance chamber flow modulator (bladder), in different stages of flow control.
Figure 10B:
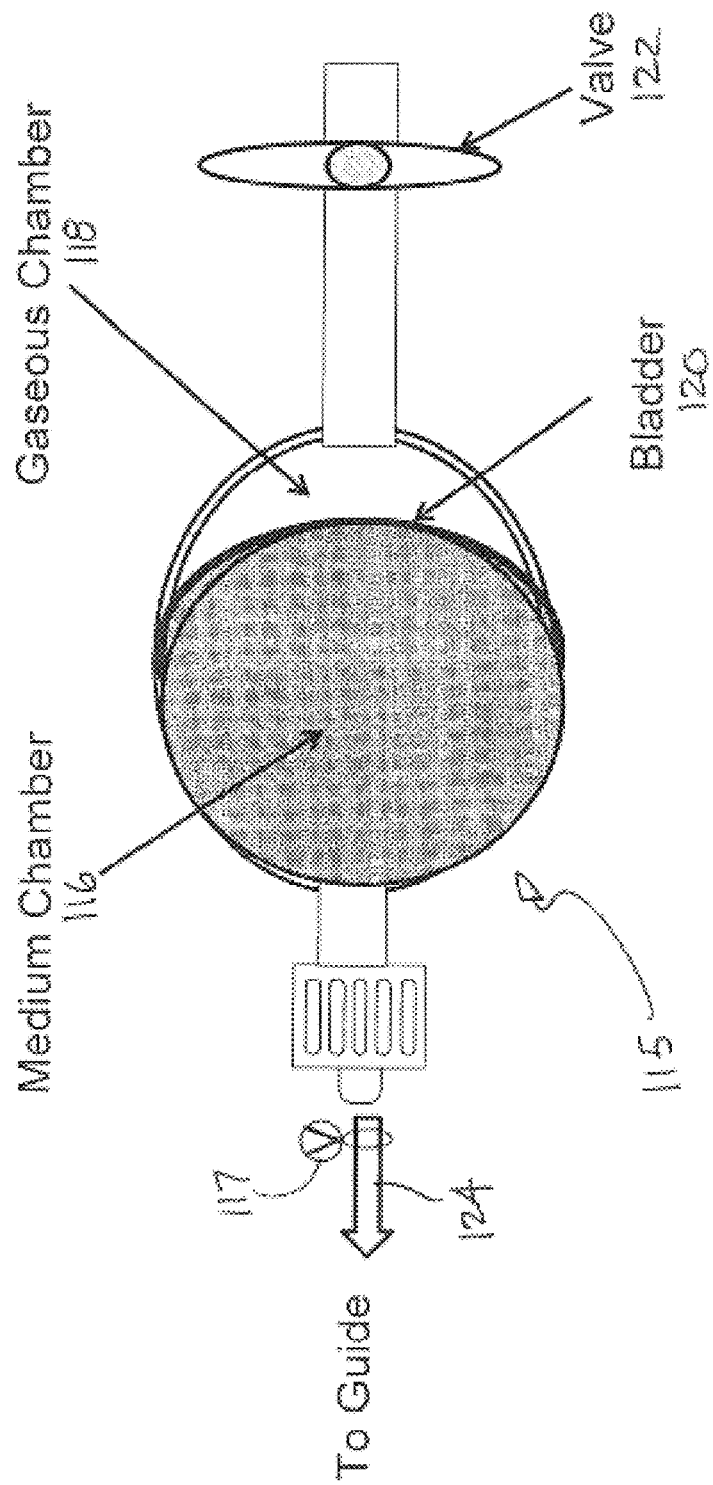

An alternative example of a regulator that could be used for sequential or/and simultaneous injection may be seen in FIGS. 10A and 10B. In this exemplary embodiment, a pressure chamber is filled with a quantity of medium to be delivered. The pressure and volume of the medium to be injected to a guide may be determined when it is introduced into the chamber, or conversely the chamber may be designed to provide/apply pressure upon the medium within the chamber after its introduction. FIGS. 10A and 10B illustrates such a modulator 115 that comprises a compartment (medium chamber 116) defined for a medium to be injected, another compartment (gaseous chamber 118) for receiving a gaseous medium (e.g., air), and a deformable bladder 120 sealingly separating the compartments 116 and 118. As seen in the example, a valve 122 may be used to facilitate the flow of gas in and out of compartment 118 (e.g., to seal the gaseous compartment 118). The medium to be delivered can be introduced into the chamber 116 of the modulator 115 with the gaseous compartment valve 122 closed. During introduction of medium, the start of which is shown in FIG. 10A (fluid filling from the injector as indicated by flow arrow 62), the bladder 120 may deform into the gaseous compartment 118 until the medium obtains an intended pressure for the delivery of the medium to the guide catheter. Not shown in FIG. 10 are the valve mechanisms (such as those found on the manifold 38, for example, of FIG. 3C) to allow the passage of medium, and retention of medium within the modulator 115, until an injection to the guide is warranted. The medium may be released from the chamber 116 by opening, or otherwise activating, a valve (not shown) between the medium chamber 116 and the guide. FIG. 10B illustrates releasing of the medium from the chamber 116 to the guide catheter (as indicated by flow arrow 124).

Conversely, the chamber 116 of FIG. 10A might be filled with injection medium first; and, then pressurized to an intended delivery pressure by introduction of gas into the gaseous compartment 118, thus applying pressure to the medium through the bladder 120.

Although the previous description of device 115 may be illustrated as "sequential" delivery, device 115 may be designed to act as a "capacitor" during simultaneous delivery. In this case, there may be another port (a "To Guide" port configured on the medium chamber 116, not shown), to allow delivery from the device 115 during injection.

A modulator 115, such as example devices of FIGS. 10A and 10B, may advantageously provide a flow profile that resembles the injection $Q_{Improved}$ of FIG. 4C, at least as it pertains to areas A and C of FIG. 4B, since the injection may be delivered quickly to a $V_i$ flow rate, accommodating a quick ramp up and a fairly even flow rate for a short period of time. With respect to area B of FIG. 4B, chamber 116 of FIGS. 10A and 10B may decompress (while delivering flow) to a level that is below an "improved" working range. To compensate for this, a mechanism (such as a one-way value; e.g., valve 117 in FIG. 10B) may be disposed between the chamber and the guide to assure that the medium flow rate delivered meets the intended limits (e.g., minimal flow rate) for the injection, or terminates the flow.

Figure 11A:
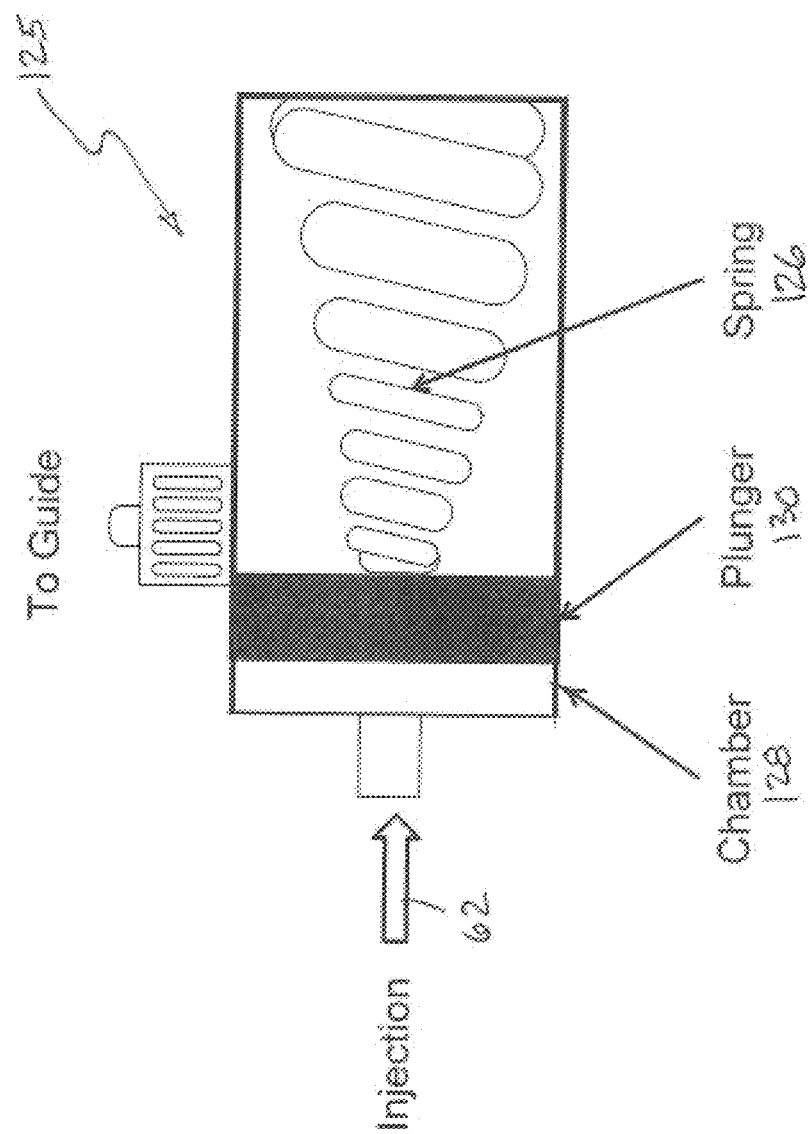
FIGS. 11A and 11B illustrate an exemplary flow modulator with constant force chamber, in different stages of flow control.
Figure 11B:
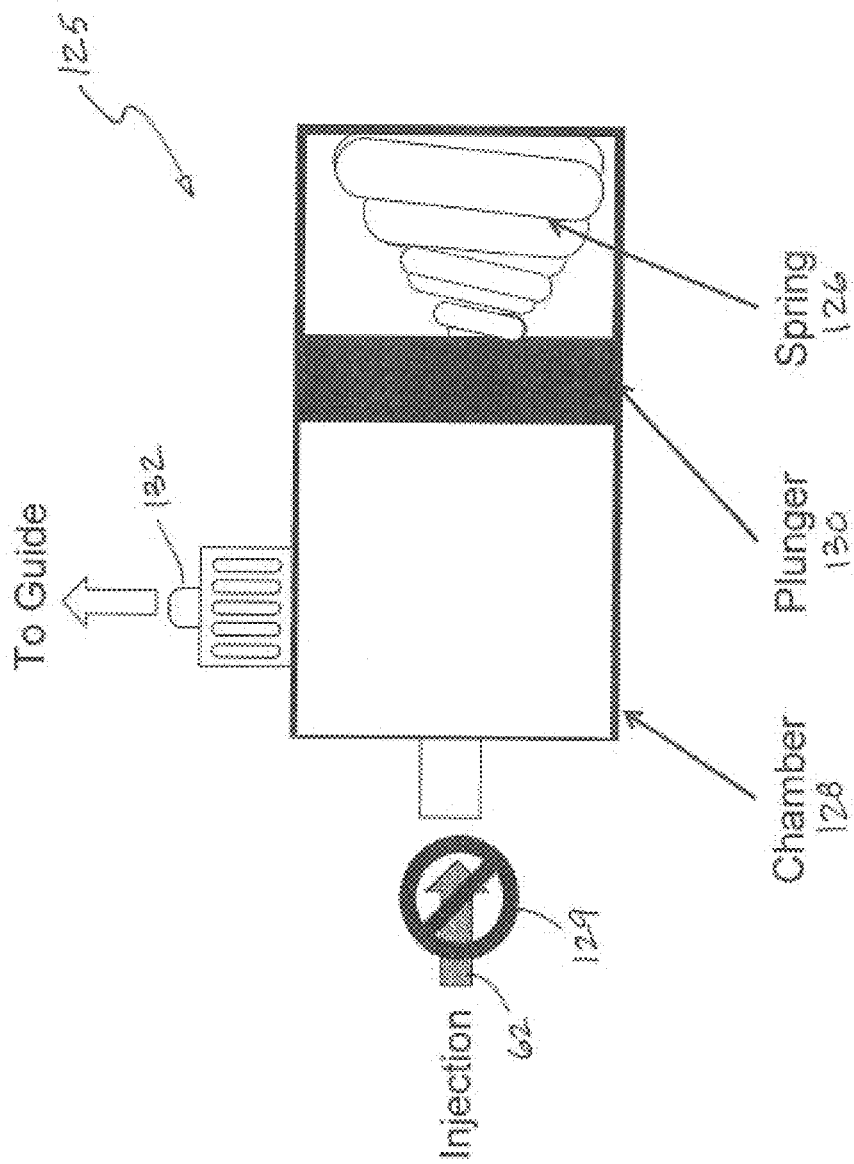

An alternative construction of a modulator may include a chamber constructed with a constant force spring, as shown in FIGS. 11A and 11B. Such a spring, by design, may deliver a constant force on a member (such as a plunger) over its working range (displacement). A modulator 125 of this type may include a conical spring (126 as shown in FIG. 11A) as an example of such a spring that can be made to have a constant force delivered over different compression lengths (displacements from equilibrium). The spring 126 may have variable pitches, with a larger pitch in its larger outer coils and a smaller pitch in its smaller inner coils, thus collapsing/ expanding the coils at the same force during compression/ decompression. Similar to the other devices described herein, the alteration of an injection's pressure and flow may be performed while delivering media to a delivery site, as well as performed by more than one step/sequence in delivery.

Using such a constant force injection modulator 125 as described, one might inject a quantity of medium into a chamber 128 of modulator 125 (as indicated by flow arrow 62), leading to compression of conical spring 126, as seen in FIG. 11B. Once a desired volume of medium has be received within chamber 128, injection may be stopped and/or back flow of medium from chamber 128 to the injector prevented (such as by manipulation of a valve—not shown), as further illustrated at 129 in FIG. 11B. Upon actuation, or otherwise release, of medium from the chamber 128 (such as opening of a valve to the guide—not shown) a plunger 130 may drive (as urged by compressed spring 126) the medium from the chamber 128 with constant pressure (and commensurate volume flow rate) toward the guide via an orifice in chamber 128 leading to the "To Guide" port 132. It might be advantageous with this modulating system 125 to allow "space" within the chamber 128 for the plunger 130 to close the "To Guide" orifice once a desired volume has been delivered.

An alternative construction (not shown) for the modulation system 125 of FIGS. 11A and 11B might also include mechanically driving a displacement/plunger element at a constant force within/upon a chamber so as to achieve a constant pressure upon the chamber and drive agent at a constant flow rate to the delivery catheter. Such a chamber might have a construction as shown in FIG. 11A. An alternative embodiment for simply providing constant force on a plunger in a chamber might include the placement of a weight upon a vertically-mounted plunger element within the chamber. For example, a syringe-type chamber might be vertically situated with the displacement actuator/element located above (further away from the center of the earth), and the outlet port located below (closer to the center of the earth). After filling the chamber with medium, various weights may be placed upon the displacement element so as to create the intended constant force upon the plunger (e.g., using gravity upon a mass in deriving a constant force). When an injection is needed, the medium may be released (or otherwise actuated to be released) from the chamber by opening a valve (such as a stopcock). The opening of the valve thus allows the medium to exit the chamber as a result of the force placed on the medium from the weight upon the plunger. The measure of the weight might be, for example, similar to the force determined for the constant force modulator 125 described above.

An alternative use of regulator 125 of FIG. 11 might be employing the regulator during the simultaneous injection and delivery of medium to/through the delivery catheter. With this application, injecting medium into chamber 128 with constant force spring 126 may provide a "pre-loaded" resistance to filling of the chamber. Once a pre-set level of pressure is achieved, regulator 125 may allow injectate to pass into chamber 128 and out of the chamber through the "To Guide" port 132. Additional filling of chamber 128 may take place during injection of medium if the injection pressure is greater than the pre-set spring resistance (and assuming sufficient resistance to delivery in the delivery catheter). In addition to filling, the chamber 128 may "discharge" medium (a reduction in volume) at a constant pressure (approximately the pre-set level of pressure) if/when the pressure from the injector is less than the pre-set resistance by constant force spring 126. With this exemplary simultaneous modulation, regulator 125 may act as a "capacitor" (i.e., having the ability to store and discharge a pressurized volume of medium) so as to "level-out" or "smooth-out" the pressure/flow profile of a medium directed to the catheter during injection.

Further to the description of modulator 125, and other media modulators described herein, manual injection (such as a syringe) during delivery media to an injection site might have varied pressures/flows passing to the modulator. Not only might the flows/pressures to the modulator be varied, but it is conceivable (depending on the system construction) that the flow of injection medium might, at times, return into the injector (syringe). As an example, it is possible that an administrator of a syringe might release the pressure placed upon the plunger. Depending on this reduced force, it is possible that the pressure/fluid stored into chamber 128 may be diverted back to the syringe—a function of the "least path of resistance" to the flow from the capacitance chamber 128.

Figure 20:
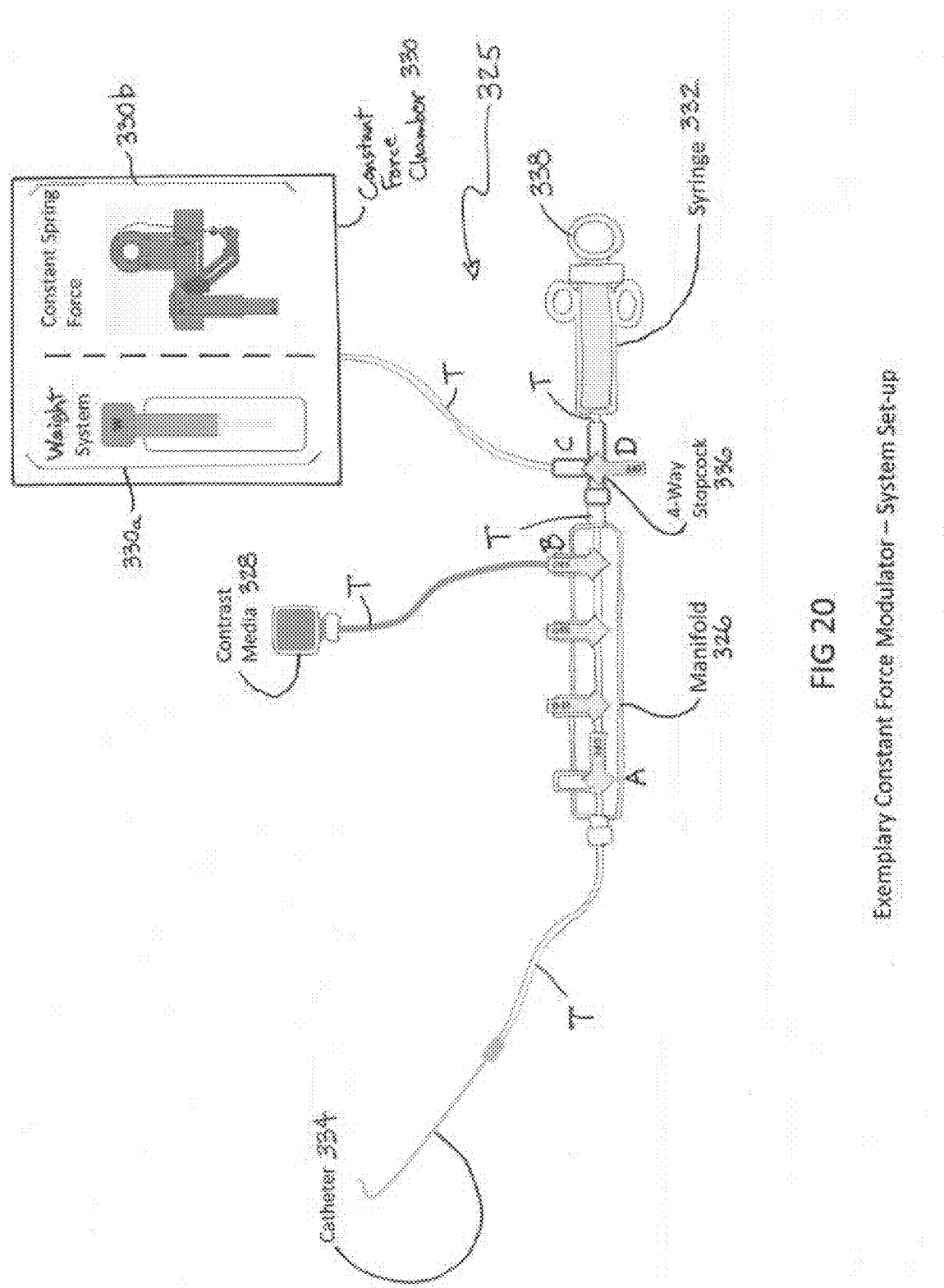
FIGS. 20-22 illustrate an exemplary constant force modulator system, in different stages of flow control.
Figure 21:
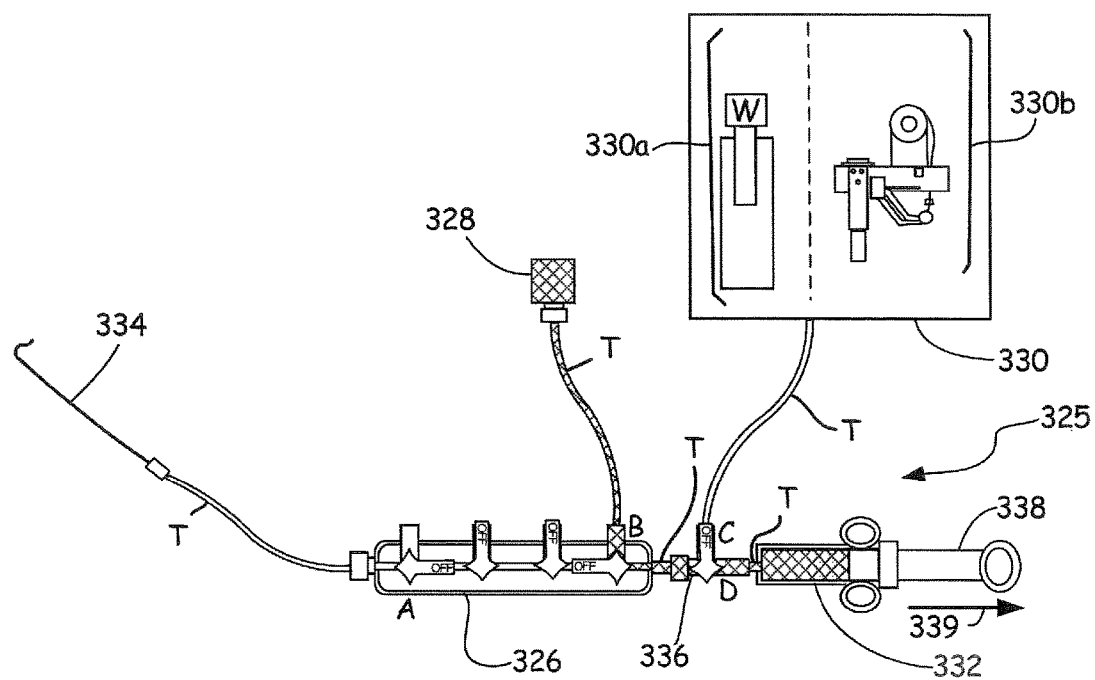
Figure 22:
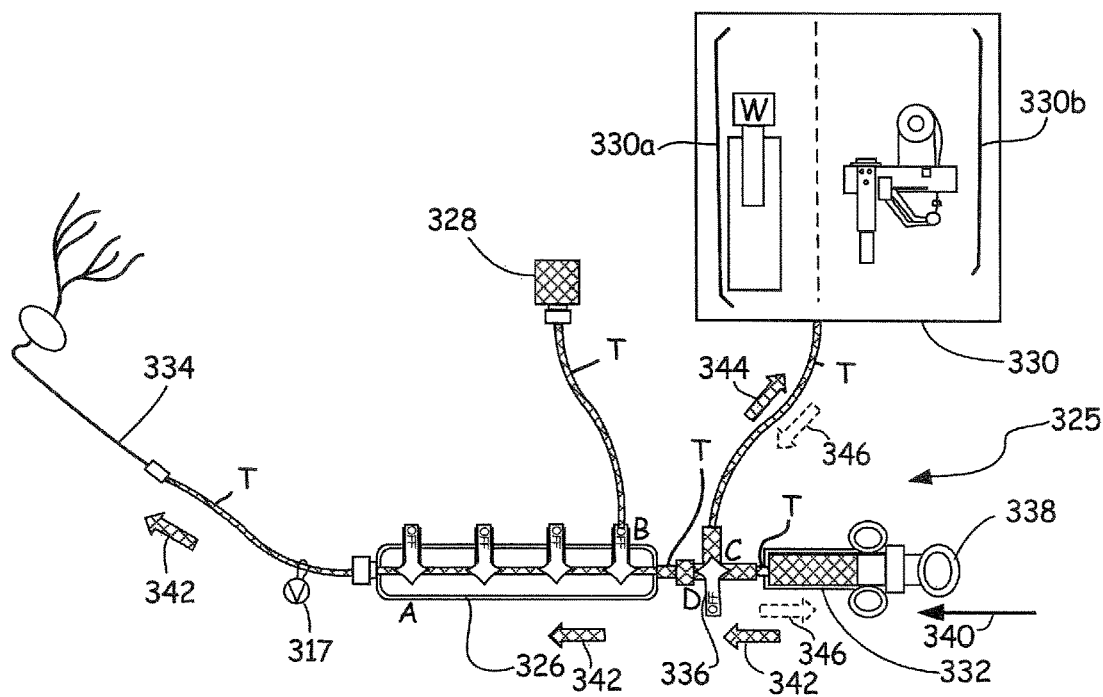

Advantageously, a modulator having a constant force chamber of such construction may be configured to improve a medium injection flow/pressure profile delivered to a delivery catheter. FIGS. 20 to 22 illustrate such an alternative system configuration/construction, and its method of use, which may provide an improved pressure/flow delivery profile. A modulator system 325 of FIG. 20 includes a manifold 326 having several elements attached to the manifold 326 to include: a reservoir or vial 328 of medium (i.e., contrast agent), a constant force chamber 330, an injector 332 (e.g., syringe), a delivery catheter 334, and a 4-way stopcock 336. These elements may be configured so as to be in fluid communication with one another, at times, via suitable tubular members T. Valves A (manifold to catheter), B (medium vial to manifold), C (constant force chamber to manifold), and D (injector to manifold) may allow for opening and closing such fluid communications between the manifold 326 and different elements of 328, 330 332, 334 and 336 of modulator 325. Note that 4-way stopcock 336 may provide the valving functions of valves C and D in lieu of separate valves/attachments. Of further note, the constant force chamber 330 may be configured, as illustrated, to accommodate a weighted force element (discussed previously) or a coiled constant force element, so as to deliver a constant force upon medium in a chamber therein with a displaceable plunger or surface. These are but two examples of how one might configure a constant force chamber and, as such, are to be illustrative but not limiting in the various configurations to construct a constant force apparatus.

In the exemplary method of performing an injection modulation, contrast agent from vial 328 is drawn into the syringe 332 by closing valve A (to prevent flow between the manifold 326 and the delivery catheter 334), opening valve B (to permit flow between the medium vial and the manifold 326), closing valve C (to prevent flow between from the constant force chamber 330 and the manifold 326), and opening valve D (to permit flow between the manifold 326 and the syringe 332), as represented in FIG. 21. The syringe 332 may be filled with injectate medium by drawing on a plunger 338 of the syringe 332, as represented in FIG. 21 by arrow 339, to thus draw medium from vial 328 into syringe 332. Valve B (between medium vial 328 and manifold 326) may be closed when sufficient medium has been drawn into syringe 332.

Whether a construction having a weighted force element acting upon a plunger (such as illustrated by weight system 330a), a construction employing a constant force spring acting as a plunger (such as illustrated by constant spring force 330b), or an alternative constant force contrivance, a load is determined to be deployed upon the chamber in vial 328 (and its fluid contents) sufficient in regulating medium flow to be delivered by the delivery catheter 334. For the sake of elucidation only, say a pressure of 50 psi is wanted at the manifold 326 (e.g., into the proximal port of the delivery catheter 334) to create an improved medium delivery flow through the catheter 334. Constant force chamber 330 may be configured so as to generate approximately 50 psi upon a fluid within, entering, or exiting, the constant force chamber 330 when valve C is opened (i.e., open to permit flow from constant force chamber 330 into the modular system 325).

When an injection of medium to an injection site is warranted, valves A (to catheter 334), C (to chamber 330) and D (to syringe 332) may be opened and the plunger 338 of the syringe 332 depressed (in direction of arrow 340 in FIG. 22). As the plunger 338 of the syringe 332 is quickly depressed, the fluid ejected from the syringe 332 will want to travel towards the least path of resistance, simultaneously driving fluid to the catheter 334 (as represented in FIG. 22 by medium flow arrows 342) while passing into the constant force chamber 330. Rapid introduction of medium by the syringe 332 will allow the pressure within the manifold apparatus to quickly obtain 50 psi, and allow for filling the constant chamber force 330 with medium (via flow of arrow 344) when pressure is greater than 50 psi. Thus, constant force chamber 330 acts as a capacitor as it takes on more medium at, or above, a pressure of approximately 50 psi; while, also allowing the delivery of medium to the catheter 334 at approximately 50 psi (via flow arrows 342). In essence, the flow delivery profile of the modulator 325 may reduce the "wasted" contrast due to ramping-up pressure/flow (area A of FIG. 4B); as well as, reduce the "wasted" contrast from over-injecting into the delivery catheter (area C of FIG. 4B) by maintaining a more constant pressure within the manifold.

In the example shown in FIGS. 20 to 22, once the operator has filled the constant force chamber 330 with contrast medium to some degree, the constant force chamber 330 may continue to discharge the wanted 50 psi to the delivery catheter 334 even if the injection flow is diminished, thus facilitating a "smooth" injection to the delivery catheter 334.

When it is determined that sufficient medium has been delivered by the syringe 332, releasing the plunger 338 (e.g., allowing the plunger 338 on the syringe 332 to negatively displace with no loading) may allow a rapid drop-off of pressure from the manifold 326 as the pressure within the constant force chamber 330 may be dissipated by discharging flow away from the delivery catheter 334 and into the syringe 332 (e.g., least path of resistance—represented by the phantom arrows 346 in FIG. 22). Thus, the rapid decrease in pressure delivered to the delivery catheter 334 may act to reduce the "wasted" contrast as typically seen at the tail end of an injection (e.g., area B of FIG. 4B). It is also possible to facilitate the rapid termination of the injection by closing valve A (manifold to catheter) before, during, or quickly after an injection is terminated by the syringe 332.

The termination of the medium injection also may be enhanced by including other mechanisms (such as a one-way valve) so as to quickly shut-off delivery to the catheter 334 when there is insufficient pressure (e.g., when a selected low pressure threshold is reached). Such a one-way valve could be placed at various locations within the modulator system 325, including its residing between the manifold 326 and the delivery catheter 334, along the tubular connector therebetween, such as illustrated by valve 317 in FIG. 22.

Figure 12A:
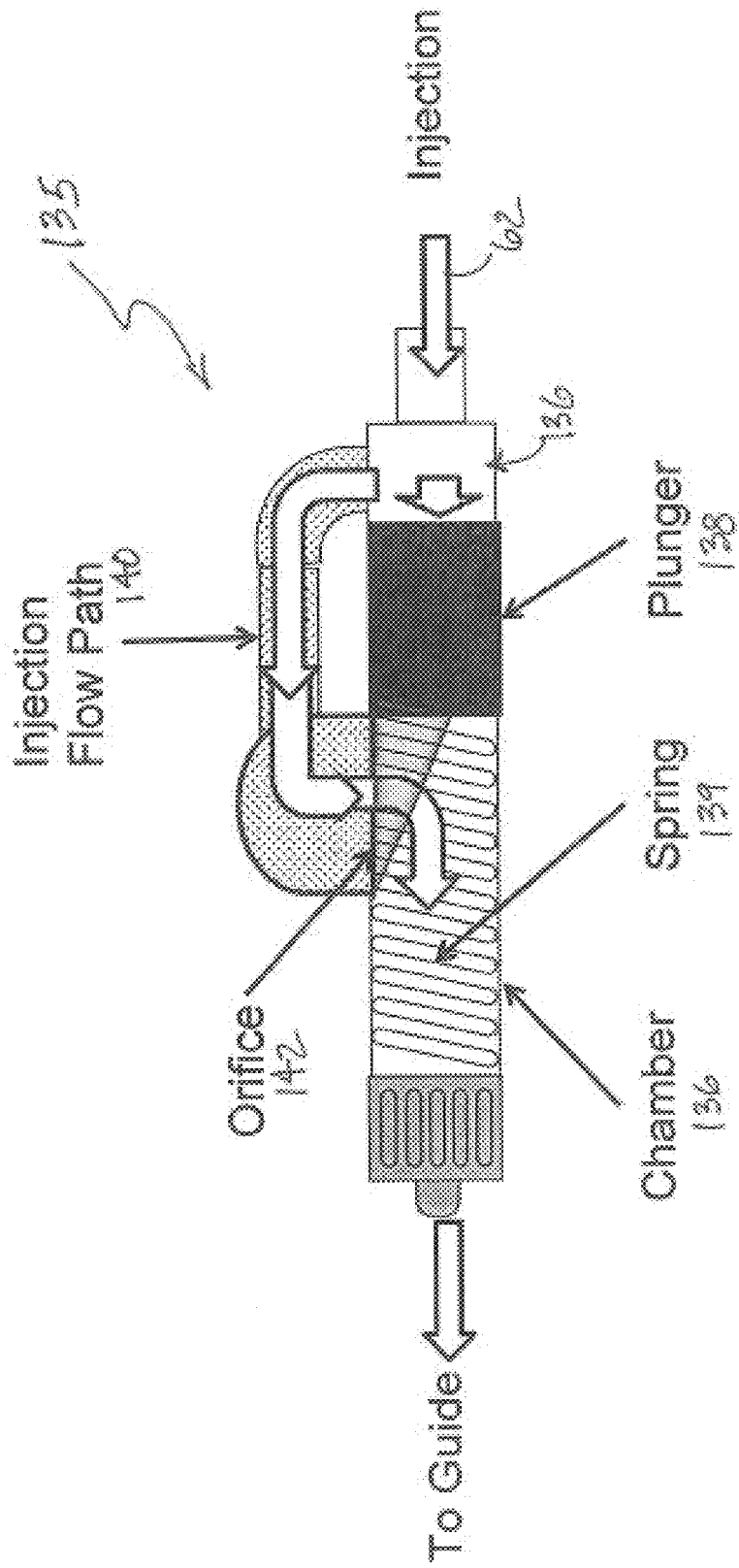

An alternative embodiment in the modulation of flow through a device to control injections may be found in FIGS. 12A and 12B, which illustrate a constant flow rate modulator 135 that may advantageously modulate the flow rate delivered to the guide (or any other delivery device). A modulator such as this might be useful for delivering a constant flow rate of a medium to a target site, independent of using different conduit configurations. For example, the resistance to flow of a medium through an angiographic catheter (for diagnostic visualization of an artery) may be different than the treatment system described previously. And, as such, the pressure required to drive constant agent flow through an angiographic catheter typically may be lower than the pressure necessary to drive similar agent flow through the treatment system. Advantageously, a physician may be able to perform an angiographic assessment (with an angiographic catheter) of an artery, as well as a treatment (with a treatment system) with the same modulator delivering similar constant flows of agent. An arrangement as shown in FIGS. 12A and 12B may allow a physician to switch between both agent delivery systems with the same modulator 135.

Referring to FIG. 12A, the injection device provides an injection (see flow arrow 62) into a chamber 136 of the modulator 135. The injection acts upon plunger 138 (that is sealably and movably disposed within chamber 136, and biased in opposition to initial injection medium pressure by variable force spring 139) with a force derived from the pressure of the medium over the area of the plunger 138. The flow of medium is directed out of chamber 136 along an injection flow path 140, by-passing the plunger 138, and then re-establishing flow within the chamber 136, via an orifice 142, on the guide side of the plunger 138. Depending on the pressure that the medium experiences on the guide side of the modulator 135, the spring-engaged plunger 138 will be driven (by the force of that pressure) to a location along the orifice 142 passing through the wall of the chamber 136. The placement of the plunger 138 (and its associated spring 139, and the bias force of spring 139) and its relationship to the orifice 142 may partially restrict the flow of the medium into the guide portion (i.e., guide catheter side) of the chamber 136. As an example, the orifice is held completely open in the drawing of FIG. 12A, suggesting the pressure of the injection may be nearly the pressure in the guide portion of the chamber 136, with the modulator "opening the flow" of the orifice 142 as much as possible to allow greater flow. The differential of pressure, and thus the forces acting upon both sides of the plunger may be nearly the same in FIG. 12A. An example of this scenario may be when there is relatively high resistance to medium flow in the delivery guide (e.g., when in use with a treatment system).

Conversely, FIG. 12B shows the orifice 142 partially occluding the flow from the injection flow path 140 into the guide portion of the chamber 136. In this case, there may be less resistance (i.e., medium flows more readily) from the guide or delivery catheter and the differential in pressures within the two sides of the chamber 136 have increased. In other words, the injection path has been restricted (driven by the pressure differentials) to drive the fluid in a delivery catheter having less resistance (and, therefore requiring less pressure) in delivering an equivalent flow rate (such as when in use with an angiographic catheter). In both cases presented, the flow rate of medium to/though the delivery catheter may be the same; however, it is the modulator that may be configured to adapt/change resistance to flow in order to accommodate constant flows (delivery of medium with different systemic resistances).

The example of the flow modulator of FIGS. 12A and 12B illustrates a chamber with a single, graduated orifice in performing the constant flow rate modulation function. However, such a function could be performed with a multitude of orifices, as well as with different cross-sectional areas of the orifice(s) to accomplish the same intended function. In addition, other forms of variable pressure restrictors (having constant flow rate modulation) may accomplish the intended function. As such, these alternatives are considered within the scope of the disclosed devices and processes.

It should be also noted that the exemplary descriptions have assumed that the ancillary tubings/connections/channels within and/or between system components/devices, are relatively large and may have negligible "resistive" impact on the overall flows/pressures modulated by the devices. For example, the pressure drop created by the lumen of the channel between chambers 1 and 2 of FIGS. 9A-9C, or within the connective tubings and/or connectors of FIGS. 6A-6C should be minimal. If not, design changes could be made to accommodate for the additional resistances created with such connections without deviating from the scope of the disclosed devices and processes.

Although the various constructions of modulating devices have been described as having chambers with springs therein, it is clear that any passive and/or active biasing or valving mechanisms (or any combination thereof) might also be used to produce similar functions. For example, hydraulic valves, release valves, one-way valves may perform functions so as to activate or otherwise modulate flow (i.e., allow flow) upon a known/determined flow rate and/or pressure, as well as deactivate (stop or limit flow) once a known/determined flow rate and/or pressure condition has been obtained. It is within the scope of the devices and methods described herein to include such alternative devices, or devices in combination, to produce similar injection modulation effects.

Exemplary Modulation Devices and Methods with Synchronization

Figure 13:
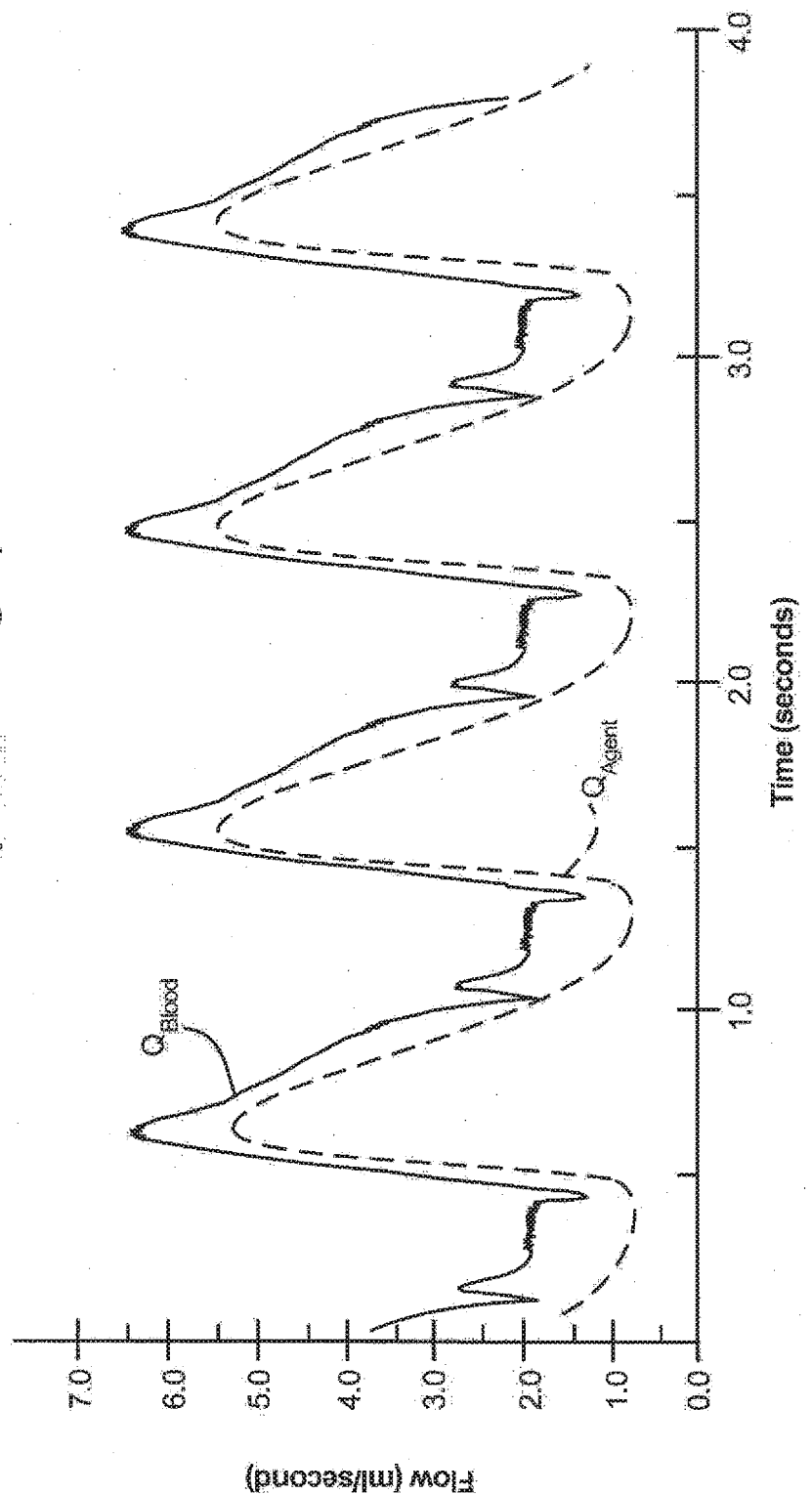
FIG. 13 illustrates graphically an exemplary agent injection profile (flow rate) synchronized with the exemplary blood flow rate profile of FIG. 2.

In addition to modulating injections by reducing inefficient agent use (as illustrated as areas A, B and/or C in exemplary injection profile $Q_{Agent}$ of FIG. 4B), modulation may also advantageously include delivering medium to a vessel in greater quantity when there is greater blood flow, and in lesser quantity when the blood flow is diminished. It is an objective of at least some embodiments described herein to pattern the injection of medium into a vessel to coincide roughly with the pattern of blood flow in that vessel. By way of example, FIG. 13 illustrates an exemplary injection profile delivered by an inventive injection system in which the injection profile coincides roughly with the blood flow within the vessel of FIG. 2. In this case, an average of about 2.8 ml/second of agent (e.g., average of $Q_{Agent}$) may be used to fill the vessel in sufficient quantity (e.g., to perform its opacification function) while not forcing the vessel to fully fill with agent, or otherwise displacing all of the normal blood flow. Thus, the dotted-line in FIG. 13 highlights the profile produced by the injection system in filling the vessel with medium of about 65% to 85% of the normal blood flow, for example. The amount needed for medium concentration (e.g., within in the blood) may vary depending on the agent and the intended function, and it is possible that such concentrations could be provided at as low as 1% of the blood flow rate and at as great as 99% of the blood flow rate without deviating from the intent of the modulation devices and methods described herein.

Synchronized delivery of agent may reduce the risk of "over-filling" the vessels outside of the target vasculature. In addition, such an injection flow rate profile may provide sufficient agent concentration within the vessel for opacification during lower flow. Over-injecting the coronary vasculature (for diagnostic or therapeutic purposes) may be seen arteriographically as "blow back" or reflux, and loads the body with unnecessary agent(s). Examples of synchronization embodiments may involve sensors and controllers utilized to modulate the injection of medium into the target site. Such sensors/controllers might include an EKG (and/or inputs from an EKG) to initiate activation and deactivation, or modulation, of an injector to deliver medium to a vessel as a function of the pulsatile flow of blood in the vessel. Other embodiments may include sensors positioned into, upon, and/or proximate, an injection delivery catheter so as to infer or deduce a parameter of blood flow (pressure, flow rate, temperature, velocity, patient respiration, pH, $pO_2$, etc.) in an effort to coordinate the injection of medium with the flow of blood in the vessel.

Figure 14:
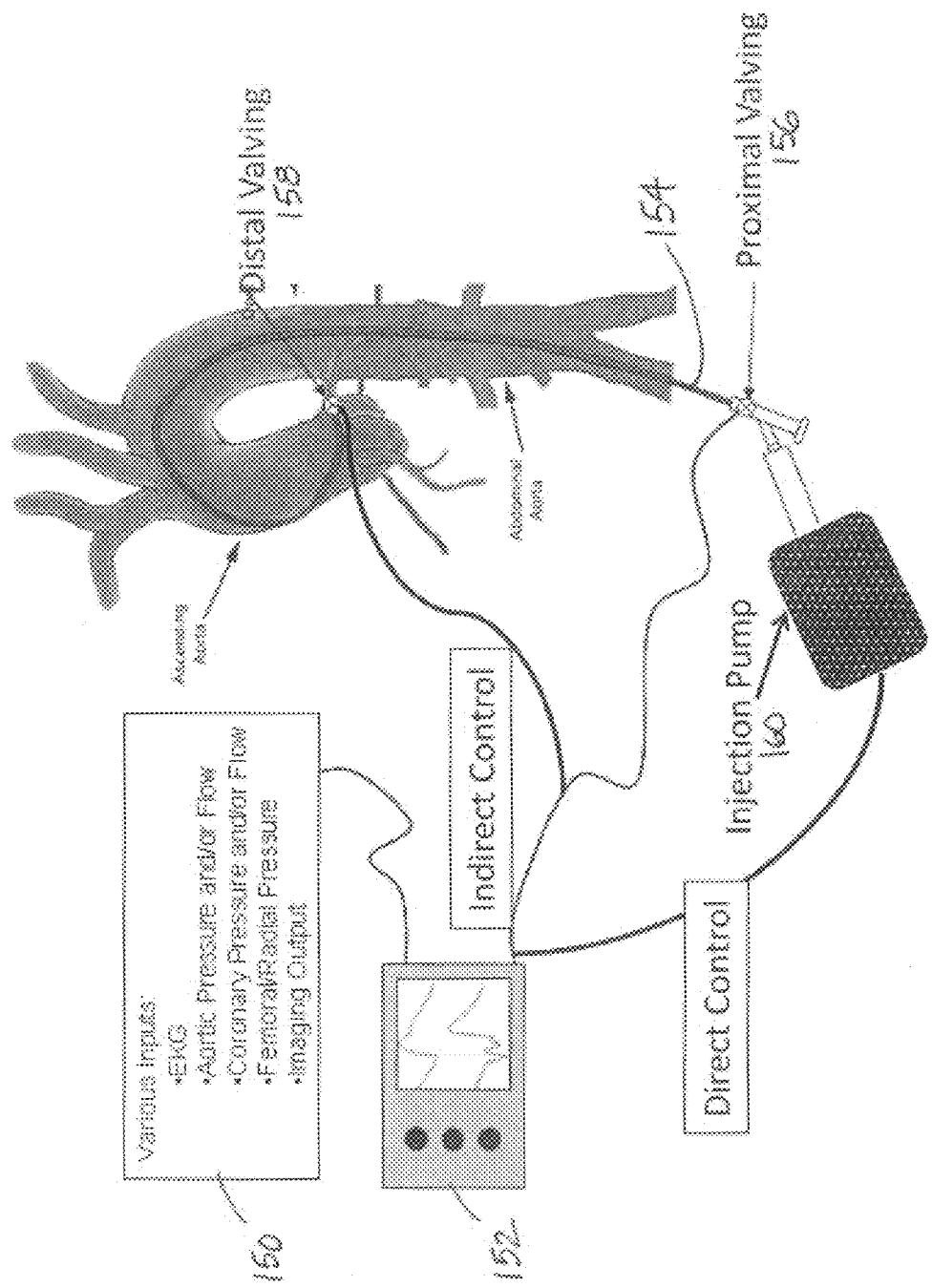
FIG. 14 illustrates exemplary schemas of synchronized agent delivery modulation systems.

FIG. 14 illustrates exemplary schemas for a synchronized medium injection modulation system. As shown, one or more signal sensors 150 may each receive a signal representing, deducing, or inferring, the status of at least one parameter of flow at the target injection site such as the left coronary arteries of the heart. A controller 152 may receive the signal(s) from the sensor(s) 150 and then directly, or indirectly, activate modulated delivery of medium though the delivery catheter system 154. As can be seen in FIG. 14, valving (or otherwise modulating mechanisms) may be positioned near the proximal portion of the delivery system 154 (e.g., in proximity of the delivery catheter proximal portion, outside of the body, as at proximal valving 156), and/or may be placed in, around, and/or in proximity of the distal portion of the delivery catheter (e.g., inside of the body, as at distal valving 158), with such valving being actuated by the controller 152. Further, one or more of the sensor signals may be from a sensor located externally of the body such as an EKG, and/or one or more of the sensor signals may be derived from a sensor within the body (such as a pressure sensor placed in, about and/or in proximity to the distal portion of the catheter).

Figure 15:
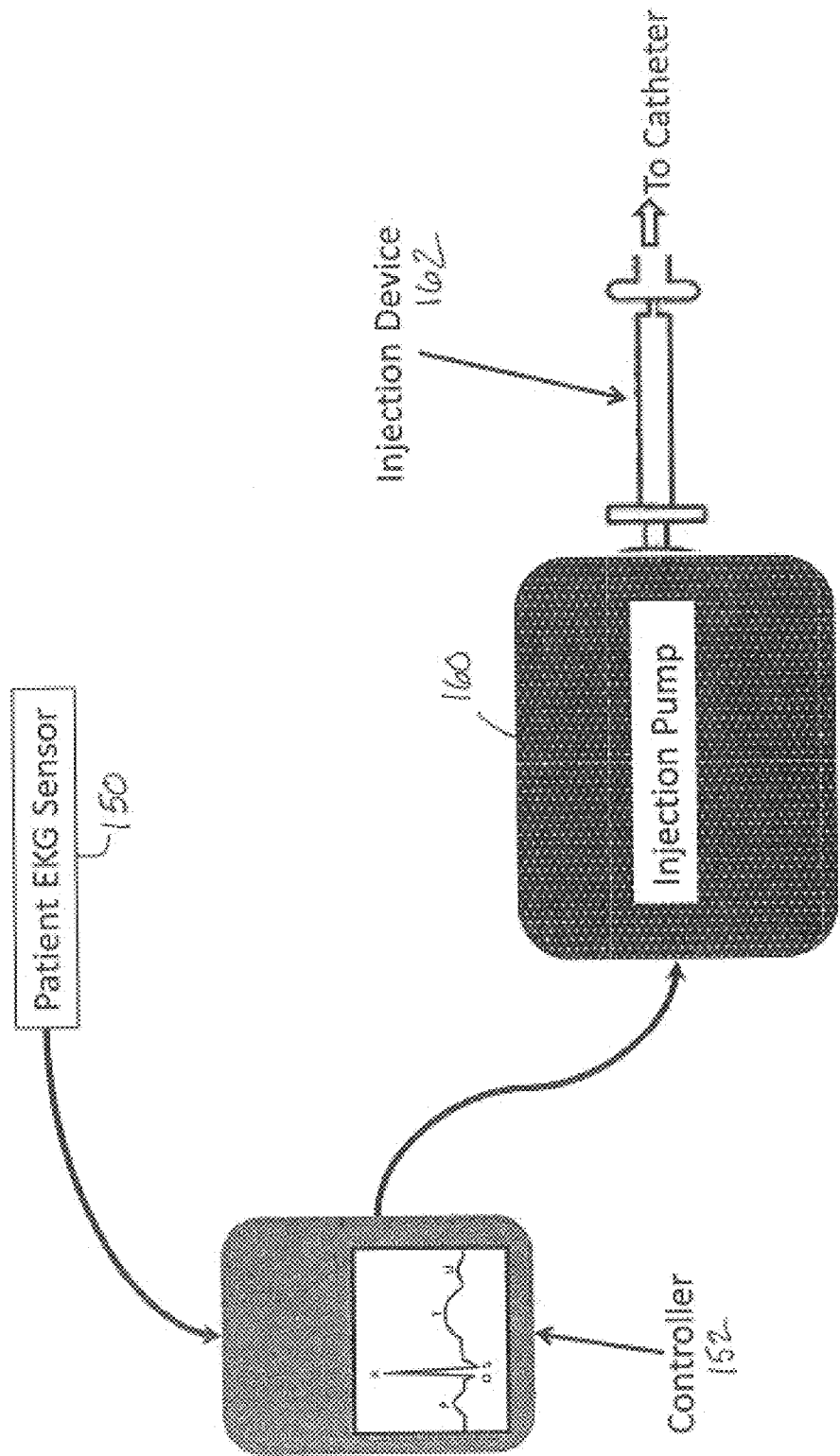
FIG. 15 illustrates an exemplary synchronized agent delivery with direct modulation.

Direct control of modulation may include, for example, activating the injection device directly to synchronize dispensing of medium through the injection delivery catheter to produce the injection flow rate (e.g., $Q_{Agent}$) profile as shown in exemplary FIG. 13. In this example, a signal from a sensor 150 (such as, for example, an EKG signal) is used by the controller 152 to directly actuate the injector pump 160 so as to increase/decrease the injector output to produce a medium agent injection flow rate (e.g., $Q_{Agent}$) profile as shown in FIG. 13. An example of such a system may be found in FIG. 15. As can be seen, an EKG signal of the patient's heart rate is received from an EKG sensor 150 by the controller 152. The controller 152 may selectively signal a start for increasing flow rate at some time interval after the QRS complex of the EKG, and a start for decreasing flow delivery before and/or during the QRS complex, for example. Thus, the controller 152 of FIG. 15 may then activate/deactivate the pump 160 operably coupled to injector 162 to varying degrees to provide dispensing of medium from the injector 162 when an operator has signaled to the controller 152 that an injection is warranted. The activation/deactivation of the injector pump 160 may be capable of producing an exemplary injection profile ($Q_{Agent}$) as described by FIG. 13.

Figure 16A:
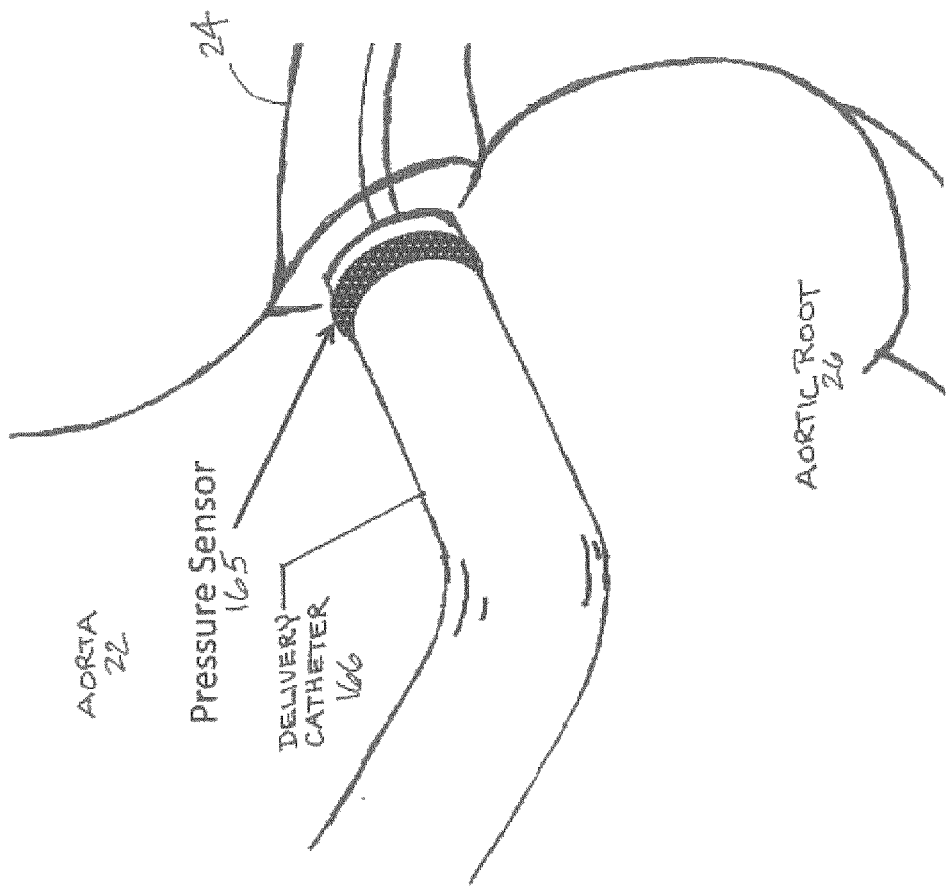
FIG. 16A illustrates an exemplary synchronized agent delivery with indirect modulation, adjacent a distal portion of a treatment system therefor.

Indirect control of modulation may include, for example, valving (or otherwise modulating) an injection dispensed from an injection device. As described previously in the various schemas of FIG. 14, indirect valving (or otherwise controlling mechanisms) may be proximally or distally positioned within, about, and/or upon the agent delivery system 154. An example of an indirect modulation control may be found in FIGS. 16A-16D. In this example, a sensor 165 is deployed distally on a delivery catheter 166 (as seen in FIG. 16A) and a modulating device (of FIG. 16B) is provided proximally (i.e., positioned proximally as shown for modulator 168 of FIG. 16C, for example). The sensor 165 of FIG. 16A is an exemplary pressure sensor positioned on the distal tip of the delivery catheter 166. As described previously, this is only one example of the various sensors that may be used in obtaining a signal to synchronize the delivery of medium with the blood flow rate. Moreover, FIG. 16A illustrates the positioning of the sensor 165 upon the distal tip of the delivery catheter 166. The exemplary positioning of the sensor 165 in FIG. 16A should not be limited to that shown in order to perform the functions described herein, since there may be a multitude of sensor types (and commensurate signals) positioned at various locations on (i.e., as a function of respiration), through (i.e., as a function of imaging) and within the body (i.e., as a function of a variable proximate a target delivery site). Clearly, even the placement of a distal pressure sensor in exemplary FIG. 16A could take many forms, such as: a pressure wire alongside the catheter; a lumen within the catheter body for pressure measurement; a pressure sensor deployed within the distal tip of the catheter; a pressure sensor deployed distally of the distal tip of the catheter and into the target vessel, to name but a few.

Referring to FIG. 16B, modulating device 168 may comprise an inlet port 170 (from the injection device) and an outlet port 172 (to the delivery catheter 166). The flow of injection fluid may pass through the injection port 170 and into a fluid chamber 174 within a body or housing 176 of the modulator 168. The modulator 168 may have a plurality of vane/plates 178 attached to a cylindrical hub 180 disposed within the fluid chamber 174. The vanes 178 and hub 180 may be formed to define a "pinwheel" structure of vane-hub that is capable of rotating freely (relative to fluid chamber 174 and body 176 of modulator 168) upon the injection of medium into the fluid chamber 174 through the injection port 170. The hub 180 may be designed to preferentially rotate in one direction. For example, FIG. 16B illustrates the preferential flow of fluid and rotation of the vane-hub, in a clockwise direction, via flow arrows 182. From the fluid chamber 174, injection fluid may flow out of the modulator 168 via the outlet port 172.

One advantage of a vane-hub modulator design of this type is that it may be easy to measure, or otherwise identify, the total volume of injection fluid delivered through the modulating device 168 (over time) since the volume of fluid passing through the device 168 during one rotation of the vane/hub may be easily determined, and the number of rotations simply counted by a counting mechanism. Alternatively, each "cell" of fluid between adjacent vanes 178 may be readily counted by a counting mechanism. The counting mechanism is not shown in the illustrations, but it may comprise a magnetic, mechanical, ultrasonic, infrared or similar measurement device capable of identifying the number of times a vane 178 and/or some other element of the vane-hub has passed within its field of measurement, or by determining the number of times the axis of the hub 180 has rotated. The output of such a counting device may be utilized to determine and display (in real-time) the total volume of medium used during a procedure. Advantageously, in the management of medium injected, an operator/physician may readily see the amount of medium used (as determined by the counting device and presented by a suitable display or indicative output). The determination of the volume (via calculations/conversions based on, for example, counted rotations) may be performed as part of the counting device, or may be performed by a display device. In addition to providing volume measurements, the counting mechanism/signal/display may incorporate various algorithms to alert an operator/physician before, or at a point which, a maximum volume of agent has been administered (i.e., operator determined value, Maximum Acceptable Contrast Dose, GURM ratio, etc.).

Continuing with the description of the exemplary modulation device 168 shown in FIGS. 16B-16C, a vane-hub modulator may comprise two components. One component 186 may be situated adjacent a controller/actuator 185 and may comprise the input port 170, the output port 172 and the fluid chamber 174 with rotating vane/hub 178/180. This component of the system, which may come into contact with fluids, may be disposable if so desired. A second component 188 comprising the controller/actuator 185, brake mechanism 191, sensor signal 190 receiver, and the like may be used to clutch, brake, or otherwise inhibit the rotation of the vane-hub so as to provide resistance to rotation. The resistance induced to the rotation may be coordinated with a signal 190 from sensor 165 of FIG. 16A, so as to modulate an injection from an injector to produce an agent fluid flow ($Q_{Agent}$) profile as described, for example, in FIG. 13.

The braking, or clutching of the modulator 168 of FIG. 16C may be performed through a variety of means, to include, for example, mechanical, hydromechanical, electromechanical, electromagnetic, chemomechanical, etc. FIG. 16C illustrates one such means 191 for braking the shaft 192 of the vane-hub, using electromagnetic means. The exemplary braking structure 191 is further detailed in FIG. 16D, wherein the longitudinal shaft 192 of the hub 180 is coupled to a hysteresis plate/disc 194 positioned within a magnetic field 196. When electricity is applied to the magnetic coil 196, a magnetic flux is transferred to the hysteresis disk 194 (as it passes through the field) causing a magnetic "drag" on the disc 194. The drag, or braking, applied to the hysteresis plate 194 (and thus the shaft 192 of the vane-hub) may be increased/decreased with increasing/decreasing voltage applied to the magnetic field to modulate the flow of medium as intended. When electrical current is removed, the connected disc/shaft may rotate freely about an axis of shaft 192. In the example of FIG. 13, the maximum flow rate of agent ($Q_{Agent}$) is approximately 5.2 ml/second. Therefore, in producing profile of $Q_{Agent}$ of FIG. 13, one might set the injection of medium into the modulator 168 at a constant rate of 5.2 ml/second. Upon modulating, braking mechanism 191 of FIG. 16D may increase the drag (reduce the flow rate) of the agent as needed to produce the flow profile of $Q_{Agent}$ of FIG. 13.

FIGS. 16B and 16C describe one of numerous means to regulate the flow profile of injection agent thru a modulator, and as such, are intended to illustrate the modulation monitoring and control concepts disclosed herein without limitation. Of course, such means may be employed with various signals and sensors (such as shown in FIG. 16A) to "synchronize" the flow of injection medium with corporeal medium flow. Therefore, the example of FIG. 16 is but one example how one might use a modulator device to perform synchronization.

Figure 23:
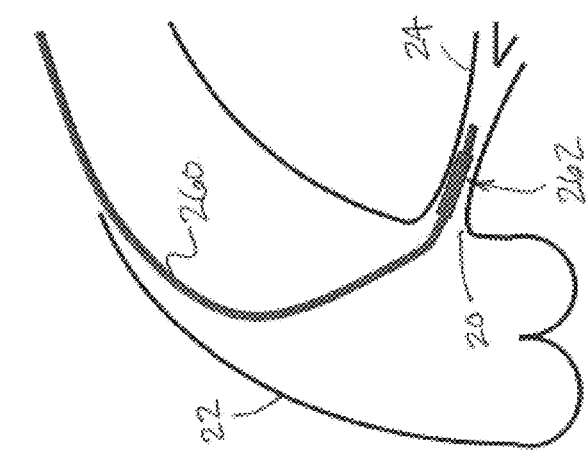

Previous embodiments of "synchronized" delivery described herein may include active sensing and subsequent modulating of the delivery of a medium. However, delivery of a medium to a delivery site may be also modulated by passively valving the medium delivery as a function of a physical attribute in and/or around the delivery site; such as pressure, for example. Referring to FIG. 23, a delivery catheter 260 may be placed to deliver a medium to a delivery site, such as the left main 24 of the coronary vasculature. In this setting, there are continuously changing pressures within the left main 24 as well as the aorta 22, as previously described. A valving mechanism 262 may be deployed within, on or in proximity of the distal portion of the delivery catheter 260.

Figure 24A:
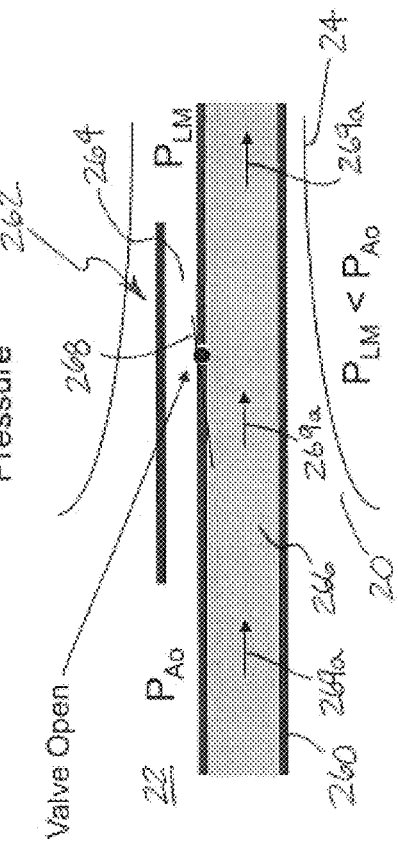
FIGS. 23, 24A and 24B illustrate an exemplary passive blood flow and medium flow valving mechanism operable as a function of a physical attribute in and/or around a medium delivery site.
Figure 24B:
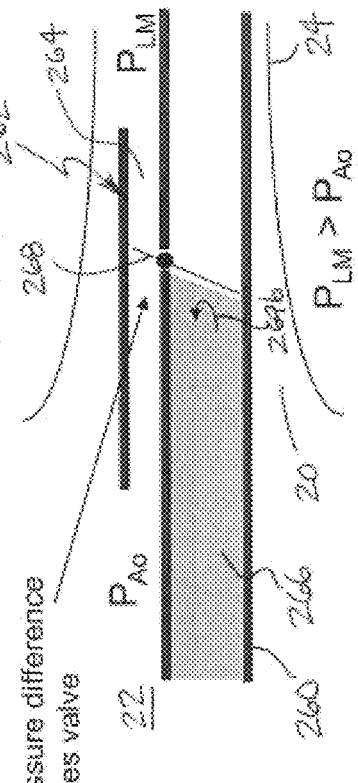

FIGS. 24A and 24B illustrate in more detail the distal portion of the catheter 260 with a passive valving mechanism 262 present. As shown in FIGS. 24A and 24B, the valving mechanism may include a blood flow bypass lumen 264, allowing some blood flow alongside medium delivery lumen 266 of the catheter 260. A passive valve gate 268 is disposed to limit blood flow through bypass lumen 264 and medium flow through medium lumen 266, as a function of pressure differential around the delivery site. As shown in the FIG. 24A, when the pressure within the left main 24 (e.g., $P_{LM}$) is less than the pressure in the aorta 22 (e.g., $P_{AO}$), the valve gate 268 of delivery catheter 260 may allow the injection of medium to the delivery site (as illustrated by medium flow arrows 269a in FIG. 24A). Conversely, as shown in FIG. 24B, as the pressure differential between the left main 24 and the aorta changes 22, with the left main 24 increasing in pressure with respect to the aorta 22 (e.g., slowing of blood flow into the left main 24), the passive valve gate 268 may act to hinder, or reduce, the delivery of medium to the delivery site (as illustrated by the medium flow arrow 269b in FIG. 24B). Thus, the device of FIGS. 23, 24A and 24B provides an arrangement that may allow "synchronized" delivery of medium to the coronary vasculature as a function of a passive valve mechanism.

FIGS. 25A and 25B illustrate another embodiment of passively valving the distal portion of a catheter so as to improve the efficiency of delivery of medium to a delivery site. FIG. 25A illustrates a delivery catheter 270 that may be placed in a sealing relationship (partial or total) with a coronary artery 25 such as, for example, as at catheter/artery interface 272. With such use, there may be a concern that blood flow from the aorta 22 is restricted from perfusing the occluded artery 25. However, as shown in FIG. 25A, distal portion of delivery catheter 270 may have a valve 274 and orifice(s) 276 disposed distally of the valve 274 so as to provide perfusion from the aorta 22, through the catheter 270, and distal to the delivery catheter (i.e., into the artery 25) when medium injection is not taking place. In this instance, valve 274 is closed, allowing blood to flow into orifice(s) 276, through the distal portion of the catheter 270, and past the catheter/artery interface 272. The valve 274 thus acts to allow blood flow distally, as illustrated by blood flow arrows 278 in FIG. 25A (while inhibiting the flow of medium past valve 274). Conversely, as shown in FIG. 25B, when delivery of medium is warranted, valve 274 may be deployed so as to reduce perfusion from the aorta 22 and allow medium delivery to the delivery site. In this instance, valve 274 is open, allowing medium to flow past valve 274, through the distal portion of the catheter 270, and past the coronary/artery interface 272. The valve 274 thus acts to allow medium flow distally, as illustrated by medium flow arrows 279 in FIG. 25B (while inhibiting the flow of blood past valve 274).

There are many forms wherein the passive distal valving of a delivery catheter may be employed to further enhance the efficiency and/or effectiveness of medium delivery to a delivery site. The previous examples are illustrative of the inventions, and should not be interpreted as limiting in their scope.

In addition to the various embodiments described herein to effect more efficient delivery of medium to a target site, the modulation of an injection may be further enhanced with various delivery catheter tip configurations, thus advantageously changing the flow characteristics in, around and/or proximate the delivery site. For example, FIGS. 17A-17D illustrate four embodiments that may be employed to perform such a function. As previously described by FIGS. 5A and 5B, it is clear that at least one of the challenges associated with the delivery of medium may involve the location of the delivery catheter tip and the pressure differentials surrounding the tip. FIGS. 5A and 5B illustrate a catheter delivery tip within the aorta 22, at the ostium 20 to the left main 24. This "catheter tip" placement may be common since physicians may be hesitant in delivering the tip of the catheter into the left main due to concerns of injuring/disrupting the vessel wall and/or causing spasms (and thus acute occlusion) within the left arterial system. If the delivery catheter is positioned as such, there may be little "driving force" (e.g., pressure differential) to preferentially deliver the medium from the delivery catheter tip into the ostium, versus into the aorta (and, thus systemically). FIGS. 17A-17D show various embodiments that may preferentially modulate the environment surrounding and/or proximate the delivery catheter tip in order to enhance the delivery of agent into the ostium. In many regards, these embodiments may also act to isolate/control the environment surrounding the delivery catheter distal delivery portion so as to accommodate more efficient delivery of a substance.

For example, FIG. 17A illustrates a delivery device 210 that may have a balloon inflated around its distal portion 212 so as to increase the pressure within the aorta 22 (at least during injection), and further "drive" the injection medium into the ostium 20. The embodiment of FIG. 17B illustrates a conical member 222, surrounding the catheter delivery tip of delivery device 220, which may act to capture/isolate medium, and/or increase flow resistance (when deployed) for the medium to flow to the aorta 22; and thus, preferentially "drive" the medium into the left main 24. $P_{AO}$ and $P_{LM}$ of FIG. 17B designate areas of pressure within the aorta (e.g. $P_{AO}$) and the left main (e.g., $P_{LM}$) solely for the purpose of identification. The conical member 222 may also be expandable; as well as the expansion of 222 could further be in response to the pressure gradient between $P_{AO}$ and $P_{LM}$.

The alternative exemplary embodiment described by FIG. 17C shows a delivery device 230 that includes a coaxial member or sleeve 232 surrounding a distal catheter delivery portion 234 and may, in essence, act to artificially "extend" the left main 24 into the aorta 22. Thus, upon injection of medium, the flow of the medium is subjected to greater resistance to flow along the path to the aorta 22 (via the sleeve 232) than would be present flowing to the ostium 20. In some ways, the coaxial nature of the coaxial 232 member may also advantageously function as a distal "reservoir" of medium, acting to store and then release medium from the temporary reservoir structure in response to the cyclical pressure changes seen, for example, by the left main 24.

FIG. 17D illustrates another embodiment in the modulation of the flow parameters surrounding the delivery catheter distal portion. As shown, a delivery device 240 has a delivery catheter tip with a coaxially expandable sheath 242 surrounding a distal portion of the catheter. When expanded, the sheath 242 could partially engage the ostium 20, as at 244 for example. The expansion of the sheath 242 may be actuated by the flow of injected medium through at least one or more orifices 246 along the distal portion of the catheter. The expanded sheath 242, when deployed, may create greater resistance to flow (for agent) along the path to the opening 20 of the aorta 22, than along the path into the left main 24, as indicated by the flow arrows in FIG. 17D.

There are many variations to the structures and configurations exemplified in FIGS. 17A-17D which may modulate, or otherwise control or isolate, the pressure and/or flow environment surrounding a distal portion of the delivery catheter. FIGS. 17A-17D are illustrative of embodiments that advantageously modulate the flow characteristics in, around and/or proximate the delivery site and, as such, should not be viewed as limiting the scope of the structures and methods for achieving such flow characteristics.

In addition to the various disclosed arrangements and processes that may act to modulate the environ of flow characteristics in, around and/or proximate the delivery site, other delivery catheter distal tip designs might advantageously "mix" the medium with the blood. The applicants have found that in at least some medium delivery scenarios (i.e., agent, target site, flow parameters) it may be necessary for the injected medium to travel a distance from the distal tip of the catheter before the medium may be sufficiently "mixed" with the blood flow (e.g., homogenous concentration of the medium within the blood). In the example described by FIGS. 5A and 5B, it is possible that an injected agent may not reach a homogenous concentration within the blood flow for some distance distally along the left main and/or arterial supply from the ostium. As an example, if it were to take approximately 2 cm to 3 cm for the medium to mix with the blood, then this distance along the vessel may not be "well opacified." In this situation, an operator of an injector may continue to increase the medium delivery in order to obtain greater opacification of the vessel. A delivery catheter having a distal tip construction as shown, for example, in FIG. 18 may be able to more readily mix the medium exiting the catheter with the blood flowing by the catheter, and therefore may advantageously reduce the amount of medium necessary to see the opacification of the artery.

The example of FIG. 18 shows a delivery catheter 250 having ribbed undulations 252 along the inner surface of its distal tip 254 so as to provide a flow pattern resembling a vortex 256 of the medium exiting the catheter 250. The disrupted medium flow pattern may more readily mix the medium and blood. Although FIG. 18 illustrates ribbed undulations along the inner surface of the delivery catheter, it is clear that there may be other structures and configurations that may perform the same function (such as: structures along the inner and/or outer diameters of the delivery catheter; structures deployed within the blood, distal to the catheter tip, to agitate/disrupt the blood/medium flow; structures such as orifices placed along the distal portion of the catheter to allow medium/blood mixing within the delivery catheter; etc.). In connection with the notion of mixing the medium and blood, FIG. 18 is only intended to illustrate an exemplary arrangement and process for doing so.

Note that "tip" of the catheter as used may be synonymous with the "distal portion," or any other portion of the catheter that may reside within the patient's body (e.g., distal of the proximal portion of the delivery catheter) and might play a role in the delivery of an agent to an intended target site.

In summarizing many of the embodiments described herein, there are numerous occasions in the diagnostic, prophylactic and treatment practice of medicine wherein an agent, substance, material, medicant, or medium is preferably delivered to a specific site within the body. Some of the examples described herein have advantageously comprised delivery control attributes that may derived from one or more of the modulating elements/functions illustrated in FIG. 19 (i.e., injection device type, regulation type, sequential versus direct delivery, synchronization with corporeal flow, activation/deactivation at pump versus after pump, flow environ manipulation). FIG. 19 attempts to summarize some of the described elements/functions with reference to illustrative FIGS. of this disclosure and/or their descriptions. As importantly, the various elements/functions in media delivery modulation are not, per se, mutually exclusive since one or more of these elements/functions may be used in combination to derive control attributes desired. As such, the various elements/functions identified in FIG. 19 may be selected (e.g., "mix-and-matched") to produce a modulator that optimally performs an intended purpose. For example, one might consider a variety of attributes in performance of medium modulating function, such as: target site location, target site access, fluid dynamics proximate the target site, agent to be delivered (e.g., quantity, viscosity, toxicity), injection frequency, concentration of agent within target site, target site isolation, ease of use of modulator, complexity in administration, cost of the system, and cost of agent, to name a few.

FIG. 19 should be considered a general summary for guiding the reader in identifying an exemplary function/element. Therefore, FIG. 19 is not, per se, inclusive of all the figures and descriptions within this disclosure that may contain a particular function/element; nor, is FIG. 19 inclusive of all embodiments disclosed herein.

Many of the examples of systems illustrated have involved the delivery of a cardiovascular contrast agent. However, there are many other applications wherein the controlled delivery of a substance to a specific structure/organ/site of the body may also benefit from the devices and methods disclosed herein. Due to the variety of medical applications, as well as the diversity of means to modulate (for example, elements/functions of FIG. 19) there may be a multitude of mechanisms employed to produce a modulator for its unique and intended purpose. An example of how one might go about employing various elements/functions in the construction of a modulator device is further described below, as it pertains to a non-cardiovascular procedure of lymphography.

Lymphography employs the delivery of an imaging agent to the lymphatic system wherein an agent is injected, and subsequently radiograph(s) taken, in the visualization of metastatic cancer cells. Procedurally (and after identifying the lymphatic), a needle/catheter may be inserted into a lymphatic channel/vessel in the foot (near the base of the first metatarsal) and a contrast medium (such as Ethiodol) may injected into the body at a very slow rate (approximately 60 to 90 minutes). The total quantity of injection might be 6-7 ml. The patient typically remains on his or her back during the procedure. Once the injection is complete, radiographs may be taken. Of note, the "flow" of fluid in the lymphatic system is consistently slow, as compared to the high flow and variability of the coronary arteries. Moreover, the lymphatic channel/vessels may be very sensitive (e.g., rupture) to over-pressurization.

Given the description of the lymphatic example (and referring to FIG. 19), one might construct a modulator with elements/functions that satisfy the following attributes: long delivery time; small volume delivered; constant flow rate; sensitivity to over-pressurization; sufficiently portable/movable to accommodate patient during the delivery; and, equal to or less expensive than using an automated injector. Given these attributes one might consider a manually-loaded injector device to deliver the medium sequentially (delayed) wherein the device may be filled with an amount of fluid to be delivered (e.g., 6 ml) first, and upon release of the injection, may deliver the medium over an extended period of time (e.g., 90 minutes). An element in regulation might include a device with constant flow rate (i.e., constant flow rate irrespective of variable pressures), or a regulator element that functions with constant pressure differentials (i.e., irrespective of variable flow rates). Because of the high sensitivity to pressures in the lymphatic, the latter alternative might be more amenable in accommodating high pressure "spikes" (for example, if the delivery catheter were to occlude during the delivery). Viewing FIG. 19, elements of corporeal flow synchronization, flow activation (via signal), and distal environ alternation may be less important, and therefore those features may not be included in the exemplary device construction. Ultimately, a multi-component, sequential delivery device as illustrated and described in FIGS. 9A-9C may simply modulate the delivery of a controlled amount of agent, without the risk of rupturing the lymphatic channels/vessels due to over-pressurization. The sequential delivery allows for filling a precise amount of fluid to be delivered, and once the lymphatic vessel is accessed, may continue to deliver the medium over time.

Clearly, the lymphatic medium delivery is but one additional, non-cardiovascular example and it is intended to help further illustrate how the various elements and components disclosed herein may be used in a variety of ways to satisfy a multitude of clinical applications in the delivery of a fluidal substance.

It should be understood that the medium delivery modulation devices and methods described herein are not limited to the particular, representative embodiments as described, since variations may be made to these embodiments without departing from the scope and spirit of the disclosure. Likewise, terminology employed in the description of embodiments is not intended to be limiting and is used merely for the purpose of conveyance of the concept. Unless defined otherwise, all technical and scientific terms used herein have the same meaning as commonly understood to one of ordinary skill in the art of which the disclosed devices and methods pertain.

The invention claimed is:

1. A method for mechanically modulating a fluid medium delivered to a vascular site within a body of a patient, the method comprising:
   employing a system including:
      a sterile medium container that contains the fluid medium;
      an injector;
      a delivery catheter configured to deliver the fluid medium from outside the body of the patient to the vascular site within the body of the patient;
      a chamber disposed between the injector and the delivery catheter;
      a first connector, said first connector being fluidly coupled to each of the injector, the chamber, and a second connector, wherein the first connector is fluidly coupled to the chamber via a first valve;
      the second connector being fluidly coupled to the sterile medium container via a second valve, and the second connector being fluidly coupled to the delivery catheter, wherein the second connector resides between the first connector and the delivery catheter;
   injecting the fluid medium from the injector to the first connector, wherein the first valve is open;
   simultaneously accepting a portion of the injected fluid medium into the chamber, wherein said chamber comprises at least one surface that imparts a force on the fluid medium within the chamber;
   delivering the fluid medium to the vascular site within the body of the patient through the delivery catheter at a flow rate that remains substantially unchanged during the injecting of the fluid medium; and
   drawing the fluid medium from the sterile medium container and filling the injector with the drawn fluid medium, wherein the first valve is closed and the second valve is open.

2. The method of claim 1, wherein said force within the chamber is produced at a constant, predetermined value.

3. The method of claim 1, wherein said injector is a syringe.

4. The method of claim 1, wherein said flow rate of the fluid medium through the delivery catheter is a function of a second force applied by the injector and the force applied by the chamber.

5. The method of claim 1, wherein the flow rate of the fluid medium delivered by the delivery catheter corresponds to a pressure range of the fluid medium within the chamber.

6. The method of claim 1, further comprising directing flow of the fluid medium from the chamber to a location other than the delivery catheter.

7. The method of claim 1, wherein the fluid medium is a contrast agent, and the flow rate of the delivered fluid medium is sufficient to opacify a blood vessel at the vascular site.

* * * * *